US011434479B2

(12) United States Patent
Yang et al.

(10) Patent No.: US 11,434,479 B2
(45) Date of Patent: Sep. 6, 2022

(54) SIALIC ACID BINDING POLYPEPTIDE

(71) Applicants: UNIVERSITY OF GEORGIA RESEARCH FOUNDATION, INC., Athens, GA (US); GLYCOSENSORS AND DIAGNOSTICS, LLC, Athens, GA (US)

(72) Inventors: Loretta Yang, San Diego, CA (US); Kausar N. Samli, Kirkland, WA (US); Robert J. Woods, Athens, GA (US); Shengcheng Wu, Athens, GA (US); John C. Cooper, Brooklyn, NY (US); Mallory K. Paul, Washington, DC (US); Matthew J. Saunders, San Diego, CA (US); Ziad M. Eletr, Somerville, MA (US)

(73) Assignees: University of Georgia Research Foundation, Inc., Athens, GA (US); Glycosensors and Diagnostics, LLC, Athens, GA (US)

( * ) Notice: Subject to any disclaimer, the term of this patent is extended or adjusted under 35 U.S.C. 154(b) by 125 days.

(21) Appl. No.: 16/607,508

(22) PCT Filed: Apr. 24, 2018

(86) PCT No.: PCT/US2018/029079
§ 371 (c)(1),
(2) Date: Oct. 23, 2019

(87) PCT Pub. No.: WO2018/200478
PCT Pub. Date: Nov. 1, 2018

(65) Prior Publication Data
US 2021/0009975 A1 Jan. 14, 2021

Related U.S. Application Data

(60) Provisional application No. 62/489,243, filed on Apr. 24, 2017.

(51) Int. Cl.
C12N 9/24 (2006.01)
G01N 33/573 (2006.01)
A61K 38/00 (2006.01)

(52) U.S. Cl.
CPC ......... *C12N 9/2402* (2013.01); *G01N 33/573* (2013.01); *A61K 38/00* (2013.01); *C07K 2319/00* (2013.01); *G01N 2333/924* (2013.01)

(58) Field of Classification Search
None
See application file for complete search history.

(56) References Cited

U.S. PATENT DOCUMENTS

| | | | |
|---|---|---|---|
| 5,352,607 A | 10/1994 | Laine et al. | |
| 5,587,292 A | 12/1996 | Laine et al. | |
| 6,090,573 A | 7/2000 | Laine et al. | |
| 6,159,719 A | 12/2000 | Laine et al. | |
| 6,184,027 B1 | 2/2001 | Laine et al. | |
| 6,376,210 B1 | 4/2002 | Yuan | |
| 6,972,172 B2 | 12/2005 | Dukler et al. | |
| 7,368,108 B2 | 5/2008 | DeFrees et al. | |
| 7,455,979 B2 | 11/2008 | Markman | |
| 7,741,061 B2 | 6/2010 | Markman | |
| 8,119,357 B2 | 2/2012 | Amor et al. | |
| 9,926,612 B2 | 3/2018 | Woods et al. | |
| 10,358,637 B2 | 7/2019 | Samli et al. | |
| 11,001,824 B1 | 5/2021 | Samli et al. | |
| 2004/0077105 A1 | 4/2004 | Wu et al. | |
| 2004/0229314 A1 | 11/2004 | Glucksmann et al. | |
| 2006/0040327 A1 | 2/2006 | Amiss et al. | |
| 2006/0141480 A1 | 6/2006 | Ramnarayan et al. | |
| 2006/0172339 A1 | 8/2006 | Patton et al. | |
| 2009/0272913 A1 | 11/2009 | Naciri et al. | |
| 2010/0016171 A1 | 1/2010 | Wong et al. | |
| 2011/0257032 A1 | 10/2011 | Sasisekharan et al. | |
| 2012/0040474 A1* | 2/2012 | Woods | C12Y 302/01169 436/501 |
| 2014/0005069 A1 | 1/2014 | Yang et al. | |
| 2017/0128554 A1 | 5/2017 | Chen et al. | |
| 2017/0191049 A1 | 7/2017 | Samli et al. | |
| 2018/0259508 A1 | 9/2018 | Woods et al. | |

FOREIGN PATENT DOCUMENTS

| | | |
|---|---|---|
| JP | 2002-503093 | 1/2002 |
| JP | 2008-507983 | 3/2008 |
| JP | 2008-518023 | 5/2008 |
| WO | 98/42864 | 10/1998 |
| WO | 2005/007826 | 1/2005 |
| WO | 2006/047639 | 5/2006 |
| WO | 2006/093529 | 9/2006 |
| WO | 2007/130453 | 11/2007 |
| WO | 2010/068817 | 6/2010 |

(Continued)

OTHER PUBLICATIONS

BLASTP sequence alignment of *Streptococcus pneumonia* neuraminidase NanB and PNGase F. Downloaded Oct. 8, 2021 (Year: 2021).*
Galab Technologies, "Lectins: Benefits" informational webpage. Geesthacht, Germany. [retrieved on Jan. 27, 2012]. Retrieved from the Internet: galab.de/technologies/products/lectins.html; 1 page.
Gao et al., "Dynamic O-glycosylation of nuclear and cytosolic proteins: cloning and characterization of a neutral, cytosolic beta-N-acetylglucosaminidase from human brain," J Biol Chem, Mar. 30, 2001. 276(13):9838-45. Available online on Jan. 8, 2001.
Garman and Garboczi, "The molecular defect leading to Fabry disease: structure of human a-galactosidase," J Mol Biol, Mar. 19, 2004; 337(2):319-35.
Glycam, "Glycam-Web" Screen Shot of Home Page, Athens, GA, Copyright 2013. [retrieved on Nov. 12, 2016]. Retrieved from the Internet: glycam.org/; 1 page.

(Continued)

*Primary Examiner* — Anand U Desai
(74) *Attorney, Agent, or Firm* — Mueting Raasch Group

(57) ABSTRACT

Sialic acid recognizing-affinity reagents engineered from the neuraminidase NanB have lectin-like properties and defined specificities for sialic acid.

16 Claims, 23 Drawing Sheets
Specification includes a Sequence Listing.

(56) References Cited

FOREIGN PATENT DOCUMENTS

| | | |
|---|---|---|
| WO | 2012/118928 | 9/2012 |
| WO | 2012/170678 | 12/2012 |
| WO | 2015/161201 | 10/2015 |
| WO | 2018/200478 | 11/2018 |

OTHER PUBLICATIONS

Habbersett and Jett, "An analytical system based on a compact flow cytometer for DNA fragment sizing and single-molecule detection," Cytometry A, Aug. 2004; 60(2):125-34.

Hakomori, "Tumor-associated carbohydrate antigens," Ann Rev Immunol, 1984; 2:103-26.

Haslam et al., "Core fucosylation of honeybee venom phospholipase A2," Glycobiology, Apr. 1994. 4(2):105-6.

Hayes et al., "Combining computational and experimental screening for rapid optimization of protein properties," Proc. Natl. Acad. Sci. USA, Dec. 10, 2002. 99(25):15926-31. Available online on Nov. 21, 2002.

Heikinheimo et al., "The structure of bovine lysosomal a-mannosidase suggests a novel mechanism for low-pH activation," J Mol Biol, Mar. 28, 2003. 327(3):631-44.

Honegger et al., "Glycosidase Functions in Sperm-Egg Coat Interaction in Ascidians: a Reconsideration and a New Approach," Ascidian News [online]. Dec. 2004. No. 56.

Horimoto and Kawaoka, "Influenza: lessons from past pandemics, warnings from current incidents," Nat Rev Microbiol, Aug. 2005; 3(8):591-600.

Huang et al., "Carbohydrate microarray for profiling the antibodies interacting with Globo H tumor antigen," Proc Natl Acad Sci USA, Jan. 3, 2006; 103(1):15-20. Published online Dec. 22, 2005.

Ibrahim and van den Engh, "High-speed cell sorting: fundamentals and recent advances," Curr Opin Biotechnol, Feb. 2003; 14(1):5-12.

Invitrogen, "Antibody labeling from A to Z: Alexa Fluor to Zenon antibody labeling kits for imaging and flow cytometry" 2008; thermofisher.com/content/dam/LifeTech/migration/en/filelibrary/cell-tissue-analysis/pdfs.par.60486.file.dat/b-075469-zenon%20brochure-flr.pdf; 12 pages.

Jacobson et al., "Three-dimensional structure of ß-galactosidase from E. coli," Nature, Jun. 30, 1994; 369(6483):761-6.

Kaneda et al., "The high specificities of Phaseolus vulgaris erythro- and leukoagglutinating lectins for bisecting GlcNAc or beta 1-6-linked branch structures, respectively, are attributable to loop B," J Biol Chem, 2002; 277(19):16928-35. Published online Feb. 25, 2002.

Karplus and Kushick, "Method for Estimating the Configurational Entropy of Macromolecules," Macromol, 1981. 14:325-332.

Kellar et al., "Multiplexed fluorescent bead-based immunoassays for quantitation of human cytokines in serum and culture supernatants," Cytometry, Sep. 1, 2001; 45:27-36.

Keller et al., "Analytical applications of single-molecule detection," Anal Chem, Jun. 1, 2002; 74(11):316A-324A.

Kettman et al., "Classification and properties of 64 multiplexed microsphere sets," Cytometry, Oct. 1, 1998; 33(2):234-43.

Kirschner et al., "GLYCAM06: A Generalizable Biomolecular Force Field. Carbohydrates," J Comput Chem, Mar. 2008. 29(4):622-655. Available online on Sep. 11, 2007.

Kollman et al., "Calculating Structures and Free Energies of Complex Molecules: Combining Molecular Mechanics and Continuum Models," Acc. Chem. Res. 2000. 33(12):889-97. Available online on Oct. 4, 2000.

Krengel et al., "Structure and molecular interactions of a unique antitumor antibody specific for N-glycolyl GM3," J Biol Chem, Feb. 13, 2004; 279(7):5597-603. Published online Nov. 19, 2003.

Kreunin et al., "Bladder cancer associated glycoprotein signatures revealed by urinary proteomic profiling," J Proteome Research, Jul. 2007; 6(7):2631-9. Published online May 23, 2007.

Krogh et al., "Protein analysis using enzymes immobilized to paramagnetic beads" Anal Biochem, Oct. 15, 1999; 274(2):153-62.

Kuhn et al., "Crystal-Structure of Peptide-N4-(N-Acetyl-ß-D-Glucosaminyl)asparagine Amidase F at 2.2-Å Resolution," Biochemistry, Oct. 4, 1994. 33(39):11699-11706.

Kuno et al., "Evanescent-field fluorescence-assisted lectin microarray: a new strategy for glycan profiling," Nat Methods, Nov. 2005; 2(11):851-6.

Lee, "Characterization of a major cluster of nif, fix, and associated genes in a sugarcane endophyte, Acetobacter diazotrophicus," J. Bacteriol, Dec. 2000. 182(24): 6874-6883.

Lim et al., "Defining the regulated secreted proteome of rodent adipocytes upon the induction of insulin resistance," J Proteome Res, Mar. 2008; 7(3):1251-63. Published online Feb. 1, 2008.

Luminex Corp., "MAGPIX—Multiplexed Genomic, and Proteomic Biomarker Analysis" 2012; Austin, TX. [online] [retrieved on Nov. 2, 2016] from the Internet. Retrieved from the Internet: cic.ugr.es/descargas/lar/PDF4.pdf; 6 pages.

McCartney et al., "Glycoside Hydrolase Carbohydrate-Binding Modules as Molecular Probes for the Analysis of Plant Cell Wall Polymers," Analytical Biochemistry, Mar. 2004. 326(1): 49-54.

Mega and Hase, "Conversion of egg-white lysozyme to a lectin-like protein with agglutinating activity analogous to wheat germ agglutinin," Biochim Biophys Acta, Aug. 18, 1994; 1200(3):331-3.

Millipore Corporation, "MILLIPLEX Map, Your Source for: Luminex xMap Technology" Product Sheet, Copyright 2010; Billerica, MA. 12 pages.

Mizan et al., "Cloning and characterization of sialidases with 2-6' and 2-3' sialyl lactose specificity from Pasteurella multocida," J Bacteriol, Dec. 2000; 182(24):6874-83.

Nolan and Sklar, "The emergence of flow cytometry for sensitive, real-time measurements of molecular interactions," Nat Biotechnol, Jul. 1998; 16(7):633-8.

Nolan et al., "Reagents and instruments for multiplexed analysis using microparticles," Curr Protoc Cytom, Aug. 2006; Chapter 13:Unit13.8.

Nolan and Yang, "The flow of cytometry into systems biology," Brief Funct Genomic Proteomic, Jun. 2007; 6(2):81-90. Published online Jul. 4, 2007.

Norris et al., "The three-dimensional structure of PNGase F, a glycosylasparaginase from Flavobacterium meningosepticum" Structure, Nov. 15, 1994; 2(11):1049-59.

Oelmann et al., "Point mutations identified in Lec8 Chinese hamster ovary glycosylation mutants that inactivate both the UDP-galactose and CMP-sialic acid transporters," J Biol Chem, Jul. 13, 2001; 276(28):26291-300.

Oliver et al., "Multiplexed analysis of human cytokines by use of the FlowMetrix system," Clin Chem, Sep. 1998; 44(9):2057-60.

Packer et al., "Frontiers in glycomics: bioinformatics and biomarkers in disease. An NIH white paper prepared from discussions by the focus groups at a workshop on the NIH campus, Bethesda MD (Sep. 11-13, 2006)," Proteomics, Jan. 2008; 8(1):8-20.

Parsons and Raftery, "The identification of aspartic acid residue 52 as being critical to lysozyme activity," Biochemistry, Oct. 1969; 8(10):4199-205.

Patwa et al., "Screening of glycosylation patterns in serum using natural glycoprotein microarrays and multi-lectin fluorescence detection," Anal Chem, Sep. 15, 2006; 78(18):6411-21.

Pelkonen et al., "Differential activities of bacteriophage depolymerase on bacterial polysaccharide: binding is essential but degradation is inhibitory in phage infection of K1-defective Escherichia coli," J Bacteriol, Dec. 1992; 174(23):7757-61.

Perfetto et al., "Seventeen-colour flow cytometry: unravelling the immune system," Nat Rev Immunol, Aug. 2004; 4(8):648-55.

Pieper et al., "MODBASE, a database of annotated comparative protein structure models, and associated resources," Nucleic Acids Res. Jan. 1, 2004. 32(Database issue):D217-22.

Prien et al., "Differentiating N-linked glycan structural isomers in metastatic and nonmetastatic tumor cells using sequential mass spectrometry," Glycobiology, May 2008; 18(5):353-66. Published online Feb. 6, 2008.

Roederer et al., "8 color, 10-parameter flow cytometry to elucidate complex leukocyte heterogeneity," Cytometry, Dec. 1, 1997; 29(4):328-39.

(56) References Cited

OTHER PUBLICATIONS

Schwartz et al., "Standardizing flow cytometry: construction of a standardized fluorescence calibration plot using matching spectral calibrators," Cytometry, Mar. 15, 1996; 26(1):22-31.
Schwartz et al., "Standardizing flow cytometry: a classification system of fluorescence standards used for flow cytometry," Cytometry, Oct. 1, 1998; 33(2):106-14.
National Center for Biotechnology Information, National Library of Medicine, National Institutes of Health, GenBank-Locus NGLY1_HUMAN, Accession No. Q96IV0, "RecName: Full=Peptide-N(4)-(N-acetyl-beta-glucosaminyl) asparagine amidase; Short=PNGase; Short=hPNGase; AltName: Full=N-glycanase 1; AltName: Full=Peptide:N-glycanase," [online]. Bethesda, MD [retrieved on May 9, 2018]. Retrieved from the Internet: ncbi.nlm.nih.gov/protein/Q96IV0; 8 pgs.
International Application No. PCT/US15/26374, filed Apr. 17, 2015; International Search Report and Written Opinion dated Aug. 10, 2015; 11 pages.
International Application No. PCT/US15/26374, filed Apr. 17, 2015; International Preliminary Report on Patentability dated Oct. 27, 2016; 8 pages.
Ackerman et al., "Highly avid magnetic bead capture: An efficient selection method for de novo protein engineering utilizing yeast surface display," Biotechnology Progress, 2009; 25:774-83.
Adams and Scadden, "The hematopoietic stem cell in its place," Nat Immunol, Apr. 2006; 7(4):333-7.
Ahmad et al. "Human linker histones: interplay between phosphorylation and O-beta-GlcNAc to mediate chromatin structural modifications," Cell Division, Jul. 12, 2011; 6:15.
Alwael et al. "Pipette-tip selective extraction of glycoproteins with lectin modified gold nano-particles on a polymer monolithic phase," Analyst, Jun. 21, 2011; 136(12):2619-28. Epub May 6, 2011.
An et al., "Glycomics and disease markers," Current Opinion in Chemical Biology, Dec. 2009; 13(5-6):601-7. Epub Sep. 21, 2009.
Arnaud et al., "Binding sugars: from natural lectins to synthetic receptors and engineered neolectins," Chem Soc Rev, Jun. 7, 2013; 42(11):4798-813. Epub Jan. 25, 2013.
Asensio et al., "Carbohydrate-Aromatic Interactions," Acc Chem Res, Apr. 16, 2013; 46(4):946-54. Epub Jun. 15, 2012.
Bae et al., "Molecular Basis for the Selectivity and Specificity of Ligand Recognition by the Family 16 Carbohydrate-binding Modules from Thermoanaerobacterium polysaccharolyticum ManA," Journal of Biological Chemistry, May 2, 2008. 283(18):12415-12425.
Baker and Sali, "Protein Structure Prediction and Structural Genomics," Science, Oct. 5, 2001; 294(5540):93-6.
Barakat & Love, "Molecular Diversity in Engineered Protein Libraries," Curr Opin Chem Biol, 2007; 11:335-41.
Belien et al., "Phage display based identification of novel stabilizing mutations in glycosyl hydrolase family 11 B. subtilis endoxylanase XynA," Biochem Biophys Res Commun, Mar. 28, 2008; 368(1):74-80. Epub Jan. 28, 2008.
Benatuil et al., "An improved yeast transformation method for the generation of very large human antibody libraries," Protein Eng Des Sel, Apr. 2010; 23(4):155-9. Epub Feb. 3, 2010.
Benz et al., "Experimental validation of molecular dynamics simulations of lipid bilayers: a new approach," Biophysical Journal, Feb. 2005; 88(2):805-17. Epub Nov. 8, 2004.
Berman et al., "The Protein Data Bank," Nucl Acids Res, Jan. 1, 2000; 28(1):235-42.
Bertozzi et al., "Chemical glycobiology," Mar. 23, 2001, Science, 291(5512):2357-64.
Beveridge et al., "Free energy via molecular simulation: applications to chemical and biomolecular systems," Annu Rev Biophys Biophys Chem, 1989; 18:431-92.
Bonsor, "Dissecting protein-protein interactions using directed evolution," Biochem, Apr. 5, 2011; 50(13):2394-402. Epub Mar. 1, 2011.
Bornscheuer et al., "Survey of protein engineering strategies," Curr Protoc Protein Sci, Nov. 2011; Chapter 26, Unit 26.7.

Brannigan et al., "Protein engineering 20 years on," Nat Rev Mol Cell Biol, Dec. 2002; 3(12):964-70.
Brastad et al., "Optimizing non-natural protein function with directed evolution," Curr Opin Chem Biol, Apr. 2011; 15(2):201-10. Epub Dec. 23, 2010.
Burda et al., "The dolichol pathway of N-linked glycosylation," Biochim Biophys Acta, Jan. 6, 1999; 1426(2):239-57.
Carrascal et al., "Energetic decomposition with the generalized-born and Poisson-Boltzmann solvent models: lessons from association of G-protein components," J Phys Chem B, Apr. 22, 2010; 114(15):5096-116.
Case et al., "The Amber biomolecular simulation programs," J Comput Chem, Dec. 2005; 26(16):1668-88.
Case et al., AMBER 10 User Manual, 2008 [retrieved on Apr. 20, 2018]. Retrieved from the Internet: infoscience.epfl.ch/record/121435/files/Amber10i.pdf; 304 pgs.
Chao et al., "Isolating and engineering human antibodies using yeast surface display," Nat Protocols, 2006; 1(2):755-68.
Chen et al., "An engineered high affinity Fbs1 carbohydrate binding protein for selective capture of N-glycans and N-glycopeptides," Nature Comm. 8; Article No. 15487 (May 23, 2017) doi:10.1038/ncomms15487, 15 pages.
Chica et al., "Semi-rational approaches to engineering enzyme activity: combining the benefits of directed evolution and rational design," Curr Opin Biol, 2005; 16: 378-84.
Chowdhury et al. "Improving Antibody Affinity by Mimicking Somatic Hypermutation in vitro," Nature Biotechnology, Jun. 1999; 17:568-72.
Christ et al., "Basic ingredients of free energy calculations: A review," Journal of Computational Chemistry, Jun. 2010; 31(8):1569-52.
Cobb et al., "Directed evolution: Past, present, and future," AIChE Journal, May 2013; 59(5):1432-40.
Cobucci-Ponzano et al., "Engineering the stability and the activity of a glycoside hydrolase," Protein Eng Des Sel, Jan. 2011; 24(1-2):21-6. Epub Oct. 27, 2010.
Cooper, "Optical biosensors in drug discovery," Nat Rev Drug Discov, Jul. 2002; 1(7): 515-28.
Cummings, "The repertoire of glycan determinants in the human glycome," Mol Biosyst, Oct. 2009; 5(10):1087-104. Epub Jul. 28, 2009.
Cunningham et al., "Glyco-biosensors: Recent advances and applications for the detection of free and bound carbohydrates," Analyst, Oct. 2010; 135(10):2471-80. Epub Aug. 11, 2010.
Cylwik et al., "Congenital disorders of glycosylation. Part II. Defects of protein O-glycosylation," Acta Biochimica Polonica, 2013; 60(3):361-8. Epub Sep. 19, 2013.
Dance, "From pond scum to pharmacy shelf," Nat Med, Feb. 2010; 16(2):146-9.
Debray et al., "Specificity of twelve lectins towards oligosaccharides and glycopeptides related to N-glycosylproteins," Eur J Biochem, Jun. 1981; 117(1):41-55.
DeMarco et al. "Structural glycobiology: a game of snakes and ladders," Glycobiol. 2008; 18:426-40.
De Ruiter et al., "Free energy calculations of protein-ligand interactions," Curr Opin Chem Biol, Aug. 2011; 15(4):547-52. Epub Jun. 22, 2011.
Del Vecchio et al., "Thermodynamic Stability of Ribonuclease B," Journal of Thermal Analysis and Calorimetry, 2000; 61:363-8.
Dreier et al., "Ribosome display: a technology for selecting and evolving proteins from large libraries," Methods Mol Biol, 2011; 687:283-306.
Drickamer et al., "Evolving views of protein glycosylation," Trends Biochem Sci, Sep. 1998; 23(9):321-4.
Dunbrack Jr., "Rotamer libraries in the 21st century," Cur Opin Struct Biol, Aug. 2002; 12(4):431-40.
Fadda et al., "Molecular simulations of carbohydrates and proteincarbohydrate interactions: motivation, issues and prospects," Drug Discov Today, Aug. 2010; 15(15-16):596-609. Epub Jun. 8, 2010.
Fan et al., "Detailed Studies on Substrate Structure Requirements of Glycoamidases A and F," J Biol Chem, Oct. 24, 1997; 272(43):27058-64.

(56) References Cited

OTHER PUBLICATIONS

Feldmeier et al., "Computational protein design of ligand binding and catalysis," Curr Opin Chem Biol, Dec. 2013; 17(6):929-33.

Filitcheva, "PNGases: A diverse family of enzymes related by function rather than catalytic mechanism" Ph D. Thesis, Institute of Mol BioSci, Massey University, Palmerston North, New Zealand, 2010; 340 pages.

Joo Lee et al., "Phage-Display Selection of a Human Single-Chain Fv Antibody Highly Specific for Melanoma and Breast Cancer Cells Using a Chemoenzymatically Synthesized GM3-Carbohydrate Antigen," J. Am. Chem. Soc. 2002. 124:12439-12446. Available online on Sep. 28, 2002.

Kadirvelraj et al., "Understanding the bacterial polysaccharide antigenicity of *Streptococcus agalactiae* versus *Streptococcus pneumoniae*" Proc. Natl. Acad. Sci. USA May 23, 2006. 103:8149-5154. Available online on May 16, 2006.

Karaveg, "Energetics of Substrate Binding and Catalysis by Class 1 (Glycosylhydrolase Family 47)—Mannosidases Involved in N-Glycan Processing and Endoplasmic Reticulum Quality Control." J. Biol. Chem. Jan. 1, 2005. 280(33):29837-29848. Available online on May 23, 2005.

Kortemme and Baker,"A simple physical model for binding energy hot spots in protein-protein complexes," Proc. Natl. Acad. Sci. USA Oct. 29, 2002. 99:14116-14121. Available online on Oct. 15, 2002.

Kraemer-Pecore et al., "Computational protein design," Curr. Opin. Chem. Biol. Dec. 2001. 5:690-695.

Kuhn et al., "Active site and oligosaccharide recognition residues of peptide-N4-(N-acetyl-ß-D-glucosaminyl) asparagine amidase F," J. Biol. Chem. Dec. 8, 1995. 270:29493-29497.

Kumar and Zewail, "Dynamics of water in biological recognition," Chem. Rev. Apr. 2004. 104:2099-2123. Available online on Mar. 27, 2004.

Kumazaki et al., "A novel method for selective isolation of C-terminal peptides from tryptic digests of proteins by immobilized anhydrotrypsin: application to structural analyses of the tail sheath and tube proteins from bacteriophage T4," Proteins Sep. 1986. 1:100-107.

Laitinen et al., "Free energy simulations and MM-PBSA analyses on the affinity and specificity of steroid binding to antiestradiol antibody," Proteins Apr. 1, 2004. 55:34-43.

Liang et al., "Free Energy Simulation Studies of the Binding Specificity of Mannose-Binding Protein," J. Phys. Chem. Feb. 15, 1996 100:2528-2534.

Lienemann et al., "Toward understanding of carbohydrate binding and substrate specificity of a glycosyl hydrolase 18 family (GH-18) chitinase from Trichoderma harzianum." Glycobiology. 2009. 19(10):1116-1126. Available online on Jul. 13, 2009.

Looger et al., "Computational design of receptor and sensor proteins with novel functions," Nature May 8, 2003. 423:185-190.

Mao et al., "Phage-display library selection of high-affinity human single-chain antibodies to tumor-associated carbohydrate antigens sialyl Lewisx and Lewisx," Proc. Natl. Acad. Sci. USA Jun. 8, 1999 96:6953-6958.

Masso et al., "Computational mutagenesis studies of protein structure-function correlations," Proteins Jul. 1, 2006. 64:234-245. Available online on Apr. 14, 2006.

Meier and Duus, "Antibody glycans wiggle and jiggle," Mar. 2011 Nature Chem. Biol. 7:131-132.

Moore and Maranas, "Computational challenges in combinatorial library design for protein engineering," AIChE J. Feb. 2004. 50:262-272. Available online on Feb. 10, 2004.

Moreira et al., "Computational alanine scanning mutagenesis—an improved methodological approach," J. Comp. Chem. Feb. 2007. 28:644-654. Available online on Dec. 28, 2006.

Moreira et al., "Unravelling hot spots: a comprehensive computational mutagenesis study," Theor. Chem. Acc. Jan. 2007. 117:99-113. Available online on Jul. 11, 2006.

Patrick and Firth, "Strategies and computational tools for improving randomized protein libraries," Biomol. Eng. Oct. 2005. 22:105-112.

Pratap et al., "The combination of molecular dynamics with crystallography for elucidating protein-ligand interactions: a case study involving peanut lectin complexes with T-antigen and lactose," Acta Crystallogr. Nov. 2001. D57:1584-1594. Available online on Oct. 25, 2001.

Rajpal et al., "A general method for greatly improving the affinity of antibodies by using combinatorial libraries" Proc Natl Acad Sci U S A, Jun. 14, 2005; 102(24):8466-71. Epub Jun. 6, 2005.

Taniguchi and Paulson, "Frontiers in glycomics; bioinformatics and biomarkers in disease," Proteomics May 7, 2007. 7:1360-1363. Available online on Apr. 13, 2007.

Taroni et al., "Analysis and prediction of carbohydrate binding sites," Prot. Eng. Feb. 2000. 13:89-98.

Tempel et al., "The xenograft antigen bound to Griffonia simplicifolia lectin 1-ß4. X-ray crystal structure of the complex and molecular dynamics characterization of the binding site," J. Biol. Chem. Feb. 22, 2002. 277:6615-6621. Available online on Nov. 19, 2001.

Tian et al., "Structure-based design of robust glucose biosensors using a Thermotoga maritima periplasmic glucose-binding protein," Protein Sci. Oct. 2007. 16:2240-2250. Available online on Aug. 31, 2007.

Treynor et al., "Computationally designed libraries of fluorescent proteins evaluated by preservation and diversity of function" Proc. Natl. Acad. Sci. USA Jan. 2, 2007. 104:48-53. Available online on Dec. 19, 2006.

Voigt et al., "Computationally focusing the directed evolution of proteins," J. Cell. Biochem Suppl. 2001. Suppl 37:58-63.

Woods et al., "GLYCAM_93: A generalized parameter set for molecular dynamics simulations of glycoproteins and oligosaccharides. Application to the structure and dynamics of a disaccharide related to oligomannose," in Complex Carbohydrates in Drug Research. Bock et al. (Eds.). Munksgaard: Copenhagen, Denmark; copyright 1994. pp. 15-26.

Woods et al., "Molecular Mechanical and Molecular Dynamical Simulations of Glycoproteins and Oligosaccharides. 1. GLYCAM_93 Parameter Development," J. Phys. Chem. Mar. 1995. 99:3832-3846.

Woods, Robert J, "High-Specificity Affinity Reagents for N-Glycosylation Site Mapping and Glycomics," Grant Abstract, Grant No. GM086991 [online]. National Institute of General Medical Sciences, National Institutes of Health, project dates Sep. 1, 2009 to Aug. 31, 2011 [retrieved on Jan. 15, 2013]. Retrieved from the Internet: projectreporter.nih.gov/pr_Prj_info_desc_dtls.cfm?aid=7671759&icde=14958299&ddparam=&ddvalue=&ddsub=&cr=1&csb=default&cs=ASC&print=yes; 2 pgs.

Woods, Robert J, "Computational Analysis of Carbohydrate Antigenicity," Grant Abstract, Grant No. GM055230 [online]. National Institute of General Medical Sciences, National Institutes of Health, project dates Mar. 1, 1997 to Apr. 30, 2007 [retrieved on Jan. 15, 2013]. Retrieved from the Internet: projectreporter.nih.gov/or_Prj_info_desc_dtls.cfm?aid=6888359&icde=14958503&ddparam=&ddvalue=&ddsub=&cr=25&csb=default&cs=ASC&print=yes; 2 pgs.

Woods, Robert J, "Integrating Experiment and Theory to Characterize Diagnostic Antibody Specificity," Grant Abstract, Grant No. GM094919 [online]. National Institute of General Medical Sciences, National Institutes of Health, project dates Sep. 1, 2010 to Aug. 31, 2014 [retrieved on Jan. 15, 2013]. Retrieved from the Internet: projectreporter.nih.gov/pr_Prj_info_desc_dtls.cfm?aid=7994664&icde=14958573&ddparam=&ddvalue=&ddsub=&cr=11&csb=default&cs=ASC&print=yes; 2 pgs.

Woods, Robert J, "Conformation of Antigenic Epitopes of C Neoformans Capsular Polysacc: Aids," Grant Abstract, Grant No. 5P41RR005351-10, Subproject 0041 [online]. National Center For Research Resources, National Institutes of Health, project dates Sep. 30, 1998 to Jul. 31, 1999 [retrieved on Jan. 15, 2013]. Retrieved from the Internet: projectreporter.nih.gov/pr_Prj_info_desc_dtls.cfm?aid=6122208&icde=14958683&ddparam=&ddvalue=&ddsub=&cr=99&csb=default&cs=ASC&print=yes; 1 pg.

The Scripps Research Institute (TSRI), "High Throughput Screening (HTS);" 2015. Accessed online on May 18, 2015, via scripps.edu/florida/technologies/hts/, 2 pages.

"LECTENZ" [online]. United States Patent and Trademark Office Trademark Electronic Search System (TESS). Trademark applica-

(56) References Cited

OTHER PUBLICATIONS tion filed on Dec. 26, 2007, and published for opposition on Jul. 7, 2009. Available online [retrieved on Aug. 19, 2011]. Retrieved from the Internet: tess2.uspto.gov/bin/showfield?f=doc&state=4004:787618. 2.1; 2 pgs.
"The Research Group of Professor Robert J. Woods," GLYCAM; The University of Georgia | Complex Carbohydrate Research Center: Athens, GA. Available online [retrieved on Aug. 19, 2011]. Retrieved from the Internet: glycam.ccrc.uga.edu/ccrc/pages/ri.html; 4 pgs.
"Translational Research: merging computational modeling and protein engineering to design biomolecules," Available online [retrieved on Aug. 19, 2011]. Retrieved from the Internet: ksamli.myweb.uga.edu/Research.html; p. 1 of 2.
United States Trademark "LECTENZ"—Reg. No. 4,264,797; registered on Dec. 25, 2012. Published for Opposition on Jul. 7, 2009. Filed Dec. 26, 2007.
Woods, Robert J, "Cryptococcus Neoformans Capsular Polysaccharides Antigenic Epitope Conform: Aids," Grant Abstract, Grant No. 5P41RR005351-09, Subproject 0041 [online]. National Center For Research Resources, National Institutes of Health, project dates Sep. 30, 1997 to Sep. 29, 1998 [retrieved on Sep. 25, 2014]. Retrieved from the Internet: projectreporter.nih.gov/pr_Prj_info_desc_dtls.cfm?aid=6253248&icde=21876699&ddparam=&ddvalue=&ddsub=&cr=100&csb=default&cs=ASC&print=yes; 1 pg.
Woods, Robert J, "Development of Mesoscale Model Simulating Polysaccharide," Grant Abstract, Grant No. 2P41RR005351-16, Subproject 0114 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181452&icde=21876699&ddparam-&ddvalue=&ddsub=&cr=72&csb=default&cs=ASC&print=yes; 1 pg.
Woods, Robert J, "Investigation of Ganglioside Responsible for Enterotoxin," Grant Abstract, Grant No. 2P41RR005351-16, Subproject 0115 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181453&icde=21876699&ddparam=&ddvalue=&ddsub=&cr=73&csb=default&cs=ASC&print=yes; 1 pg.
Woods, Robert J, "Influence of N-Glycosylation on Glycopeptide," Grant Abstract, Grant No. 2P41RR005351-16, Subproject 0116 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181454&icde=21876699&ddparam=&ddvalue=&ddsub=&cr=74&csb=delault&cs=ASC&print=yes; 1 pg.
Freeze, "Update and perspectives on congenital disorders of glycosylation," Glycobiology, Dec. 2001; 11(12):129R-143R.
Fu et al., "A detailed structural characterization of ribonuclease B oligosaccharides by 1H NMR spectroscopy and mass spectrometry," Carbohydr Res, Aug. 17, 1994; 261(2):173-86.
Gasteiger E., H.C., Gattiker A., Duvaud S., Wilkins M.R., Appel R.D., Bairoch A. in The Proteomics Protocols Handbook (ed. J.M. Walker) pp. 571-607 (Copyright Humana Press, 2005).
Genheden et al., "A comparison of different initialization protocols to obtain statistically independent molecular dynamics simulations," J Comput Chem, Jan. 30, 2011; 32(2):187-95.
Genheden et al., "Will molecular dynamics simulations of proteins ever reach equilibrium?" Phys Chem Chem Phys, Jun. 28, 2012; 14(24):8662-77. Epub May 22, 2012.
Gera et al., "Protein selection using yeast surface display," Methods, Mar. 15, 2013; 60(1):15-26. Epub Mar. 23, 2012.
Ghazarian et al., "A glycobiology review: carbohydrates, lectins and implications in cancer therapeutics," Acta Histochem, May 2011; 113(3):236-47. Epub Mar. 2, 2010.
Giancola et al., "Thermodynamic stability of the two isoforms of bovine seminal ribonuclease," Biochemistry, Jul. 11, 2000; 39(27):7964-72.
Goonetilleke et al., "Systematic review of carbohydrate antigen (CA 19-9) as a biochemical marker in the diagnosis of pancreatic cancer," Eur J Surg Oncol, Apr. 2007; 33(3):266-70. Epub Nov. 9, 2006.
Graf et al., "Selective alteration of substrate specificity by replacement of aspartic acid-189 with lysine in the binding pocket of trypsin," Biochemistry, May 5, 1987; 26(9):2616-23.
Groenhof, "Introduction to QM/MM simulations," Methods Mol Biol, 2013; 924:43-66.
Grove, et al., "Creating novel proteins by combining design and selection," Protein Eng Des Sel, 2010; 23:449-455.
Guillén et al., "Carbohydrate-binding domains: multiplicity of biological roles," Appl Microbiol Biotechnol, Feb. 2010; 85(5):1241-9. Epub Nov. 12, 2009.
Guvench et al., "Comparison of protein force fields for molecular dynamics simulations," Methods Mol Biol, 2008; 443:63-88.
Hadden et al., "Calculating binding free energies for protein-carbohydrate complexes," Methods Mol Biol. 2015; 1273:431-65.
Hakomori, "Tumor-associated carbohydrate antigens," Annu Rev Immunol, 1984; 2:103-26.
Haltiwanger and Lowe, "Role of glycosylation in development," Annu Rev Biochem, 2004; 73:491-537.
Hancock et al., "Designer enzymes for glycosphingolipid synthesis by directed evolution," Nat Chem Biol, Jul. 2009; 5(7):508-14.
Harata et al., "Crystal structures of Urtica dioica agglutinin and its complex with tri-N-acetylchitotriose," J Mol Biol, Mar. 31, 2000; 297(3):673-81.
Hart and Copeland, "Glycomics hits the big time," Cell, Nov. 24, 2010; 143(5):672-6.
Haselbeck and Hosel, "Studies on the effect of the incubation conditions, various detergents and protein concentration on the enzymatic activity of Nglycosidase F (Glycopeptidase F) and endoglycosidase F," Topics in Biochemistry, 1988; 8:1-4.
Haseley et al., "Unravelling carbohydrate interactions with Biosensors using surface plasmon resonance (SPR) detection," Topics in Chemistry, 2002; vol. 218:93-114.
Hashimoto et al., "KEGG as a glycome informatics resource," Glycobiology, May 2006; 16(5):63R-70R. Epub Jul. 13, 2005.
Heimburg-Molinaro et al., "Preparation and analysis of glycan microarrays," Curr Protoc Protein Sci, Apr. 2011; Chapter 12:Unit12. 10.
Helenius & Aebi, "Intracellular functions of N-linked glycans," Science, Mar. 23, 2001; 291(5512):2364-9.
Hess et al., "GROMACS 4: Algorithms for Highly Efficient, Load-Balanced, and Scalable Molecular Simulation," J Chem Theory Comput, Mar. 2008; 4(3):435-47.
Hou et al., "Assessing the performance of the MM/PBSA and MM/GBSA methods. 1. The accuracy of binding free energy calculations based on molecular dynamics simulations," J Chem Inf Model, Jan. 24, 2011; 51(1):69-82. Epub Nov. 30, 2010.
Huang et al., "Chemoenzymatic synthesis and lectin array characterization of a class of N-glycan clusters," J Am Chem Soc, Dec. 16, 2009; 131(49):17963-71.
Hummer & Szabo, "Calculation of free-energy differences from computer simulations of initial and final states," J Chem Physics, 1996; 105(5):2004-10.
Hutchison et al., "Mutagenesis at a specific position in a DNA sequence," J Biol Chem, Sep. 25, 1978; 253(18):6551-60.
Isom et al., "Charges in the hydrophobic interior of proteins," Proc Natl Acad Sci USA, Sep. 14, 2010; 107(37):16096-100. Epub Aug. 26, 2010.
Jakeman et al., "A beta-(1,2)-glycosynthase and an attempted selection method for the directed evolution of glycosynthases," Biochemistry, Nov. 29, 2011; 50(47):10359-66. Epub Nov. 3, 2011.
Jakobsson et al., "Endosialidases: Versatile Tools for the Study of Polysialic Acid," Top Curr Chem, 2015; 367:29-73.
Jiang et al., "De novo computational design of retro-aldol enzymes," Science, Mar. 7, 2008; 319(5868):1387-91.

(56) References Cited

OTHER PUBLICATIONS

Joao et al., "Effects of glycosylation on protein conformation and amide proton exchange rates in RNase B," FEBS Lett, Aug. 3, 1992; 307(3):343-6.
Jokilammi et al. "Construction of antibody mimics from a noncatalytic enzyme-detection of polysialic acid," J Immunol Meth, 2004; 295:149-160.
Jorgensen, "The many roles of computation in drug discovery," Science, Mar. 19, 2004; 303(5665):1813-8.
Jorgensen, "Efficient Drug Lead Discovery and Optimization," Acc Chem Res, Jun. 16, 2009; 42(6):724-33.
Jung & Cho, "Serial affinity chromatography as a selection tool in glycoproteomics," Anal Chem, Aug. 6, 2013; 85(15):7125-32. Epub Jul. 10, 2013.
Karanicolas et al., "A De Novo Protein Binding Pair By Computational Design and Directed Evolution," Mol Cell, Apr. 22, 2011; 42(2):250-60. Epub Mar. 31, 2011.
Karaveg et al. "Energetics of Substrate Binding and Catalysis by Class 1 (GLycosylhydrolase Family 47)—Mannosidases Involved in N-Glycan Processing and Endoplasmic Reticulum Quality Control," J Biol Chem, 2005; 280(33):29837-48.
Karplus & McCammon, "Molecular dynamics simulations of biomolecules," Nat Struct Biol, Sep. 2002; 9(9):646-52.
Karplus and Kuriyan, "Molecular dynamics and protein function," Proc Natl Acad Sci USA, May 10, 2005; 102(19):6679-85. Epub May 3, 2005.
Kenrick and Daugherty, "Bacterial display enables efficient and quantitative peptide affinity maturation," Protein Eng Des Sel, 2010; 23:9-17.
Kittl and Withers, "New approaches to enzymatic glycoside synthesis through directed evolution," Carbohydr Res, Jul. 2, 2010; 345(10):1272-9. Epub Apr. 9, 2010.
Knauer and Lehle, "The oligosaccharyltransferase complex from yeast," Biochim Biophys Acta, Jan. 6, 1999; 1426(2):259-73.
Korecka et al. "Bioaffinity magnetic reactor for peptide digestion followed by analysis using bottom-up shotgun proteomics strategy," J Sep Sci, Feb. 2008; 31(3):507-15.
Kornfeld & Kornfeld, "Assembly of asparagine-linked oligosaccharides," Annu Rev Biochem, 1985; 54:631-64.
Woods, Robert J, "Application of Glycam in Generation of Energy Surfaces," Grant Abstract, Grant No. 2P41RR005351-16, Subproject 0145 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181463&icde=2187.
Woods, Robert J, "Peptide Mimics of Group B *Streptococcal* Antigens," Grant Abstract, Grant No. 2P41RR005351-16, Subproject 0146 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181464&icde=2187.
Woods, Robert J, "Combined Theoretical MD & Experimental NMR Analysis," Grant Abstract, Grant No. 2P41RR005351-16, Subproject 0152 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181465&icde=2187.
Woods, Robert J, "Synergistic Theoretical & Experimen Approach," Grant Abstract, Grant No. 2P41RR005351-16, Subproject 0153 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181466&icde=2187.
Woods, Robert J, "Conformational Analysis of Mannosidase Inhibitors," Grant Abstract, Grant No. 2P41RR005351-16, Subproject 0157 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181470&icde=2187.
Woods, Robert J, "Carbohydraie Mimicry by Peptide Mimotopes," Grant Abstract, Grant No. 2P41RR005351-16, Subproject 0160 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181477&icde=2187.
Woods, Robert J, "Glycoprotein Structure /Protein-Carbohydrate Interaction," Grant Abstract, Grant No. 2P41RR005351-16, Subproject 0161 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181478&icde=2187.
Woods, Robert J, "Selective Inhibition of Golgi Alpha-Mannosidase II," Grant Abstract, Grant No. 2P41RR005351-16, Subproject 0162 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181479&icde=2187.
Woods, Robert J, "Molecular Modeling," Grant Abstract, Grant No. 2P41RR005351-16, subproject 0169 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181488&icde=21876699&ddparam=&ddvalue=&ddsub=&cr=87&csb=default&cs=ASC&print=yes; 1 pg.
Woods, Robert J, "Modeling Transcriptional Pre-Inhibition Complex," Grant Abstract, Grant No. 2P41RR005351-16, Subproject 0180 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181499&icde=2187.
International PCT Application No. PCT/2012/027211, filed Mar. 1, 2012; International Search Report and Written Opinion dated Nov. 7, 2012; 11 pages.
International PCT Application No. PCT/2012/027211, filed Mar. 1, 2012; International Preliminary Report on Patentability dated Sep. 12, 2013; 7 pages.
National Center for Biotechnology Information, National Library of Medicine, National Institutes of Health, GenBank Locus NANL_MACDE, Accession No. Q27701, "RecName: Full=Anhydrosialidase; AltName: Full=Anhydroneuraminidase; AltName: Full=Sialidase L; Flags: Precursor" [online]. Bethesda, MD [retrieved on Nov. 2, 2016]. Retrieved from the Internet: URL: ncbi.nlm.nih.gov/protein/q27701; 9 pgs.
Aalto et al., "Mutant bacteriophage with non-catalytic endosialidase binds to both bacterial and eukaryotic polysialic acid and can be used as probe for its detection," Glycoconj J; 2001 18:751-758.
Abbott et al., "Targeted glycoproteomic identification of biomarkers for human breast carcinoma," J Proteome Res, 2008; 7(4):1470-80.
Abbott and Pierce, "Lectin-based glycoproteomic techniques for the enrichment and identification of potential biomarkers," 2010 Meth Enzymol; 480:461-476.
Affymetrix, "Procarta Cytokine Assay User Manual (Polystyrene Beads/ Filter Plate)" Apr. 6, 2011; Santa Clara, CA. 31 pages.
Amnis Corporation, "The Image Stream, Imagine Flow Cytometer" Brochure, Seattle, WA, 2012; 16 pages. URL: amnis.com/documents/brochures/ImageStreamx_brochure.pdf.
Amore and Coppo, "Modulation of mesangial cell reactivity by aberrantly glycosylated IgA" Nephron, Nov. 2000; 86(3):255-9.
Arnold et al., "The impact of glycosylation on the biological function and structure of human immunoglobulins," Ann Rev Immunol, 2007; 25:21-50.
Barakat et al., "Exploiting Elements of Transcriptional Machinery to Enhance Protein Stability," J Mol Biol, 2007; 366:103-116.
Bechtel et al., "Conformational analysis of the tumor-associated carbohydrate antigen 19-9 and its Lea blood group antigen component as related to the specificity of monoclonal antibody CO19-9," J Biol Chem, Feb. 5, 1990; 265(4):2028-37.
Birtwell and Morgan, "Microparticle encoding technologies for high-throughput multiplexed suspension assays," Integr Biol (Camb), Jun. 2009; 1(5-6):345-62.

(56) References Cited

OTHER PUBLICATIONS

Block et al., "Use of targeted glycoproteomics to identify serum glycoproteins that correlate with liver cancer in woodchucks and humans," Proc Natl Acad Sci USA, Jan. 18, 2005; 102(3):779-84.
Bouckaert et al., "The crystal structures of Man(a1-3)Man(a1-O)Me and Man(a1-6)Man(a1-O)Me in complex with concanavalin A," J Bio Chem, Oct. 8, 1999; 274(41):29188-95.
Braekmans et al., "Encoding Microcarriers: Present and Future Technologies," Nat Rev Drug Discovery, Jun. 2002; 1(6):447-56.
Camilla et al., "Flow cytometric microsphere-based immunoassay: analysis of secreted cytokines in whole-blood samples from asthmatics," Clin Diagn Lab Immunol, Jul. 2001; 8(4):776-84.
Cantarel et al., "The Carbohydrate-Active EnZymes database (CAZy): an expert resource for Glycogenomics," Nucleic Acids Res, Jan. 2009; 37(Database Issue):D233-8. Published online Oct. 5, 2008.
Carson and Vignali, "Simultaneous quantitation of 15 cytokines using a multiplexed flow cytometric assay," J Immunol Methods, Jul. 30, 1999; 227(1-2):41-52.
Chandrasekaran et al., "Biosynthesis of the carbohydrate antigenic determinants, Globo H, blood group H, and Lewis b: a role for prostate cancer cell alpha1,2-L-fucosyltransferase," Glycobiology, Mar. 2002; 12(3):153-62.
Charles River Research Animal Diagnostic Services, "Multiplexed Fluorometric ImmunoAssay" Product Sheet, Sep. 2007; Wilmington, MA. 5 pages.
Charles River Research Animal Diagnostic Services, "Serologic Methods Manual: Multiplexed Fluorometric ImmunoAssay (MFIA)" Manual, Sep. 9, 2011; Wilmington, MA. 32 pages.
Chipot and Kollman, "Alternative Approaches to Potential of Mean Force Calculations: Free Energy Perturbation versus Thermodynamic Integration Case Study of Some Representative Nonpolar Interactions," J Comput Chem, 1996; 17(9):1112-1131.
Comer et al., "Characterization of a mouse monoclonal antibody specific for O-linked N-acetylglucosamine," Anal Biochem, Jun. 15, 2001; 293(2):169-77.
Consortium for Functional Glycomics, "CFG—Functional Glycomics Gateway" Screen Shot of Home Page, Dr. Richard Cummings, Beth Israel Deaconess Medical Center, Harvard Medical School, Boston, MA, Copyright 2010. [Retrieved on Nov. 12, 2016]. Retrieved from the Internet: functionalglycomics.org/; 2 pages.
Coppo and Amore, "Aberrant glycosylation in IgA nephropathy (IgAN)," Kidney Int, May 2004; 65(5):1544-7.
Davidson et al., "Carbohydrate antigen expression in primary tumors, metastatic lesions, and serous effusions from patients diagnosed with epithelial ovarian carcinoma: evidence of up-regulated Tn and Sialyl Tn antigen expression in effusions," Hum Pathol, Sep. 2000; 31(9):1081-7.
DeMarco et al., "Molecular Characterization of Flu-Receptor—Hemagglutinin Interactions. Computational Prediction of HA Specificity," Presented at Conference Titled Immunobiology of Influenza Virus Infection: Approaches for an Emerging Zoonotic Disease. Athens, GA, Jul. 29-31, 2007, 1 pg.
De Rosa et al., "11-color, 13-parameter flow cytometry: identification of human naive T cells by phenotype, function, and T-cell receptor diversity," Nat Med, Feb. 2001; 7(2):245-8.
Dennis et al., "Structure and mechanism of a bacterial ß-glucosaminidase having O-GlcNAcase activity," Nat Struct Mol Biol, Apr. 2006. 13(4):365-71. Available online on Mar. 26, 2006.
Enzo Life Sciences, "MultiBead Multiplex Assays" Product Flyer, International Edition, May 3, 2011; Plymouth Meeting, PA. 2 pgs.
Fry et al., "Lectin microarray profiling of metastatic breast cancers," Glycobiol, Aug. 2011; 21(8):1060-70. Published online Apr. 19, 2011.
Fulton et al., "Advanced multiplexed analysis with the FlowMetrix system," Clin Chem, Sep. 1997; 43(9):1749-56.
Galab Technologies, "AffiSep Lectin Columns and Kits" informational webpage. Geesthacht, Germany. [retrieved on Jan. 27, 2012]. Retrieved from the Internet: galab.de/technologies/products/hplc. html; 3 pages.
Galab Technologies, "Biotinylated Lectins: Benefits" informational webpage. Geesthacht, Germany. [retrieved on Jan. 27, 2012]. Retrieved from the Internet: galab.de/technologies/products/biotinylated_lectins. html; 1 page.
Galab Technologies, "GlycoCleave—Immobilized Enzymes for Glycoanalysis" informational webpage. Geesthacht, Germany. [retrieved on Jan. 27, 2012]. Retrieved from the Internet: galab.de/technologies/products/immobilized_enzymes.html; 2 pages.
Galab Technologies, "GlycoImage Lectin Array for Glycan Profiling" informational webpage. Geesthacht, Germany.[retrieved on Jan. 27, 2012]. Retrieved from the Internet: galab.de/technologies/products/glycoimage_lectin.html; 2 pages.
Galab Technologies, "Glycoprotein Microplates: Benefits" informational webpage. Geesthacht, Germany. [retrieved on Jan. 27, 2012]. Retrieved from the Internet: galab.de/technologies/products/glycoprotein_microplates.html; 1 page.
Galab Technologies, "Lectin Microplates: Benefits" informational webpage. Geesthacht, Germany. [retrieved on Jan. 27, 2012]. Retrieved from the Internet: galab.de/technologies/products/lectin_microplates. html; 2 pages.
Weatherly et al., "A Heuristic method for assigning a false-discovery rate for protein identifications from Mascot database search results," Mol Cell Proteomics, Jun. 2005; 4(6):762-72. Epub Feb. 9, 2005.
Weerapana et al., "Asparagine-linked protein glycosylation: from eukaryotic to prokaryotic systems," Glycobiology, 2006; 16(6):91R-101R.
White et al., "Genome sequence of the radioresistant bacterium Deinococcus radiodurans R1," Science, Nov. 19, 1999; 286(5444):1571-7.
Wijma & Janssen, "Computational design gains momentum in enzyme catalysis engineering," Febs J, Jul. 2013; 280(13):2948-60. Epub Jun. 3, 2013.
Wijma et al., "Computationally designed libraries for rapid enzyme stabilization," Protein Eng Des Sel, Feb. 2014; 27(2):49-58. Epub Jan. 8, 2014.
Willard and Siderovski, "Covalent immobilization of histidine-tagged proteins for surface plasmon resonance," Anal Biochem, Jun. 1, 2006; 353(1):147-9. Epub Feb. 23, 2006.
Winter et al., "Redesigning enzyme structure by site-directed mutagenesis: tyrosyl tRNA synthetase and ATP binding," Nature, Oct. 21, 1982; 299(5885):756-8.
Woods, "Glycoprotein Structure /Protein-Carbohydrate Interaction," Grant Abstract, Grant No. 2P41RR005351-16, Subproject 0161 [online]. National Center For Research Resources, National Institutes of Health, project dates Apr. 4, 2005 to Jan. 31, 2006 [retrieved on Sep. 25, 2014]. Retrieved from the Internet: projectreporter. nih.gov/pr Prj_ info_ desc dtls.cfm ?aid=7181478&icde=21876699 &ddparam=&ddvalue=&ddsub=&cr=85&csb=default&cs= ASC &print=yes; 1 pg.
Woods, "High-Specificity Affinity Reagents N-Glycosylation Site Mapping and Glycomics," Grant Abstract, Grant No. GM086991 [online]. National Institute of General Medical Sciences, National Institutes of Health, project dates Sep. 1, 2009 to Aug. 31, 2011 [retrieved on Jan. 15, 2013]. Retrieved from the Internet: projectreporter. nih.gov/pr_Prj_info_desc_dtls.cfm?aid=7671759&icde= 149582998ddparam=&ddvalue=&ddsub=&cr=1&csb=default&cs= ASC&print=yes; 2pgs.
Woods et al., "Molecular Mechanical and Molecular Dynamic Simulations of Glycoproteins and Oligosaccharides. 1. GLYCAM_ 93 Parameter Development," J Phys Chem, Mar. 1995; 99(11):3832-46.
Woods & Tessier, "Computational glycoscience: characterizing the spatial and temporal properties of glycans and glycan-protein complexes," Curr Opin Struct Biol, Oct. 2010; 20(5):575-83. Epub Aug. 12, 2010.
Wright, "2.2 A resolution structure analysis of two refined N-acetylneuraminyl-lactose-wheat germ agglutinin isolectin complexes," J Mol Biol, Oct. 20, 1990; 215(4):635-51.
Yip et al., "Directed evolution combined with rational design increases activity of GpdQ toward a non-physiological substrate and alters the oligomeric structure of the enzyme," Protein Eng Des Sel, Dec. 2011; 24(12):861-72. Epub Oct. 6, 2011.

(56) References Cited

OTHER PUBLICATIONS

Yu et al., "Phage display screening against a set of targets to establish peptidebased sugar mimetics and molecular docking to predict binding site," Bioorg Med Chem, Jul. 1, 2009; 17(13):4825-32. Epub Apr. 1, 2009.

Zauner et al., "Protein glycosylation analysis by HILIC-LC-MS of Proteinase K-generated N- and O-glycopeptides," J Sep Sci, Mar. 2010; 33(6-7):903-10.

Zhang et al., "UniPep—a database for human N-linked glycosites: a resource for biomarker discovery," Genome Biol, 2006; 7(8):R73. Epub Aug. 10, 2006.

Zhang et al., "Modification of histones by sugar beta-N-acetylglucosamine (GlcNAc) occurs on multiple residues, including histone H3 serine 10, and is cell cycle-regulated," J Biol Chem, Oct. 28, 2011; 286(43):37483-95. Epub Sep. 6, 2011.

Zhao et al., "Structural and mutational studies on the importance of oligosaccharide binding for the activity of yeast PNGase," Glycobiology, Feb. 2009; 19(2):118-25. Epub Oct. 14, 2008.

Zoete et al., "MM-GBSA binding free energy decomposition and T cell receptor engineering," J Mol Recognit, Mar.-Apr. 2010; 23(2):142-52.

Ahmad, N., et al., Thermodynamic binding studies of bivalent oligosaccharides to galectin-1, galectin-3, and the carbohydrate recognition domain of galectin-3, Glycobiology, 2004; 14(9): 817-25.

Ambrosi, M., N.R. Cameron, and B.G. Davis, Lectins: tools for the molecular understanding of the glycocode, Org Biomol Chem, 2005; 3(9): 1593-608.

Apweiler et al., "On the frequency of protein glycosylation, as deduced from analysis of the SWISS-PROT database," Biochim Biophys Acta, 1999; 1473(1): 4-8.

Archontis et al., Binding Free Energies and Free Energy Components from Molecular Dynamics and Poisson-Boltzmann Calculations. Application to Amino Acid Recognition by Aspartyl-tRNA Synthetase, J Mol Biol, 2001; 306:306-327.

Auchincloss et al., Xenogeneic Transplantation, AnnuRev Immunol, 1998; 16:433-70.

Baker, C.J. and M.S. Edwards, Group B Streptococcal Conjugate Vaccines, Arch Dis Child, 2002; 88: 375-378.

Beutler, E., W. Kuhl, and D. Comings, Hexosaminidase isozyme in type O Gm2 gangliosidosis (Sandho.ff-Jatzkewitz disease), Am J Hum Genet, 1975; 27(5): 628-38.

Bhavanandan, V. and A.W. Katlie, The Interaction of Wheat Germ Agglutinin with Sialoglycoproteins, J Biol Chem, 1979; 254(10): 4000-4008.

Bhogal, N. and R. Combes, TGNJ412: Time to Change the Paradigm for the Testing of New Pharmaceuticals, ATLA, 2006; 34: 225-239.

Blixt et al., Printed Covalent Glycan Array for Ligand Profiling of Diverse Glycan Binding Proteins, Proc Natl Acad Sci USA, 2004; 101: 17033-17038.

Bosques et al., "Effects of Glycosylation on Peptide Conformation: A Synergistic Experimental and Computational Study," J Am Chem Soc, 2004; 126:8421-5.

Bundle et al., Molecular Recognition of a *Salmonella* Trisaccharide Epitope by Monoclonal Antibody Sel55-4, Biochemistry, 1994; 33: 5172-5182.

Buskas et al., Towards a fully synthetic carbohydrate-based anti-cancer vaccine: Synthesis and immunological evaluation of a lipidated glycopeptide containing the tumor-associated Tn antigen, Angewandte Chemie-International Edition, 2005; 44(37): 5985-5988.

Cambi, A. and C.G. Figdor, Levels of complexity in pathogen recognition by C-type lectins, Curr Opin Immunol, 2005; 17(4): 345-51.

Campbell, B.J., L.G. Yu, and J.M. Rhodes, Altered glycosylation in inflammatory bowel disease: A possible role in cancer development, Glycoconjugate Journal, 2001; 18(11-12): 851-858.

Chauhan, D., et al., A novel carbohydrate-based therapeutic GCS-100 overcomes bortezomib resistance and enhances dexamethasone-induced apoptosis in multiple myeloma cells, Cancer Res, 2005; 65(18): 8350-8.

Chervenak, M.C. and E.J. Toone, A Direct Measure of the Contribution of Solvent Reorganization to the Enthalpy of Ligand Binding, J Am Chem Soc, 1994; 116:10533-10539.

Chervenak, M.C. and E.J. Toone, Calorimetric Analysis of the Binding of Lectins with Overlapping Carbohydrate-Binding Ligand Specificities, Biochemistry, 1995; 34:5685-5695.

Chong et al., Molecular Dynamics and Free-Energy Calculations Applied to Affinity Maturation in Antibody 48G7, PNAS, 1999; 96(25): 14330-35.

Clarke, C., et al., The Involvement of Water in Carbohydrate-Protein Binding, J Am Chem Soc, 2001; 123: 12238-12247.

Cornell et al., A Second Generation Force Field for the Simulation of Proteins, Nucleic Acids, and Organic Molecules, J Am Chem Soc, 1995; 117:5179-97.

Corzana, F., et al., A Hydration Study of (1~>4) and (1~>6) linked a-Glucans by Comparative 10 ns Molecular Dynamics Sumulations and 200-MHz NMR, J Comput Chem, 2004; 25: 573-586.

Cunto-Amesty, G., et al., Strategies in Cancer Vaccines Development, International Journal for Parasitology, 2003; 33: 597-613.

Dam, T.K., et al., Thermodynamic Binding Parameters of Individual Epitopes of Multivalent Carbohydrates to Concanavalin A As Determined by "Reverse" Isothermal Titration Microcalorimetry, Biochemistry, 2002; 41: 1359-1363.

Dam, T.K., et al., Thermodynamic Binding Studies of Lectins from the Diocleinae Subtribe to Deoxy Analogs of the Core Trimannoside of Asparagine-Linked Oligosaccharides, J Biol Chem, 2000; 275(21): 16119-16126.

Darden et al., Particle Mesh Ewald: An N Log(N) Method for Ewald Sums in Large Systems, J Chem Phys, 1993; 98:10089.

Develasco, E.A., et al., Protein-Conjugated Synthetic Disaccharide and Trisaccharide of Pneumococcal Type 17/ Exhibit a Different Immunogenicity and Antigenicity Than Tetrasaccharide, Vaccine, 1993; 11(14): 1429-1436.

Delves et al., Roitt's Essential Immunology, 11th Edition, 2006; Title page, Publisher's page, and Table of Contents.

Dong, D.L. and G.W. Hart, Purification and characterization of an O-GlcNAc selective N-acetyl-beta-D-glycosaminidase from rat spleen cytosol, J Biol Chem, 1994; 269(30): 19321-30.

Dorfmueller et al., GlcNAcstatin: a picomolar, selective O-GlcNAcase inhibitor that modulates intracellular O-glcNAcylation levels, J Am Chem Soc, 2006; 128(51):16484-5.

Tschampel et al., "TIP5P-Consistent Treatment of Electrostatics for Biomolecular Simulations," J Chem Theory Comput, 2007; 3:1721-33.

Uematsu et al., High throughput quantitative glycomics and glycoform-focused proteomics of murine dermis and epidermis, Mol Cell Proteomics, 2005; 4(12): 1977-89.

Van Gunsteren et al., Algorithms for Macromolecular Dynamics and Constraint Dynamics, Mol Phys, 1977; 34: 1311-1327.

Van Santen, Y., et al., 1.68 A Crystal Structure of Endopolygalacturonase 11 from Aspergillus niger and Identification of Active Site Residues by Site-directed Mutagenesis, Journal of Biological Chemistry, 1999; 274(43): 30474-30480.

Varki, A., Biological Roles of Oligosaccharides: All of the Theories are Correct, Glycobiology, 1993; 3: 97-130.

Vliegenhart, J.F.G. and R.J. Woods, eds. NMR Spectroscopy and Computer Modeling of Carbohydrates. Recent Advances. ACS Symposium Series. 2006, American Chemical Society: Washington.

Veriet, Computer "Experiments" on Classical Fluids. I. Thermodynamical Properties of Lennard-Jones Molecules, Phys Rev, 1967; 159: 98-103.

Vliegenthart, J.F., Carbohydrate based vaccines, FEBS Lett, 2006; 580(12): 2945-50.

Vocadlo, D.J., et al., A chemical approach for identifying O-GlcNAc-modified proteins in cells, Proc Natl Acad Sci USA, 2003; 100(16): 9116-21.

(56) References Cited

OTHER PUBLICATIONS

Vyas et al., Preliminary Crystallographic Analysis of a Fab Specific for the 0-Antigen of Shigella Flexneri Cell Surface Lipopolysaccharide with and without Bound Saccharides, J Mol Biol, 1993; 231: 133-136.

Walgren et al., High glucose and insulin promote O-GlcNAc modification of proteins, including alpha-tubulin, Am J Physiol Endocrinol Metab, 2003; 284(2):E424-34.

Wang et al., How Well Does a Restrained Electrostatic Potential (RESP) Model Perform in Calculating Conformational Energies of Organic and Biological Molecules?, J Comput Chem, 2000; 21(12):1049-74.

Wells et al., A Yin-Yang complex: O-GlcNAc trans/erase is in a complex with a protein serine/threonine phosphatase, Molecular Biology of the Cell, 1999; 10:192a.

Wells, L., et al., Dynamic O-glycosylation of nuclear and cytoso/ic proteins: further characterization of the nucleocytoplasmic beta-N-acetylglucosaminidase, O-GlcNAcase, J Biol Chem, 2002; 277(3):1755-61.

Wells, L., et al., Mapping sites of O-GlcNAc modification using affinity tags for serine and threonine post-translational modifications, Mol Cell Proteomics, 2002; 1(10):791-804.

Wells, L. and G.W. Hart, O-GlcNAc turns twenty: functional implications for posttranslational modification of nuclear and cytosolic proteins with a sugar, FEBS Lett, 2003; 546(1): 154-8.

Wells et al., O-GlcNAc: a Regulatory Post-Translational Modification, Biochemical and Biophysical Research Communications, 2003; 302:435-441.

West et al., Cytoplasmic glycosylation of protein-hydroxyproline and its relationship to other glycosylation pathways, Biochim Biophys Acta, 2004; 1673(1-2):29-44.

Woods et al., Protein Surface Oligosaccharides and Protein Function, Nature Struct Biol, 1994. 1:499-501.

Woods, Carbohydrate Force Fields, in Encyclopedia of Computational Chemistry, Kollman et al., Ed., John Wiley and Sons: New York. 1998; 220-33.

Xu, Y.F., et al., Tumor-associated carbohydrate antigens: A possible avenue for cancer prevention, Immunology and Cell Biology, 2005. 83(4): 440-448.

Zachara, N.E. and G.W. Hart, 0-GlcNAc a sensor of cellular state: the role of nucleocytoplasmic glycosylation in modulating cellular function in response to nutrition and stress, Biochim Biophys Acta, 2004. 1673(1-2):13-28.

Zdanov et al., Structure of a Single-Chain Antibody Variable Domain (Fv) Fragment Complexed with a Carbohydrate Antigen a 1. 7-A Resolution, Proc Natl Acad Sci USA, 1994; 91:6423-6427.

Zhou et al., Expression, purification, crystallization and preliminary X-ray characterization of the GRP carbohydrate-recognition domain from *Homo sapiens*, Acta Crystallogr Sect F Struct Biol Cryst Commun, 2006; 62(Pt 5):474-6.

Zhu, Leber, and Andrews, Cytoplasmic O-glycosylation prevents cell surface transport of E-cadherin during apoptosis, Embo J, 2001; 20(21):5999-6007.

Porotto et al., "Influence of the Human Parainfluenza Virus 3 Attachment Protein's Neuraminidase Activity on Its Capacity To Activate the Fusion Protein" J Virol, Feb. 2005; 79(4):2383-2392.

Jokilammi et al., "Generation of Lectins from Enzymes: Use of Inactive Endosialidase for Polysialic Acid Detection" Chapter 16 in Lectins: Analytical Technologies edited by Carol L Nilsson. pp. 385-395 (2007).

Yang et al. "High-specificity affinity reagents for N-glycosylation site mapping and glycomics", Glycocojugate J. 26: 877 (Year:2009).

International Search Report and Written Opinion dated Feb. 23, 2010, in connection with PCT/US2009/067582, filed on Dec. 10, 2009.

International Preliminary Report on Patentability dated Jun. 23, 2011, in connection with PCT/US2009/067582, filed on Dec. 10, 2009.

Barakat et al., "Molecular diversity in engineered protein libraries," Curr. Opin. Chem. Biol. Jun. 2007. 11:335-341. Available online on Jun. 4, 2007.

Bradbrook et al., "X-Ray and molecular dynamics studies of concanavalin-A glucoside and mannoside complexes," J. Chem. Soc. Faraday Trans. 1998 94:1603-1611.

Brockmann et al., "Selecting for antibody scFv fragments with improved stability using phage display with denaturation under reducing conditions," J. Immunol. Methods Jan. 2005. 269:159-170. Available online on Dec. 2, 2004.

Bryce et al., "Carbohydrate-protein recognition: molecular dynamics simulations and free energy analysis of oligosaccharide binding to concanavalin A," Biophys. J. Sep. 2001. 81:1373-1388.

Chakrabarti et al., "Computational prediction of native protein ligand-binding and enzyme active site sequences," Proc. Natl. Acad. Sci. USA Jul. 19, 2005. 102:10153-10158. Available online on Jul. 5, 2005.

Chowdhury et al., "Improving antibody affinity by mimicking somatic hypermutation in vitro" Nat Biotechnol, Jun. 1999; 17(6):568-72.

Clark et al., "Affinity enhancement of an in vivo matured therapeutic antibody using structure-based computational design," Protein Sci. May 2006. 15:949-960. Available online on Apr. 5, 2006.

Colombo et al., "Towards the understanding of the structure and dynamics of protein-carbohydrate interactions: molecular dynamics studies of the complexes between hevein and oligosaccharidic ligands," Carbohydr. Res. Apr. 2, 2004. 339:985-994.

Cummings and Esko, "Principles of Glycan Recognition," in Essentials of Glycobiology. 2nd edition. Varki et al., (Eds.) Cold Spring Harbor (NY): Cold Spring Harbor Laboratory Press; 2009. Chapter 27. Available online: ncbi.nlm.nih.gov/books/NBK1950/#_ncbi_dlg_citbx_NBK1950; 16 pages.

DeMarco and Woods, "Structural glycobiology: a game of snakes and ladders," Jun. 2008 Glycobiology 18:426-440. Available online on Apr. 4, 2008.

Deng et al., "Selection of antibody single-chain variable fragments with improved carbohydrate binding by phage display" J. Biol. Chem. Apr. 1, 1994. 269:9533-9538.

Drickamer, "Engineering galactose-binding activity into a C-type mannose-binding protein" Nature Nov. 12, 1992. 360:183-186.

Ducros et al., "Substrate distortion by ß-mannanase: snapshots of the Michaelis and covalent-intermediate complexes suggest a B2,5 conformation for the transition state," Angew. Chem. Int. Ed. Engl. Aug. 2, 2002. 41:2824-2827.

Feldhaus et al., "Yeast display of antibody fragments: a discovery and characterization platform," J. Immun. Methods Jul. 2004. 290:69-80. Available online on May 31, 2004.

Ford et al., "Molecular dynamics simulations of galectin-1-oligosaccharide complexes reveal the molecular basis for ligand diversity" Proteins Nov. 1, 2003. 53:229-240. Available online on Sep. 4, 2003.

Hardt and Laine, "Mutation of active site residues in the chitin-binding domain ChBDChiAI from chitinase A1 of Bacillus circulans alters substrate specificity: use of a green fluorescent protein binding assay," Arch. Biochem. Biophys. Jun. 15, 2004. 426:286-297. Available online on May 6, 2004.

Hastings, "UGA researcher receives NIH award for high-risk, high-reward carbohydrate research; tools will help develop new ways to diagnose and treat host of diseases," UGA Research News Sep. 27, 2010; available online [retrieved on Aug. 19, 2011]. Available on the Internet: ovpr.uga/news/article/20100927-glycan; 2 pages.

Huo et al., "Computational alanine scanning of the 1:1 human growth hormone-receptor complex," J. Comp. Chem. Jan. 15, 2002. 23:15-27. Available online on Nov. 14, 2001.

Imberty, "Oligosaccharide structure: theory versus experiment," 1997 Curr Opin. Structural Biol. 7:617-623.

Jokilammi et al., "Construction of antibody mimics from a noncatalytic enzyme-detection of polysialic acid," J. Immunol. Meth. 2004 295:149-160. Available online on Nov. 14, 2004.

Dreitlein, W.B., J. Maratos, and J. Brocavich, Zanamivir and oseltamivir: Two new options for the treatment and prevention of influenza, Clinical Therapeutics, 2001; 23(3):327-355.

(56) References Cited

OTHER PUBLICATIONS

Dwek, R.A., Glycobiology: Toward Understanding the Function of Sugars, Chem Rev, 1996; 96: 683-720.

Eklund, R. and G. Widwalm, Molecular Dynamics Simulations of an Oligosaccharide Using a Force Field Modified for Carbohydrates, Carbohydrate Research, 2003; 338:393-398.

Elking et al., "Gaussian Induced Dipole Polazization Model," J Comput Chem, 2007; 28(7):1261-74.

Evans et al., Evidence for the Extended Helical Nature of Polysaccharide Epitopes. The 2.8 A Resolution Structure and Thermodynamics of Ligand Binding of an Antigen Binding Fragment Specific for a-(2-8)-Polysialic Acid, Biochemistry, 1995; 34: 6737-6744.

Feinberg, H., et al., Structural basis for selective recognition of oligosaccharides by DC-SIGN and DC-SIGNR, Science, 2001; 294(5549): 2163-6.

Feldhaus et al., Flow-cytometric isolation of human antibodies from a nonimmune *Saccharomyces cerevisiae* surface display library, Nat Biotechnol, 2003; 21(2): 163-70.

Freeze, H.H., Update and perspectives on congenital disorders of glycosylation, Glycobiology, 2001; 11(12): 129r-143r.

Fukuda, M., Possible roles of tumor-associated carbohydrate antigens, Cancer Research, 1996; 56(10): 2237-2244.

Garcia-Hernandez, E., et al., Stereochemical Metrics of Lectin-Carbohydrate Interactions: Comparison with Protein-Protein Interfaces, Glycobiology, 2000; 10(10):993-1000.

Gonzalez-Outeirino, J., et al., Reconciling Solvent Effects on Rotamer Populations in Carbohydrates: a Joint MD and NMR Analysis, Can J Chem, 2006; 84: 569-579.

Gonzalez-Outerino, J., R. Kadirvelraj, and R.J. Woods, Structural Elucidation of Type III Group B *Streptococcus* Capsular Polysaccharide Using Molecular Dynamics Simulations: The Role of Sialic Acid, Carbohydr, Res, 2005; 340: 1007-1018.

Gouda et al., Free Energy Calculations for Theophylline Binding to an RNA Aptamer: Comparison of MM-PBSA and Thermodynamic Integration Methods, Biopolymers, 2003; 68: 16-34.

Grabowski, G.A. and R.J. Hopkin, Enzyme therapy for lysosomal storage disease: Principles, practice, and prospects, Annual Review of Genomics and Human Genetics, 2003; 4: 403-436.

Graff, C., et al., Directed evolution of an anti-carcinoembryonic antigen scFv with a 4-day monovalent dissociation half-time at 37 degrees C, Protein Eng Des Sel, 2004; 17(4):293-304.

Grahn, E., et al., Crystal Structure of the Marasmius Oreades Mushroom Lectin in Complex with aXenotransplantation Epitope, J Mol Biol, 2007; 369: 710-721.

Gupta, D., et al., Thermodynamics of Lectin-Carbohydrate Interactions: Binding of the Core Trimannoside of Asparagine-Linked Carbohydrates and Deoxy Analogs to Concanavalin A, J Biol Chem, 1997; 272(10): 6388-6392.

Hakomori, S.I., Aberrant Glycosylation in Tumors and Tumor-Associated Carbohydrate Antigens, Advances in Cancer Research, 1989; 52: 257-331.

Hammarstrom, S., The carcinoembryonic antigen (CEA) family: structures, suggested functions and expression in normal and malignant tissues, Semin Cancer Biol, 1999; 9(2): 67-81.

Hancock, S.M., M.D. Vaughan, and S.G. Withers, Engineering of glycosidases and glycosyltransferases, Curr Opin Chem Biol, 2006; 10(5): 509-19.

Haseley, S.R., J. Kamerling, and J.F.G. Vliegenthart, Unravelling carbohydrate interactions with Biosensors using surface plasmon resonance (SPR) detection, Topics in Current Chemistry, 2002; 218: 93-114.

Hemmingsen, L., et al., Evaluation of Carbohydrate Molecular Mechanical Force Fields by Quantum Mechanical Calculations, Carbohydr Res, 2004; 339: 937-948.

Herfurth, L., et al., Comparative Epitope Mapping with Saturation Transfer Difference NMR of Siayl Lewisa Compounds and Derviatives Bound to a Monoclonal Antibody, J Med Chem, 2005; 48: 6879-6886.

Hernandez Daranas et al., Thermodynamics of Binding of D-Galactose and Deoxy Derivatives thereof to the L-Arabinose-binding Protein, J Am Chem Soc, 2004; 126: 11870-11876.

Holt, G.D. and G.W. Hart, The Subcellular Distribution of Terminal N-Acetylglucosamine Moieties, J Biol Chem, 1986; 261: 8049-8057.

Huo et al., Molecular Dynamics and Free Energy Analyses of Cathepsin D-Inhibitor Interactions: Insight into Structure-Based Ligand Design, J Med Chem, 2002; 45(7): 1412-19.

Hwang, M.-J., et al., Derivation of Class II Force Fields. VI Carbohydrate Compounds and Anomeric Effects, Biopolymers, 1998; 45: 435-468.

Ito, W. and Y. Kurosawa, Effects of Substitutions of Closely-Related Amino-Acids at the Contact Surface in an Antigen-Antibody Complex on Thermodynamic Parameters, J Biol Chem, 1993; 268:16639-16647.

Jamal, S., et al., X-ray crystal structure of a non-crystalline cellulose-specific carbohydrate-binding module: CBM28, J Mol Biol, 2004; 339(2):253-8.

Jennings, H., Further Approaches for Optimizing Polysaccharide-Protein Conjugate Vaccines for Prevention of Invasive Bacterial Disease, J Infect Dis, 1992; 165:156-9.

Jorgensen et al., Comparison of Simple Potential Functions for Simulating Liquid Water, J Phys Chem, 1983; 79:926-935.

Kabsch and Sander, Dictionary of protein secondary structure: pattern recognition of hydrogen-bonded and geometrical features, Biopolymers, 1983; 22(12):2577-637.

Karaveg et al., Mechanism of Class I (Glycosylhydrolase Family 47) a-Mannosidases Involved in N-Glycan Processing and Endoplasmic Reticulum Quality Control, J Biol Chem, 2005; 280(16):16197-16207.

Karaveg, K., et al., Mechanism of Class 1 (Glycosylhydrolase Family 47) aMannosidases Involved in N-Glycan Processing and Endoplasmic Reticulum Quality Control, J Biol Chem, 2005; 280:16197-16207.

Kawatkar et al., Structural Basis of the Inhibition of Golgi Alpha-Mannosidase II by Mannostatin A and the Role of the Thiomethyl Moiety in Ligand-Protein Interactions, J Am Chem Soc, 2006; 128(25): 8310-9.

Khidekel, N., et al., Probing the dynamics of O-GlcNAc glycosylation in the brain using quantitative proteomics, Nat Chem Biol, 2007; 3(6): 339-48.

Kirkeby, S., H.C. Winter, and I.J. Goldstein, Comparison of the Binding Properties of the Mushroom Marasmius Oreades Lectin and Griffonia Simplicifolia 1-B Isolectin to Alphagalactosyl Carbohydrate Antigens in the Surface Phase, Xenotransplantation, 2004; 11(3):254-61.

Kirschner and Woods, "Quantum Mechanical Study of the Nonbonded Forces in Water-Methanol Complexes," J Phys Chem A, 2001; 105:4150-5.

Kuhn et al., Active-Site and Oligosaccharide Recognition Residues of Peptide-N-4-(N-Acetyl-Beta-D-Glucosaminyl) Asparagine Amidase-F, J Biol Chem, 1995; 270(49):29493-29497.

Kuttel, M., J.W. Brady, and K.J. Naidoo, Carbohydrate Solution Simulations: Producing a Force Field with Experimentally Consistent Primary Alcohol Rotational Frequencies and Populations, J Comput Chem, 2002; 23:1236-1243.

Laederach et al., Automated Docking of Maltose, 2-Deoxymaltose, and Maltotetraose into the Soybean /3-Amylase Active Site, Proteins: Structure, Function and Genetics, 1999; 37:166-175.

Laederach, A. and J. Reilly, Modeling Protein Recognition of Carbohydrates, Proteins: Struct Funct Genet, 2005; 60: 591-597.

Laederach, A. and J. Reilly, Specific Empirical Free Energy Function for Automated Docking of Carbohydrates to Proteins, J Com Chem, 2002; 24(14): 1748-1757.

Laitinen et al., MM-PBSA free energy analysis of endo-1,4-xylanase II (XynII)-substrate complexes: binding of the reactive sugar in a skew boat and chair conformation, Org Biomol Chem, 2003; 1(20): 3535-40.

Lammerts van Bueren, A. and A.B. Boraston, Binding sub-site dissection of a carbohydrate-binding module reveals the contribution of entropy to oligosaccharide recognition at "non-primary" binding subsites, J Mol Biol, 2004; 340(4): 869-79.

(56) References Cited

OTHER PUBLICATIONS

Lasters et al., "Enhanced dead-end elimination in the search for the global minimum energy conformation of a collection of protein side chains," Protein Eng, 1995; 8(8):815-22.
Laughlin, S.T., et al., Metabolic labeling of glycans with azido sugars for visualization and glycoproteomics, Methods Enzymol, 2006; 415: 230-50.
Lazaridis, T., Binding Affinity and Specificity from Computational Studies, Curr Org Chem, 2002. 6: 1319-1332.
Li, B., et al., Inhibition of Golgi Mannosidase II with Mannostatin A Analogues: Synthesis, Biological Evaluation, and Structure-Activity Relationship Studies, Chembiochem, 2004; 5: 1220-1227.
Li, Z. and T. Lazaridis, The Effect of Water Displacement on Binding Thermodynamics: Concanavalin A, J Phys Chem B, 2005; 109: 662-670.
Schwartz et al., "Formalization of the MESF unit of fluorescence intensity," Cytometry B Clin Cytom, Jan. 2004; 57(1):1-6.
Schwarzer et al., "Proteolytic Release of the Intramolecular Chaperone Domain Confers Processivity to Endosialidase F," J Biological Chem, Apr. 3, 2009; 284(14):9465-74.
Song et al., "Expression of bisecting N-acetylglucosaminyltransferase-III in human hepatocarcinoma tissues, fetal liver tissues, and hepatoma cell lines of Hep3B and HepG2," Cancer Invest, 2001; 19(8):799-807.
Spherotech, Inc., "SPHERO Flow Cytometry Multiplex Bead Assay Particles" Product Sheet, Lake Forest, IL, Available Oct. 24, 2007. [retrieved on Nov. 12, 2016]. Retrieved from the Internet: spherotech. com/new%20downloadable%20notes/Multiplex%20Assay% 20Particle%20Kits%202008-2009.pdf; 2 pages.
Spherotech, Inc., "About Spherotech" webpage. Lake Forest, IL. Copyright 2011. [retrieved on Feb. 15, 2012]. Retrieved from the Internet: spherotech.com/about.htm; 1 page.
Straatsma, "Holonomic Constraint Contributions to Free Energy Differences from Thermodynamic Integration Molecular Dynamics Simulations," Chem Phys Lett, Aug. 14, 1992. 196:297-302.
Tempel et al., "Structure of Mouse Golgi a-Mannosidase IA Reveals the Molecular Basis for Substrate Specificity among Class J (Family 47 Glycosylhydrolase) a1,2-Mannosidases," J Biol Chem, Jul. 9, 2004. 279(28):29774-29786. Available online on Apr. 21, 2004.
Tsui and Case, "Theory and Applications of the Generalized Born Solvation Model in Macromolecular Simulations," Biopolymers, 2001. 56:275-291. Available online on Dec. 4, 2001.
United States Trademark "Lectenz"—Reg. No. 4,264,797; registered on Dec. 12, 2012. Published for opposition on Jul. 7, 2009.
Wang et al., "Glycan microarray of Globo H and related structures for quantitative analysis of breast cancer," Proc Natl Acad Sci USA, Aug. 19, 2008; 105(33):11661-6.
Watson et al., "Sepctral Measurements of Large Particles by Flow Cytometry," Cytometry A, 2009; 75A:460-4.
Werz et al., "Automated synthesis of the tumor-associated carbohydrate antigens Gb-3 and Globo-H: incorporation of alpha-galactosidic linkages," J Am Chem Soc, Mar. 14, 2007; 129(10):2770-1. Published online Feb. 16, 2007.
Wilson et al., "Encoded Microcarriers For High-Throughput Multiplexed Detection," Agnew Chen Int Ed, 2006; 45:6104-6117.
Wood and Hoffman, "Evaluating fluorescence sensitivity on flow cytometers: an overview," Cytometry, Oct. 1, 1998; 33(2):256-9.
Yang and Nolan, "High-throughput screening and characterization of clones selected from phage display libraries," Cytometry A, Aug. 2007; 71 (8):625-31.
Yang, "Molecular Characterization of Flu-Receptor—Hemagglutinin Interactions. Computational Prediction of HA Specificity," Presented at conference titled Glycome: Structure to Disease, Paris, France, Sep. 14-18, 2007, 9 pgs.
Yang, "Multiplexed analysis of influenza virus type, sub-type, and receptor specificity," Presented at 4th National Carbohydrate Symposium. Banff, Alberta, Canada, May 1-3, 2008, 20 pgs.

Yang, "Multiplexed analysis of influenza virus type, sub-type, and receptor specificity," Presented at International Society for Advancement of Cytometry XXIV International Congress. Budapest, Hungary, May 17-21, 2008, 22 pgs.
Yang, "Multiplexed analysis of influenza virus type, sub-type, and receptor specificity," Presented at XXIV International Carbohydrate Symposium. Oslo, Norway, Jul. 27-Aug. 1, 2008, 22 pgs.
Yang, "Multiplexed analysis of influenza virus type, sub-type, and receptor specificity," Presented at IV Meeting of the Irish Cytometry Society. Dublin, Ireland, Nov. 25-26, 2008, 16 pgs.
Yang, "Multiplexed analysis of influenza virus type, sub-type, and receptor specificity," Poster presented at IV Meeting of the Irish Cytometry Society. Dublin, Ireland, Nov. 25-26, 2008, 1 pg.
Yang, "Multiplexed analysis of influenza virus type, sub-type, and receptor specificity," Presented at International Conference on Trends in Bioanalytical Sciences and Biosensors, 2009. Dublin, Ireland, Jan. 26-27, 2009, 17 pgs.
Yang et al., "A multiplex suspension array for screening of carbohydrate binding proteins and influenza" Poster presented at XXVI Congress of the International Society for Advancement of Cytometry. Baltimore, MD, May 21-25, 2011, 1 page.
Zacharias et al., "Inversion of Receptor Binding Preferences by Mutagenesis: Free Energy Thermodynamic Integration Studies of Sugar Binding to L-Arabinose Binding Proteins," Biochemistry, Jul. 27, 1993. 32:7428-7434.
Zhao et al., "N-linked glycosylation profiling of pancreatic cancer serum using capillary liquid phase separation coupled with mass spectrometric analysis," J Proteome Res, Mar. 2007; 6(3):1126-38. Published online Jan. 24, 2007.
Zhao et al., "Protein Biomarkers in Cancer: Natural Glycoprotein Microarray Approaches," Curr Opin Mol Ther, Dec. 2008; 10(6):602-10.
Kozmon and Tvaroška, "Catalytic Mechanism of Glycosyltransferases: Hybrid Quantum Mechanical/Molecular Mechanical Study of the Inverting N-Acetylglucosaminyltransferase I," J Am Chem Soc, Dec. 2006;27 128(51):16921-7.
Krishnamoorthy & Mahal, "Glycomic analysis: an array of technologies," ACS Chem Biol, Sep. 18, 2009; 4(9):715-32.
Kuhn et al., "Crystal-Structure of Peptide-N4-(N-Acetyl-ß-D-Glucosaminyl)asparagine Amidase F at 2.2-Å Resolution," Biochemistry, Oct. 4, 1994; 33(39):11699-706.
Kuhn et al., "Active Site and Oligosaccharide Recognition Residues of Peptide-N4-(N-acetyl-ß-D-glucosaminyl)asparagine Amidase F," Journal of Biological Chemistry, 1995; 270:29493-29497 (1995).
Kukuruzinska et al., "Protein glycosylation in yeast," Annu Rev Biochem, 1987; 56:915-44.
Kuzmanov et al., "The sweet and sour of serological glycoprotein tumor biomarker quantification," BMC Med, Feb. 7, 2013; 11:31.
Leach, Molecular Modelling: Principles and Applications (2nd Edition), Pearson: Harlow, England; Apr. 9, 2001. Cover page, title page and table of contents.
Leatherbarrow et al., "Transition-state stabilization in the mechanism of tyrosyl-tRNA synthetase revealed by protein engineering," Proc Natl Acad Sci USA, Dec. 1985; 82(23):7840-4.
Lee et al., "An optimized approach for enrichment of glycoproteins from cell culture lysates using native multi-lectin affinity chromatography," J Sep Sci, Sep. 2012; 35(18):2445-52.
Lectenz® Bio, "Lectenz® Platform" [retrieved on Jun. 11, 2018]. Available at least as early as Jun. 11, 2018. Retrieved from the Internet: lectenz.com/technology-2/lectenz-platform; 6 pgs.
Lemp et al., "Molecular cloning and heterologous expression of N-glycosidase F from Flavobacterium meningosepticum," J Biol Chem, 1990; 265(26):15606-10.
Lerner et al., "Evolution of a Catabolic Pathway in Bacteria," Science, Dec. 4, 1964; 146(3649):1313-5.
Li and d'Anjou, "Pharmacological significance of glycosylation in therapeutic proteins," Curr Opin Biotechnol, Dec. 2009; 20(6):678-84. Epub Nov. 4, 2009.
Lienemann et al., "Toward understanding of carbohydrate binding and substrate specificity of a glycosyl hydrolase 18 family (GH-18) chitinase from Trichoderma harzianum," Glycobiology, Jul. 2009; 19(10):1116-26.

(56) References Cited

OTHER PUBLICATIONS

Liener, The Lectins: Properties, Functions, and Applications in Biology and Medicine, Academic Press: Orlando, FL; 1986. Cover page, title page and table of contents.

Lo et al., "Optimizing Protein Expression and Purification of N-glycan Lectenz®: a High Affinity Carbohydrate-Recognizing Protein," Georgia Bio Innovation Summit. Abstract and Poster Presentation, Atlanta, GA; Nov. 2, 2015. 3 pages.

Loo et al., "Using Secretion to Solve a Solubility Problem: High-Yield Expression in *Escherichia coli* and Purification of the Bacterial Glycoamidase PNGase F," Protein Expression and Purification, 2002; 24:90-8.

Lopes et al., "Computational design of protein-ligand binding: modifying the specificity of asparaginyl-tRNA synthetase," J Comput Chem, Apr. 30, 2010; 31(6):1273-86.

Lundquist and Toone, "The Cluster Glycoside Effect," Chem Rev, Feb. 2002; 102(2):555-78.

Lutz, "Beyond directed evolution—semi-rational protein engineering and design," Curr Opin Biotechnol, Dec. 2010; 21(6):734-43. Epub Sep. 24, 2010.

Mackerell, Jr., "Empirical force fields for biological macromolecules: overview and issues," J Comput Chem, Oct. 2004; 25(13):1584-604.

Manimala et al., "High-throughput carbohydrate microarray profiling of 27 antibodies demonstrates widespread specificity problems," Glycobiology, Aug. 2007; 17(8):17C-23C. Epub May 4, 2007.

Martin, "Computationally Guided Mutagenesis: Construction of a Saturation Mutagenesis Phage-Display Library Based on an Inactive OGlcNAcase Mutant," Abstract, PEGS: The Essential Protein Engineering Summit, Boston, MA, Apr. 30-May 4, 2012; 1 pg.

Martin, "Computationally Guided Directed Evolution of O-GlcNAcase into a Reagent Specific for [beta]-O-GlcNAc" Ph D. Thesis Dissertation Abstract, National University of Ireland—Galway, 2013; 3 pages.

McCammon et al., "Dynamics of folded proteins," Nature, Jun. 16, 1977; 267(5612):585-90.

McCammon, "Theory of biomolecular recognition," Curr Opin Structural Biology, Apr. 1998; 8(2):245-9.

Martin, "Computationally Guided Directed Evolution of O-GlcNAcase into a Reagent Specific for [beta]-O-GlcNAc" Ph D. Thesis Dissertation, National University of Ireland—Galway, Dec. 13, 2013; available online [retrieved on Apr. 19, 2018]. Retrieved from the Internet: hdl.handle.net/10379/4401; 156 pages.

Mega et al., "Characterization of Carbohydrate-Binding Specificity of Concanavalin A by Competitive Binding of Pyridylamino Sugar Chains," J Biochem, Mar. 1992; 111(3):396-400.

Meier & Duus, "Carbohydrate dynamics: Antibody glycans wiggle and jiggle," Nat Chem Biol, Mar. 2011; 7(3):131-2.

Miller et al., "Construction and screening of antigen targeted immune yeast surface display antibody libraries," Curr Protoc Cytom, Jul. 2008; Chapter 4: Unit4.7.

Mills et al., "An extracellular Darwinian experiment with a self-duplicating nucleic acid molecule," Proc Natl Acad Sci USA, Jul. 1967; 58(1):217-24.

Moreira et al., "Computational Alanine Scanning Mutagenesis—An Improved Methodological Approach," J Comp Chem, 2007; 28:644-54. Epub Dec. 28, 2006.

Morris et al., "Selective binding of RNase B glycoforms by polydopamine-immobilized concanavalin A," Anal Chem, Jul. 1, 2009; 81(13):5413-20.

Murrell, "The systems biology of glycosylation," Chembiochem, 2004; 5(10):1334-47.

Mussar et al., "Peptide: N-glycosidase F: studies on the glycoprotein aminoglycan amidase from Flavobacterium Meningosepticum," J Biochem Biophys Methods, 1989; 20(1):53-68.

Nieba et al., "Biacore analysis of histidine-tagged proteins using a chelating NTA sensor chip," Anal Biochem, Oct. 15, 1997; 252(2):217-28.

Noble et al., "A comparison of protein quantitation assays for biopharmaceutical applications," Mol Biotechnol, Oct. 2007; 37(2):99-111.

Norris et al., "Purification and crystallization of the endoglycosidase PNGase F, a peptide:N-glycosidase from Flavobacterium meningosepticum," J Mol Biol, Aug. 26, 1994; 241(4):624-6.

Okimoto et al., "High-performance drug discovery: computational screening by combining docking and molecular dynamics simulations," PLoS Comput Biol, Oct. 2009; 5(10):e1000528. Epub Oct. 9, 2009.

Ongay et al., "Glycopeptide enrichment and separation for protein glycosylation analysis," J Sep Sci, Sep. 2012; 35(18):2341-72.

Parikh et al., "Affinity and Specificity Characterization of Fbs1 via Surface Plasmon Resonance and Glycan Array Screening," (abstract) 2012 CURO (Center for Undergraduate Research Opportunities) Symposium, University of Georgia, Athens, Georgia, Apr. 2, 2012, Poster #47, Program & Abstracts (cover page, title page, program listing, and abstract #47 at pp. 77-78, 6 pages total) [also available electronically as "2012 Book of Abstracts" from the CURO Symposium Books of Abstracts Archive at http://curo.uga edu/symposium/].

Parikh et al., Affinity and Specificity Characterization of Fbs1 via Surface Plasmon Resonance, (poster) 2012 CURO (Center for Undergraduate Research Opportunities) Symposium, University of Georgia, Athens, Georgia, Apr. 2, 2012, 1 page.

Patel and Hecht, "Directed evolution of the peroxidase activity of a de novo-designed protein," Protein Eng Des Sel, Sep. 2012; 25(9):445-52. Epub Jun. 3, 2012.

Patrick and Firth, "Strategies and computational tools for improving randomized protein libraries," Biomolecular Engineering 2005; 22:105-112.

Paul et al., "N-Glycan Lectenz® Affinity Chromatography and Biosensors Applications" Georgia Bio Innovation Summit. Abstract and Poster Presentation, Atlanta, GA; Nov. 2, 2015. 3 pages.

Perona et al., "Structural origins of substrate discrimination in trypsin and chymotrypsin," Biochemistry, Feb. 7, 1995; 34(5):1489-99.

Pettersen et al., "UCSF Chimera—a visualization system for exploratory research and analysis," J Comput Chem, Oct. 2004; 25(13):1605-12.

Pierdominici-Sottile et al., "Free-energy computations identify the mutations required to confer trans-sialidase activity into Trypanosoma rangeli sialidase," Proteins, Mar. 2014; 82(3):424-35. Epub Oct. 17, 2013.

Plummer et al., "Demonstration of peptide:N-glycosidase F activity in endo-beta-Nacetylglucosaminidase F preparations," J Biol Chem, 1984; 259(17):10700-4.

Porcel et al., "Use of a panel of tumor markers (carcinoembryonic antigen, cancer antigen 125, carbohydrate antigen 15-3, and cytokeratin 19 fragments) in pleural fluid for the differential diagnosis of benign and malignant effusions," Chest, Dec. 2004; 126(6): 1757-63.

Prien et al., "A multi-method approach toward de novo glycan characterization: a Man-5 case study," Glycobiology, May 2010; 20(5):629-47. Epub Jan. 27, 2010.

Rajpal et al. "A general method for greatly improving the affinity of antibodies by using combinatorial libraries," PNAS, Jun. 2005; 102(24):8466-71.

Raman et al., "Glycomics: an integrated systems approach to structure-function relationships of glycans," Nat. Methods, 2005; 2(11):817-24.

Rao et al., "Mutations of endo-beta-N-acetylglucosaminidase H active site residueAs sp130 anG glu132: activities and conformations," Protein Sci, Nov. 1999; 8(11):2338-46.

Rayon et al., "The protein N-glycosylation in plants," J Exper Botany, Sep. 1998; 49(326):1463-72.

Roe and Cheatham, "PTRAJ and CPPTRAJ: Software for Processing and Analysis of Molecular Dynamics Trajectory Data," J Chem Theory Comput, Jul. 9, 2013; 9(7):3084-95. Epub Jun. 25, 2013.

Rudd et al., "Separation and analysis of the glycoform populations of ribonuclease B using capillary electrophoresis," Glycoconj J, Apr. 1992; 9(2):86-91.

Rye & Withers, "Glycosidase mechanisms," Curr Opin Chem Biol, Oct. 2000; 4(5):573-80.

(56) References Cited

OTHER PUBLICATIONS

Samli, "Lectenz: Carbohydrate-Recognizing Biosensor Engineered via Computationally-Guided Directed Evolution," PhD. Thesis Dissertation Oral Presentation Slides, The University of Georgia, Athens, Georgia, Apr. 18, 2014; 78 pages.

Samli, "Lectenz: Carbohydrate-Recognizing Biosensor Engineered via Computationally-Guided Directed Evolution," PhD. Thesis Dissertation, The University of Georgia, Athens, Georgia, 2016; 181 pages.

Saul et al., "Crystal structure of Urtica dioica agglutinin, a superantigen presented by MHC molecules of class I and class II," Structure, Jun. 15, 2000; 8(6):593-603.

Schlick et al., "Inhibition binding studies of glycodendrimerlectin interactions using surface plasmon resonance," Tetrahedron, Jul. 17, 2010; 66(29):5305-10.

Schneider et al., "NIH Image to ImageJ: 25 years of image analysis," Nat Methods, Jul. 2012; 9(7):671-5.

Scouras et al., "The dynameomics rotamer library: Amino acid side chain conformations and dynamics from comprehensive molecular dynamics simulations in water," Protein Sci, Feb. 2011; 20(2):341-52.

Shim et al., "Directed evolution of a beta-glycosidase from *Agrobacterium* sp. to enhance its glycosynthase activity toward C3-modified donor sugars," Protein Eng Des Sel, Sep. 2012; 25(9):465-72.

Showalter and Brüschweiler, "Validation of Molecular Dynamics Simulations of Biomolecules Using NMR Spin Relaxation as Benchmarks: Application to the AMBER99SB Force Field," J Chem Theory Comput, May 2007; 3(3):961-75.

Sievers et al., "Fast, scalable generation of high-quality protein multiple sequence alignments using Clustal Omega," Mol Syst Biol, Oct. 11, 2011; 7:539.

Sigal et al., "Thiol-beta-lactamase: replacement of the active-site serine of RTEM beta-lactamase by a cysteine residue," Proc Natl Acad Sci USA, Dec. 1982; 79(23):7157-60.

Smith, "Filamentous fusion phage: novel expression vectors that display cloned antigens on the virion surface," Science, Jun. 14, 1985; 228(4705):1315-7.

Socha and Tokuriki, "Modulating protein stability—directed evolution strategies for improved protein function," FEBS J, Nov. 2013; 280(22):5582-95. Epub Jun. 18, 2013.

Steinbrecher and Labahn, "Towards accurate free energy calculations in ligand protein-binding studies," Curr Med Chem, 2010; 17(8):767-85.

Stoltenburg et al., "SELEX—A (r)evolutionary method to generate high-affinity nucleic acid ligands," Biomol Eng, Oct. 2007; 24(4):381-403. Epub Jun. 16, 2007.

Stone et al., "T cell receptor engineering," Methods Enzymol, 2012; 503:189-222.

Stortz et al., "Comparison of different force fields for the study of disaccharides," Carbohydrate Research, Nov. 2, 2009; 344(16):2217-28. Epub Aug. 22, 2009.

Sun et al., "Identification and Characterization of a Novel Prokaryotic Peptide: N-Glycosidase From Elizabethkingia Meningoseptica," J Biol Chem, Mar. 20, 2015; 290(12):7452-62.

Takashima and Amano, "Glycosylation and secretion of human a-amylases," Advances in Biological Chemistry, Feb. 2012; 2:10-9.

Taniguchi et al., "The Second Golden Age of Glycomics: From Functional Glycomics to Clinical Applications," J Proteome Res, Feb. 2009; 8(2):425-6.

Tarentino et al., "Deglycosylation of asparagine-linked glycans by peptide:N-glycosidase F," Biochemistry, Aug. 13, 1985; 24(17):4665-71.

Tatusova et al., "BLAST 2 Sequences, a new tool for comparing protein and nucleotide sequences," FEMS Microbiol Lett, 1999; 174:247-250.

Taylor and Drickamer, Introduction to glycobiology, Edn. 2nd. (Oxford University Press, Oxford ; New York; 2006). Cover page, title page and table of contents.

Taylor and Drickamer, "Structural insights into what glycan arrays tell us about how glycan-binding proteins interact with their ligands," Glycobiology, Nov. 2009; 19(11):1155-62. Epub Jun. 15, 2009.

Taylor-Papadimitriou et al., "MUC1 and cancer," Biochim Biophys Acta, Oct. 8, 1999; 1455(2-3):301-13.

Thompson et al., "Heparan sulfate phage display antibodies identify distinct epitopes with complex binding characteristics: insights into protein binding specificities," J Biological Chem, Dec. 18, 2009; 284(51):35621-31. Epub Oct. 16, 2009.

Tinberg et al., "Computational design of ligand-binding proteins with high affinity and selectivity," Nature, Sep. 12, 2013; 501(7466):212-6. Epub Sep. 4, 2013.

Tobin et al., "Directed evolution: the 'rational' basis for 'irrational' design," Curr Opin Struct Biol, Aug. 2000; 10(4):421-7.

Tohidkia et al., "Molecular considerations for development of phage antibody libraries," J Drug Targeting, Apr. 2012; 20(3):195-208. Epub Sep. 27, 2011.

Tretter et al., "Peptide-N4-(N-acetyl-beta-glucosaminyl)asparagine amidase F cannot release glycans with fucose attached alpha 1—3 to the asparagine-linked N-acetylglucosamine residue," Eur J Biochem, Aug. 1, 1991; 199(3):647-52.

UniProt Consortium, "Activities at the Universal Protein Resource (UniProt)," Nucleic Acids Res, Jan. 2014; 42(Database Issue):D191-8. Epub Nov. 18, 2013.

Van Gunsteren et al., Computation of Free Energy in Practice: Choice of Approximations and Accuracy Limiting Factors, vol. 2. (ESCOM, Leiden; 1993). Cover page, title page and table of contents.

Venekei et al., "Attempts to convert chymotrypsin to trypsin," FEBS Lett, Jan. 29, 1996; 379(2):143-7. Corrected and republished Mar. 25, 1996.

Voigt et al., "Computationally focusing the directed evolution of proteins," J Cell Biochem Suppl Suppl, 2001; 37:58-63.

Wang et al., "Poisson-Boltzmann Solvents in Molecular Dynamics Simulations," Comm Computational Physics, May 2008; 3(5):1010-1031. Epub Jan. 24, 2008.

Wang et al., "N-Terminal Deletion of Peptide:N-Glycanase Results in Enhanced Deglycosylation Activity," PLoS One, Dec. 16, 2009; 4(12):e8335.

Lins, R.D. and H. Hunenberger, A New GROMOS Force Field for Hexopyranose-Based Carbohydrates, J Comput Chem, 2005; 26: 1400-1412.

Lis, H. and N. Sharon, Lectins: Carbohydrate-Specific Proteins That Mediate Cellular Recognition, Chem Rev, 1998; 98: 637-674.

Lo-Man, R., et al., A fully synthetic therapeutic vaccine candidate targeting carcinomaassociated Tn carbohydrate antigen induces tumor-specific antibodies in nonhuman primates, Cancer Research, 2004; 64(14): 4987-4994.

Looger et al., Computational design of receptor and sensor proteins with novel functions, Nature, 2003; 423(6936): 185-90.

Love, D.C. and J.A. Hanover, The hexosamine signaling pathway: deciphering the "O-GlcNAc code," Sci STKE, 2005; 2005(312): re13.

Lovell et al., The penultimate rotamer library, Proteins, 2000; 40(3): 389-408.

Lundquist, J.J., et al., Towards high affinity carbohydrate-binding proteins: Directed evolution of murine galectin-3, Can J Chem, 2002; 80: 999-1009.

Luo et al., The 1.8 A structures of leech intramolecular trans-sialidase complexes: evidence of its enzymatic mechanism, J Mol Biol, 1999. 285(1):323-32.

Lycknert, K., T. Rundlof, and G. Widmalm, Solution Structure of a Type! H Antigen Trisaccharide at a Mice/far Surface: NMR Relaxation and Molecular Dynamics Simulation Studies, J Phys Chem B, 2002. 106: 5275-5280.

Majumdar, G., et al., Insulin stimulates and diabetes inhibits O-linked Nacetylglucosamine trans/erase and O-glycosylation of Sp1, Diabetes, 2004. 53(12):3184-92.

Malhotra, R., et al., Glycosylation Changes of IgG Associated with Rheumatoid Arthritis can Activate Complement via the Mannose-Binding Protein, Nature Medicine, 1995. 1(3):237-243.

(56) References Cited

OTHER PUBLICATIONS

Mandal, D.K., et al., Studies of the Binding Specificity of Concanavalin A. Nature of the Extended Binding Site for Asparagine-Linked Carbohydrates, Biochemistry, 1994. 33:1157-1162.

Mandal, D.K., N. Kishore, and C.F. Brewer, Thermodynamics of Lectin-Carbohydrate Interactions—Titration Microcalorimetry Measurements of the Binding of N-Linked Carbohydrates and Ovalbumin to Concanavalin A, Biochemistry, 1994. 33: 1149-1156.

McGreal, E., J.L. Miller, and S. Gordon, Ligand recognition by antigen-presenting cell C-type lectin receptors, Curr Opin Immunol, 2005. 17(1): 18-24.

Morris, G.M., et al., Automated Docking Using a Lamarckian Genetic Algorithm and an Empirical Binding Free Energy Function, J Com Chem., 1998. 19(14): 1639-1662.

Moura, LC., et al., Glycosylation and size of IgAJ are essential for interaction with mesangial transferrin receptor in IgA hephropathy, Journal of the American Society of Nephrology, 2004. 15(3): 622-634.

Mulakala et al., Docking studies on glycoside hydrolase Family 47 endoplasmic reticulum a-(1!2)-mannosidase I to elucidate the pathway to the substrate transition state, Carbohydr Res, 2006. 341: 2233-2245.

Naismith, J.H., et al., Refined Structure of Concanavalin A Complexed with Methyl a-DMannopyranoside at 2. 0 A Resolution and Comparison with the Saccharide-Free Structure, Acta Crystallogr, 1994. D50: 847-858.

Neufeld, E.F., Lysosomal Storage Diseases, Annual Review of Biochemistry, 1991. 60: 257-280.

Parekh, R.B., et al., Association of Rheumatoid Arthritis and Primary Osteoarthritis with Changes in the Glycosylation Pattern of Total Serum IgG, Nature, 1985. 316: 452-457.

Park, H., J. Lee, and S. Lee, Critical Assessment of the Automated AutoDock as a New Docking Tool for Virtual Screening, Proteins: Struct Funct Bioinformatics, 2006;. 65:549-554.

Pathiaseril, A. and R.J. Woods, Relative Energies of Binding for Antibody-Carbohydrate Antigen Complexes Computed from Free-Energy Simulations, J Am Chem Soc, 2000; 122: 331-338.

Pearlman, D.A. and S. Charifson, Are Free Energy Calculations Useful in Practice? A Comparison with Rapid Scoring Functions for the p38 MAP Kinase Protein System, J Med Chem, 2001; 44(21): 3417-23.

Perez, S., et al., A Comparison and Chemometric Analysis of Several Molecular Mechanics Force Fields and Parameter Sets Applied to Carbohydrates, Carb Res, 1998; 314: 141-155.

Petri, W.A., Jr., R. Haque, and B.J. Mann, The bittersweet interface of parasite and host: lectin-carbohydrate interactions during human invasion by the parasite Entamoeba histolytica, Annu Rev Microbiol, 2002; 56: 39-64.

Ramkumar, R., A. Surolia, and S.K. Podder, Energetics of Carbohydrate Binding by a 14 kDa S-Type Mammalian Lectin, Biochem J, 1995; 308: 237-241.

Ramsland, A., et al., Structural convergence of antibody binding of carbohydrate determinants in Lewis Y tumor antigens, J Mol Biol, 2004; 340( 4 ): 809-18.

Rhimi, M., et al., Probing the Essential Catalytic Residues and Substrate Affinity in the Thermoactive Bacillus stearothermophilus USJ 00 L-Arabinose Isomerase by SiteDirected Mutagenesis, J Bacterial, 2007; 189(9): 3556-3563.

Roquemore, E., T.Y. Chou, and G.W. Hart, Detection of O-/inked N-acetylglucosamine (O-GlcNAc) on cytoplasmic and nuclear proteins, Methods Enzymol, 1994; 230: 443-60.

Rudd et al., Glycoforms Modify the Dynamic Stability and Functional Activity of an Enzyme, Biochemistry, 1994; 33: 17-22.

Rundlof et al., A Conformational Study of the Trisaccharide beta-D-Glcp-(1->2)[Beta-D-Glcp-(1->3)] Alpha-D-Glcp-OMe by NMR NOESY and TROESY Experiments, Computer Simulations, and X-ray Crystal Structure Analysis, Chem A Eur J, 2001; 7(8): 1750-1758.

Sahasrabuddhe et al., Studies on recombinant single chain Jacalin lectin reveal reduced affinity for saccharides despite normal folding like native Jaca/in, Protein Sci, 2004; 13(12): 3264-73.

Sakai et al., Isolation and Characterixation of Phage-Displayed Single Chain Antibodies Recognizing Nonreducing Terminal Mannose Residues.1.A New Strategy for Generation of Anti-Carbohydrate Antibodies, Biochem, 2007; 46:253-62.

Sanders, W.J., et al., Inhibition of L-selectin-mediated Leukocyte Rolling by Synthetic Glycoprotein Mimics, J Biol Chem, 1999; 274(9): 5271-5278.

Scanlan, C.N., et al., The Broadly Neutralizing Anti-Human Immunodeficiency Virus Type I Antibody 2GI 2 Recognizes a Cluster of al $2 Mannose Residues on the Outer Face of gpl20, Journal of Virology, 2002; 76(14): 7306-7321.

Schubert et al., Probing electrostatic interactions along the reaction pathway of a glycoside hydrolase: histidine characterization by NMR spectroscopy, Biochemistry, 2007; 46(25): 7383-95.

Schwarz et al., Thermodynamics of Monosaccharide Binding to Concanavalin-A, Pea (Pisum-Sativum) Lectin, and Lentil (Lens-Culinaris) Lectin, J Biol Chem, 1993; 268:7668-77.

Sharon and Lis, Carbohydrates in Cell Recognition, Scien Amer, 1993; Jan:82-9.

Sly, W.S. and C. Vogler, Brain-directed gene therapy for lysosomal storage disease: going well beyond the blood-brain barrier, Proc Natl Acad Sci U S A, 2002; 99(9):5760-2.

Smith, G., Filamentous fusion phage: novel expression vectors that display cloned antigens on the virion surface, Science, 1985; 228: 1315-1317.

Sotriffer, C.A., et al., Automated Docking of Ligands to Antibodies: Methods and Applications, Methods, Companion to Methods in Enzymol., 2000; 20: 280-291.

Spieser, S.A.H., et al., Improved Carbohydrate Force Field for GROMOS: Ring and Hydroxymethyl Group Conformations and Exo-Anomeric Effect, Carbohydr Res, 1999; 322: 264-273.

Sivasubramanian et al., Structural Model of the mAb 806-EGFR Complex Using Computational Docking followed by Computational and Experimental Mutagenesis, Structure, 2006; 14:401-414.

Stura et al., Strategies in the Crystallization of Glycoproteins and Protein Complexes, J Cryst Growth, 1992; 122:273-285.

Su et al., Engineered yeast with PNGase F on cell surface for releasing of N-glycans from glycoproteins, Enzyme and Microbial Technology, 2007; 40(6): 1496-1502.

Swaminathan, C., et al., Thermodynamic Analyses Reveal Role of Water Release in Epitope Recognition by a Monoclonal Antibody Against the Human Guanylyl Cyclase C Receptor, J Biol Chem, 1999; 274(44): 31272-31278.

Taniguchi, N. and J.C. Paulson, Frontiers in glycomics; bioinformatics and biomarkers in disease. Sep. 11-13, 2006 Natcher Conference Center, NIH Campus, Bethesda, MD, USA, Proteomics, 2007; 7: 1360-1363.

Tessier et al., "Extension of the GLYCAM06 Biomolecular Force Field to Lipids, Lipid Bilayers and Glycolipids" Mol Simul, 2008; 34(4):349-63.

Thomas, R., et al., Structure of an Anti-Blood Group A Fv and Improvement of Its Binding Affinity without Loss of Specificity, J Biol Chem, 2002; 277(3): 2059-2064.

Tschampel and Woods, "Quantifying the Role of Water in Protein—Carbohydrate Interactions," J Phys Chem A, 2003; 107:9175-81.

Varid et al., "Sialic Acids" Ch. 14 in Essentials of Glycobiology, 2nd Edition, Cold Spring Harbor Press, Cold Spring Harbor, NY. 2009. Obtained online at www.ncbi.nlm.nih.gov/books/NBK1920/. Retrieved on Jul. 27, 2021.

Yang, Loretta "High-specificity affinity reagents for the detection of glycan sialylation," Grant Abstract, Grant No. R41GM113351 [online]. Granting Organization: National Institutes of Health, Department of Health and Human Services. Award Year: 2015. Solicitation Year: 2016. [retrieved on Apr. 21, 2017]. Retrieved from the Internet: sbir.gov/print/sbirsearch/detail/1028019; 3 pgs.

International Patent Application No. PCT/US2018/029079, filed Apr. 24, 2018; International Preliminary Report on Patentability dated Oct. 29, 2019; 8 pages.

(56) References Cited

OTHER PUBLICATIONS

International Patent Application No. PCT/US2018/029079, filed Apr. 24, 2018; International Search Report and Written Opinion, dated Oct. 30, 2018; 12 pages.
Wu et al., "Novel Sialoglycan Lectenz® Reagents," 11th Georgia Glycoscience Symposium. Abstract and Poster Presentation, Athens, GA; Apr. 25, 2017. 2 pages.
Yang et al., "A Rapid Method for Monitoring Glycosylation Features during Biomanufacturing," Biomanufacturing Technology Summit. Abstract and Poster Presentation, Rockville, MD; Jun. 23, 2016.
Yang et al., "Development of a Glycoprofiling Method Using Multiplex Flow Cytometry," USP Workshop on Glycosylation Analysis for Biopharmaceuticals. Abstract and Poster Presentation, Rockville, MD; Aug. 25-26, 2015.
Samli and Joshi, "Differential Glycome Gene Expression Profiling of Human Embryonic Stem Cells and Mesenchymal Stem Cells" 8th Jenner Glycobiology and Medicine Symposium, Royal Society of Medicine, University College Dublin, Oct. 21-23, 2007. 1 page.
Samli et al., "Developing Novel Glycan Binding Agents," Conference Abstract in Glycobiology, 2008; 18(11):953.
Samli et al., "Glycoinformatics: Text Mining Lectin and Glycan Interactions in Bioprocesses," Conference Abstract in Glycobiology, 2008; 18(11):975.
Samli et al., "Lectenz®: Carbohydrate-Binding Biomolecules Engineered via Computational Modeling and Directed Evolution," Graduate Students and Postdocs in Science 3rd Annual Scientific Research Day. Abstract and Presentation. The University of Georgia, Athens, GA; May 20, 2011. 32 pages.
Samli et al., "Lectenz (R): Carbohydrate-Binding Biomolecules Engineered via Computational Modeling and Directed Evolution," Conference Paper in Glycobiology, Nov. 2011; 21(11): 1482.
Samli et al., "Lectenz®: Carbohydrate-Binding Biomolecules Engineered via Computationally Modeling and Direct Evolution," Eighth Annual Protein Engineering Summit. Abstract. Boston, MA; Apr. 30-May 4, 2012. 1 page.
Samli et al., "Engineering a High Affinity Carbohydrate-Recognizing Protein via in silico Modeling and in vitro Directed Evolution," (poster), 2012 Georgia Life Sciences, Atlanta, GA, Oct. 3, 2012; 1 page.
Samli et al., "Engineering a High Affinity Carbohydrate-Recognizing Protein via in silico Modeling and in vitro Directed Evolution" (abstract) 2012 Georgia Life Sciences Summit, Atlanta, GA, Oct. 3, 2012, Poster #61, Conference Program eBook, at p. 68 (91 pages).
Samli et al., "Engineering Carbohydrate Recognizing Biosensors via Computational Modeling and Directed Evolution" (abstract), The 2012 Joint Meeting of the Society for Glycobiology and American Society for Matrix Biology, San Diego, CA, USA, Nov. 11-14, 2012; Conference Program and Abstracts published in Glycobiology, 22(11 ): 1487-1661 (Nov. 1, 2012) (175 pages); abstract #44 at p. 1533 [also available electronically at academic.oup.com/glycob/articlelookup/doi/10.1093/glycob/cws 127].
Samli et al., "Engineering Carbohydrate Recognizing Biosensors via Computational Modeling and Directed Evolution," Conference Paper in Glycobiology, Nov. 2012; 22(11): 1533.
Samli et al., "Targeting Glycans with Lectenz®: Engineered Glycan—Binding Biomolecules," Ninth Annual Protein Engineering Summit. Poster. Boston, MA; Apr. 29-May 3, 2013. 1 page.
Zheng et al., Serum 3'-sulfo-Lea indication of gastric cancer metastasis. Clin Chim Acta 405, 119-126 (2009).
Zhao et al., Comparative serum glycoproteomics using lectin selected sialic acid glycoproteins with mass spectrometric analysis: application to pancreatic cancer serum. J Proteome Res 5, 1792-1802 (2006).
Yu et al., Selective Exo-Enzymatic Labeling Detects Increased Cell Surface Sialoglycoprotein Expression upon Megakaryocytic Differentiation. J Biol Chem 291, 3982-3989 (2016).
Yamamoto et al., Sialic acid-binding motif of Maackia amurensis lectins. J Biochem 121, 756-761 (1997).

Xu et al., Crystal structure of the NanB sialidase from *Streptococcus pneumoniae*. J Mol Biol 384, 436-449 (2008).
Woods et al., Computational glycoscience: characterizing the spatial and temporal properties of glycans and glycan-protein complexes. Curr Opin Struct Biol 20, 575-583 (2010).
Tajiri et al., Oligosaccharide profiles of the prostate specific antigen in free and complexed forms from the prostate cancer patient serum and in seminal plasma: a glycopeptide approach. Glycobiology 18, 2-8 (2008).
Samraj et al., Involvement of a non-human sialic Acid in human cancer. Front Oncol 4, 33 (2014).
Padler-Karavani et al., Cross-comparison of protein recognition of sialic acid diversity on two novel sialoglycan microarrays. J Biol Chem 287, 22593-22608 (2012).
Nicholls et al., Sialic acid receptor detection in the human respiratory tract: evidence for widespread distribution of potential binding sites for human and avian influenza viruses. Respir Res 8, 73 (2007).
Martin et al., Defining the structural origin of the substrate sequence independence of O-GlcNAcase using a combination of molecular docking and dynamics simulation. Glycobiology 24, 85-96 (2014).
Lee et al., An optimized approach for enrichment of glycoproteins from cell culture lysates using native multi-lectin affinity chromatography. J Sep Sci 35, 2445-2452 (2012).
Kadirvelraj et al., Structure and binding analysis of Polyporus squamosus lectin in complex with the Neu5Ac{alpha}2-6Gal{beta}1-4GlcNAc human-type influenza receptor. Glycobiology 21, 973-984 (2011).
Haseley et al., Characterization of the carbohydrate binding specificity and kinetic parameters of lectins by using surface plasmon resonance. Anal Biochem 274, 203-210 (1999).
Hadden et al., Calculating binding free energies for protein-carbohydrate complexes. Methods Mol Biol 1273, 431-465 (2015).
Gut et al., Structural and functional studies of *Streptococcus pneumoniae* neuraminidase B: An intramolecular trans-sialidase. FEBS Lett 582, 3348-3352 (2008).
Geisler et al., Effective glycoanalysis with Maackia amurensis lectins requires a clear understanding of their binding specificities. Glycobiology 21, 988-993 (2011).
Ford et al., Molecular dynamics simulations of galectin-1-oligosaccharide complexes reveal the molecular basis for ligand diversity. Proteins 53, 229-240 (2003).
Chao et al., Isolating and engineering human antibodies using yeast surface display. Nat Protoc 1, 755-768 (2006).
Bai et al., Enhanced 3-O-sulfation of galactose in Asn-linked glycans and Maackia amurensis lectin binding in a new Chinese hamster ovary cell line. Glycobiology 11, 621-632 (2001).
BioWORLD, "Separopore 4B-CL" Product Info Sheet. Retrieved on Jul. 28, 2021. Retrieved from the Internet: bio-world.com/index.php?main_page=product_info&old_products_id=1290; 3 pgs.
Lippow et al., "Progress in computational protein design" Curr Opin Biotechnol, Sep. 14, 2007; 18(4):305-11.
Henrissat et al., Conserved catalytic machinery and the prediction of a common fold for several families of glycosyl hydrolases. Proc Natl Acad Sci USA, 92: 1090-1094. (1995).
Uniprot Accession No. A0A077EH19, "Uncharacterized protein," Gene Name: BD94_1060, Organism: Elizabethkingia anophelis NUHPI [online]. Oct. 29, 2014 [retrieved on Jun. 24, 2019]. Retrieved from the Internet: URL: uniprot.org/uniprot/A0A077EH19.txt; 1 page.
Lectenz [online]. United States Patent and Trademark Office Trademark Electronic Search System (TESS). Trademark application filed on Dec. 26, 2007, published for opposition on Jul. 7, 2009. Available online [retrieved on Aug. 19, 2011]. Retrieved from the Internet: tess2.uspto.gov/bin/showfield?f=doc&state=4004:787618.2.1; 2 pgs.
National Center for Biotechnology Information, National Library of Medicine, National Institutes of Health, GenBank Locus AF165910, Accession No. AF165910, "Chryseobacterium meningosepticum peptide:N-glycosidase F precursor (png) gene, partial cds," [online]. Bethesda, MD [retrieved on May 9, 2018]. Retrieved from the Internet: ncbi.nlm.nih.gov/nuccore/AF165910; 2 pgs.
National Center for Biotechnology Information, National Library of Medicine, National Institutes of Health, GenBank Locus FVBPNG,

(56) References Cited

OTHER PUBLICATIONS

Accession No. J05449,"F.meningosepticum peptide-N-4-(N-acetyl-beta-D-glucosaminyl) asparagine amidase (PNGase F) mRNA, complete cds," [online]. Bethesda, MD [retrieved on May 9, 2018]. Retrieved from the Internet: ncbi.nlm.nih.gov/nuccore/J05449; 2 pgs.

National Center for Biotechnology Information, National Library of Medicine, National Institutes of Health, GenBank Locus PNGF_ELIMR, Accession No. P21163, "RecName: Full=Peptide-N(4)-(N-acetyl-beta-D-glucosaminyl) asparagine amidase F; Short=PNGase F; AltName: Full=Glycopeptide N-glycosidase; AltName: Full-N-glycanase Flags: Precursor," [online]. Bethesda, MD [retrieved on May 9, 2018]. Retrieved from the Internet: ncbi.nlm.nih.gov/protein/P21163; 7 pgs.

National Center for Biotechnology Information, National Library of Medicine, National Institutes of Health, GenBank Locus Q9XBM8_FLAME, Accession No. Q9XBM8, "Peptide: N-glycosidase F," [online], Bethesda, MD [retrieved on May 9, 2018]. Retrieved from the Internet: ncbi.nlm.nih.gov/protein/Q9XBM8; 1 pg.

Weisser et al., Glyco XX 20th International Symposium on Glycoconjugates, Abstract #78, Glycoconj. J. 2009, 26:763-898.

Office Action for Japanese Patent Application No. 2019-557612 dated Feb. 21, 2022, 19 pages including English translation.

Woods, Robert J, "Oral Candidasis: Antigen Structure and Vaccine Design," Grant Abstract, Grant No. DE013982 [online]. National Institute of Dental & Craniofacial Research, National Institutes of Health, project dates Sep. 29, 2000 to Jul. 31, 2004 [retrieved on Jan. 15, 2013], Retrieved from the Internet: projectreporter.nih.gov/pr_Prj_info_desc_dtls.cfm?aid=6286200&icde=14958427&ddparam=&ddvalue=&ddsub=&cr=10&csb=default&cs=ASC&print=yes; 2 pgs.

Woods, Robert J, "NMR & Molecular Dynamic Studies of Polysaccharides," Grant Abstract, Grant No. 2P41RR005351-16, Subproject 0095 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181442&icde=21876699&print=yes; 1 pg.

Woods, Robert J, "Development of the Amber Force Field," Grant Abstract, Grant No. 2P41RR005351-16, Subproject 0112 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181450&icde=21876699&ddparam=&ddvalue=&ddsub=&cr=70&csb=default&cs=ASC&print=yes; 1 pg.

Woods, Robert J, "Quantum NMR Methods for Analyzing Glycopeptide Structure & DYNAMICS," Grant Abstract, Grant No. 2P41RR005351-16, Subproject 0113 [online]. National Center For Research Resources, National Institutes of Health, project dates Apr. 4, 2015 to Jan. 31, 2006 [retrieved on Sep. 25, 2014]. Retrieved from the Internet: projectreporter.nih.gov/pr_Prj_info_desc_dtls.cfm?aid=7181451&icde=21876699&ddparam=&ddvalue=&ddsub=&cr=71&csb=default&cs=ASC&print=yes; 1 pg.

Woods, Robert J, "Genetic & Computational Analysis of Growth Factor," Grant Abstract, Grant No. 2P41RR005351-16, Subproject 0117 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181455&icde=21876699&ddparam=&ddvalue=&ddsub=&cr=75&csb=default&cs=ASC&print=yes; 1 pg.

Woods, Robert J, "Modeling the Mechanism of Enzyme Activity," Grant Abstract, Grant No. 2P41RR005351-16, Subproject 0137 [online], National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181456&icde=21876699&ddparam=&ddvalue=&ddsub=&cr=76&csb=default&cs=ASC&print=yes; 1 pg.

Woods, Robert J, "Computational Analysis of Carbohydrate & Protein," Grant Abstract, Grant No. 2P41RR005351-16, Subproject 0140 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?aid=7181457&icde=21876699&ddparam=&ddvalue=&ddsub=&cr=77&csb=default&cs=ASC&print=yes; 1 pg.

Woods, Robert J, "Analysis of Relationship Between Anomeric Configuration & Linkage Conformation," Grant Abstract, Grant No. 2P41RR005351-16, Subproject 0144 [online]. National Center For Research Resources, National Institutes of Health, project dates Apr. 4, 2005 to Jan. 31, 2006 [retrieved on Sep. 25, 2014]. Retrieved from the Internet: projectreporter.nih.gov/pr_Prj_info_desc_dtls.cfm?ai d=7181462&icde=21876699&ddparam=&ddvalue=&ddsub=&cr=78&csb=default&cs=ASC&print=yes; 1 pg.

* cited by examiner

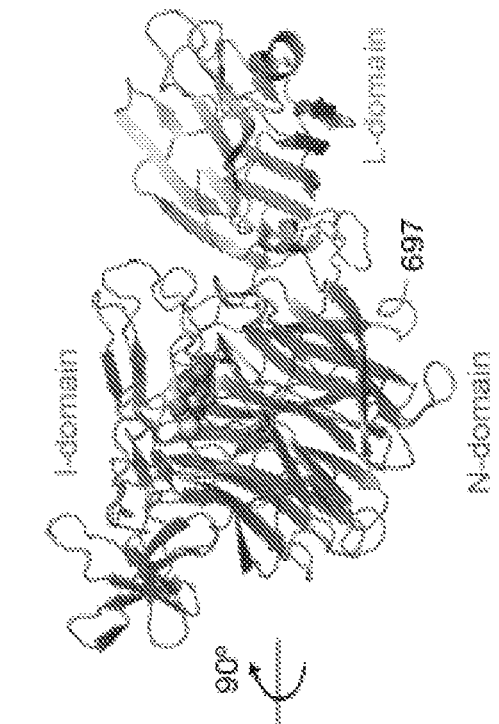
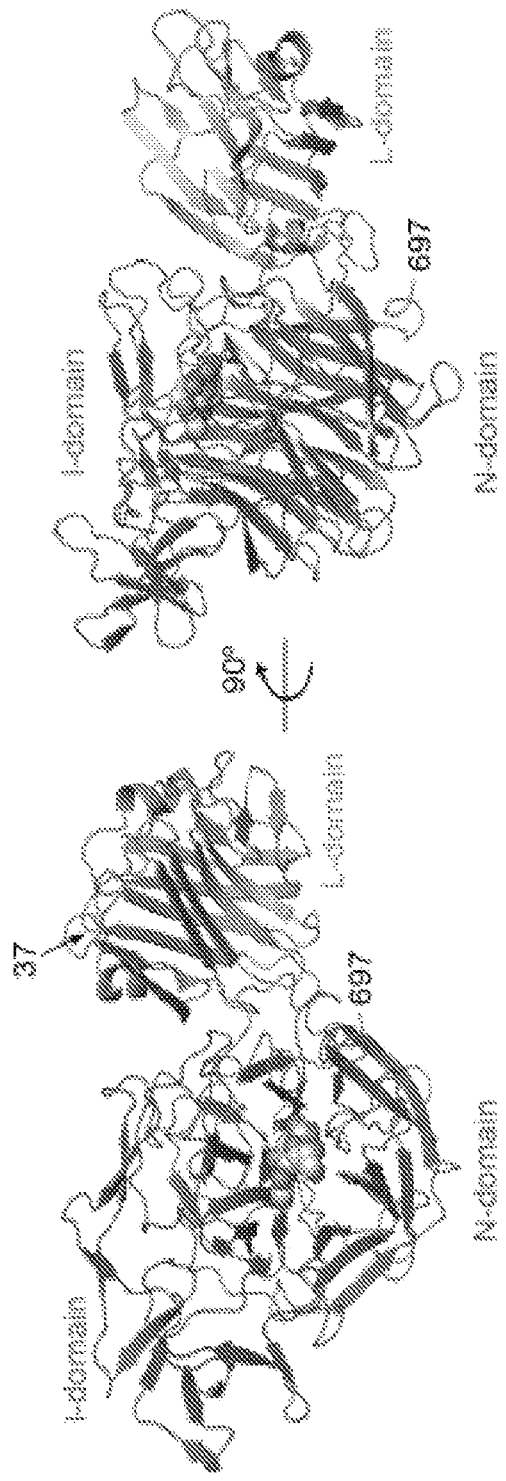
FIG. 1A
FIG. 1B

FIG. 3C

```
2VVZ:A|PDBID|CHAIN|SEQUENCE   ------------------------------------------------------------ 0
2VW0:A|PDBID|CHAIN|SEQUENCE   MNKPGLYSKLGISVVGISLLMGVPTLIHANELNYGQLSISPIFQGGSYQLNNKSIDISSL 60
5F9T:A|PDBID|CHAIN|SEQUENCE   ------------------------------------ETPVLEKNNVTLTGGGENVTKE 22

2VVZ:A|PDBID|CHAIN|SEQUENCE   ------------------------------------------------------------ 0
2VW0:A|PDBID|CHAIN|SEQUENCE   LLDKLSGESQTVVMKFKADKPNSLQALFGLSNSKAGFKNNYFSIFMRDSGEIGVEIRDAQ 120
5F9T:A|PDBID|CHAIN|SEQUENCE   LKDKFTSGDFTVVIKYNQSSEKGLQALFGISNSKPGQQNSYVEVFLRDNGELGMEARDTS 82

2VVZ:A|PDBID|CHAIN|SEQUENCE   ------------------------------------------------------------ 0
2VW0:A|PDBID|CHAIN|SEQUENCE   KGINYLFSRPASLWGKHKGQAVENTLVFVSDSKDKTYTMYVNGIEVFSETVDTFLPISNI 180
5F9T:A|PDBID|CHAIN|SEQUENCE   SNKNNLVSPPASVWGKYKQEAVTNTVAVVADSVKKTYSLYANGTKVVEKKVDNFLNIKDI 142

2VVZ:A|PDBID|CHAIN|SEQUENCE   ---------------------------EGAAL-------------TEKTDIFESGRNG 18
2VW0:A|PDBID|CHAIN|SEQUENCE   NGIDKATLGAVNREGKEHYLAKGSIDEISLFNKAISDQEVSTIPLS-NPFQLIFQSG---- 236
5F9T:A|PDBID|CHAIN|SEQUENCE   KGIDYYMLGGVKPAGKTAFGFNGTLENIKFFNSALDEETVKKMTTNAVTGHLIYTAN--- 199
                                                                              .*;    *: :.

2VVZ:A|PDBID|CHAIN|SEQUENCE   KPNKDGIKSYRIPALLKTDKGTLIAGADEPRLHSSDW-GDIGMVIRRSEDNGKTWGDRVT 77
2VW0:A|PDBID|CHAIN|SEQUENCE   ---DSTQANYFRIPTLYTLSSGRVLSSIDARYGGTHDSKSKINIATSYSDDNGKTWSEPIF 294
5F9T:A|PDBID|CHAIN|SEQUENCE   ---DTTGSNYFRIPVLYTFSNGRVFSSIDARYGGTHDFLNKINIATSYSDDNGKTWTKPKL 257
                                  :. :***.*  ..* ::: * * .. ..*.:: ..*:*******

2VVZ:A|PDBID|CHAIN|SEQUENCE   ITNLPD-----------NPKASDPSIGSPVNIDMVLVQDPETKRIFSIYDMFPEGKGIFG 126
2VW0:A|PDBID|CHAIN|SEQUENCE   AMKFNDYEEQLVVWPRDNKLKNSQISGSASFIDSSIVEDKKSGKTILLADVMPAGIGNN- 353
5F9T:A|PDBID|CHAIN|SEQUENCE   TLAFDDFAPVPLEWPREVGGRDLQISGGATYIDSVIVEKK-NKQVLMFADVMPAGVSFR- 315
                               :  *           .  *:   **  :*: . : : *:: * *.

2VVZ:A|PDBID|CHAIN|SEQUENCE   MSSQKEEAYRKIDGKTYQILYREGEK-GAYTIRENGTVYTPDGKA-TDYRVVV-------- 177
2VW0:A|PDBID|CHAIN|SEQUENCE   NANKADSGFKEINGHYYLKLKKNGDNDFRYTVPENGVVYNETTNKPTNYTINDKYEVLEG 413
5F9T:A|PDBID|CHAIN|SEQUENCE   EATRKDSGYKQIDGNYYLKLPKQGDTDYNYTIRENGTVYDDPTNRPTEFSVDKNFGIKQN 375
                               :.: :..:*:*:*: *  *  ::*:.  **:****.**   *:: :

2VVZ:A|PDBID|CHAIN|SEQUENCE   ------DP---VKPAYSDKGDLYKGNQLLGNIYFTTNKTSPFPIAKDSYLWMSYSDDDGKT 229
2VW0:A|PDBID|CHAIN|SEQUENCE   GKSLTVEQYSVDFDSGSLPERHNGKQVPMNVFY---KDSLFKVTPTNYIAMTTSQNRGES 470
5F9T:A|PDBID|CHAIN|SEQUENCE   GNYLTVEQYSVSFENNKKTEYRNGTKVHMNIFY---KDALFKVVPTNYIAYISSNDHGES 432
                                 :   *.   ..  : :*.:: *::: *    *:;  ,*:    *:: *::

2VVZ:A|PDBID|CHAIN|SEQUENCE   WSAPQDLTPMVKADWMKFLGVGPGTGIVLRNGPHKGRILIPVYTTNNVSHLNGSQSSRII 289
2VW0:A|PDBID|CHAIN|SEQUENCE   WEQFKLLPPFLGEKHN-GTYLCPGQGLALK----SSNRLIPATYTSGE---------LTYL 517
5F9T:A|PDBID|CHAIN|SEQUENCE   WSAPTLLPPIMGLNPN-APYLGPGPGIIES----STGRILIPSYTSKE---------SAFI 479
                              *.   * *:: *  ;   * **  *:      ..*:::  **  :

2VVZ:A|PDBID|CHAIN|SEQUENCE   YSDDHGKTWHAGEAVNDNRQVDGQKIHSSTMNNRRAQNTESTVVQLNNGDVKLFMRGLTG 349
2VW0:A|PDBID|CHAIN|SEQUENCE   ISDDSGQTWKKSSASIPF----------------KNATAEAQMVELRDGVIRTFFPTTTG 561
5F9T:A|PDBID|CHAIN|SEQUENCE   YSDDNGASWKVKVVPLPS---------------S--WSAEAQFVELSPGVIQAYMRTMNG 522
                              ***  *  ;*:             .  .:*: .*:*   * ::  ::*   .*

2VVZ:A|PDBID|CHAIN|SEQUENCE   DLQVATSKEGGVTWEKDIKRYP-QVKDVYVQMSA---IHTMHEGKEYIILSNAGGP-KREN 405
2VW0:A|PDBID|CHAIN|SEQUENCE   KIAYMTSRDSGETWSKVSYIDGIQQTSYGTQVSAIKYSQLIDGKEAVILSTPNSRSGPKG 621
5F9T:A|PDBID|CHAIN|SEQUENCE   KIAYLTSKDAGTTWSAPEYLKFVSNPSYGTQLSIINYSQLIDGKKAVILSTPNSTNGRKH 582
                               :  **:*.*  **.          . *:*   ;  ;  *:   **.*  .. *;

2VVZ:A|PDBID|CHAIN|SEQUENCE   GMVHLARV--EENGELTWLKHNPIQKG---EFAYNSLQELGNGEYGILYEHTEKGQN-AYT- 460
2VW0:A|PDBID|CHAIN|SEQUENCE   GQLVVGLVNKEDDSIDWKYHYDIDLPSYGAYSAITELPNHHIGVLFEKYDSWSPNELHL 681
5F9T:A|PDBID|CHAIN|SEQUENCE   GQIWIGLTND-DNTIDWRYHHDVDYSNYGYSYSTLTELPNHEIGLMFEKFDSWSRNELRM 641
                              * ::  :.  :  :  * ::    ::*.:: ** *. *::**:  :.. ..

2VVZ:A|PDBID|CHAIN|SEQUENCE   ---LSFPKFNWDFLSKDLISPTEAKVFPTREMGKGVIGLEFDSEVLV       504
2VW0:A|PDBID|CHAIN|SEQUENCE   SNVVQYIDLEINDLTK--------------------------------      697
5F9T:A|PDBID|CHAIN|SEQUENCE   KNVVPYITFKIEDLKKNL------------------------------      659
                              ::  ::  *.*
```

FIG. 3D

```
2VW0:A|PDBID|CHAIN|SEQUENCE      MNKRGLYSKLGISVVGISLLMGVPTLIHANELNYGQLSISPIFQGGSYQLNNKSIDISSL 60
NanB:AA30-697(pET28a)            ------------------------------NELNYGQLSISPIFQGGSYQLNNKSIDISSL 31
                                                               ******************************

2VW0:A|PDBID|CHAIN|SEQUENCE      LLDKLSGESQTVVMKFKADKPNSLQALFGLSNSKAGFKNNYFSIFMRDSGEIGVEIRDAQ 120
NanB:AA30-697(pET28a)            LLDKLSGESQTVVMKFKADKPNSLQALFGLSNSKAGFKNNYFSIFMRDSGEIGVEIRDAQ 91
                                 ************************************************************

2VW0:A|PDBID|CHAIN|SEQUENCE      KGINYLFSRPASLWGKHKGQAVENTLVFVSDSKDKTYTMYVNGIEVFSETVDTFLPISNI 180
NanB:AA30-697(pET28a)            KGINYLFSRPASLWGKHKGQAVENTLVFVSDSKDKTYTMYVNGIEVFSETVDTFLPISNI 151
                                 ************************************************************

2VW0:A|PDBID|CHAIN|SEQUENCE      NGIDKATLGAVNREGKERYLAKGSIDEISLFNKAISDQEVSTIPLSNPFQLIFQSGDSTQ 240
NanB:AA30-697(pET28a)            NGIDKATLGAVNREGKERYLAKGSIDEISLFNKAISDQEVSTIPLSNPFQLIFQSGDSTQ 211
                                 ************************************************************

2VW0:A|PDBID|CHAIN|SEQUENCE      ANYFPIPTLYTLSSGRVLSSIDARYGGTHDSKSKINIATSYSDDNGKTWSEPIFAMKFND 300
NanB:AA30-697(pET28a)            ANYFRIPTLYTLSSGRVLSSIDARYGGTHDSKSKINIATSYSDDNGKTWSEPIFAMKFND 271
                                 **** *******************************************************

2VW0:A|PDBID|CHAIN|SEQUENCE      YEEQLVYWPRDNKLKNSQISGSASFIDSSIVEDKKSGKTILLADVMPAGIGNNNANKADS 360
NanB:AA30-697(pET28a)            YEEQLVYWPRDNKLKNSQISGSASFIDSSIVEDKKSGKTILLADVMPAGIGNNNANKADS 331
                                 ************************************************************

2VW0:A|PDBID|CHAIN|SEQUENCE      GFKEINGHYYLKLKKNGDNDFRYTVRENGVVYNETTNKPTNYTINDKYEVLEGGKSLTVE 420
NanB:AA30-697(pET28a)            GFKEINGHYYLKLKKNGDNDFRYTVRENGVVYNETTNKPTNYTINDKYEVLEGGKSLTVE 391
                                 ************************************************************

2VW0:A|PDBID|CHAIN|SEQUENCE      QYSVDFDSGSLPERHNGKQVPMNVFYKDSLFKVTPTNYIAMTTSQNRGESWEQFKLLPPF 480
NanB:AA30-697(pET28a)            QYSVDFDSGSLREPHNGKQVPMNVFYKDSLFKVTPTNYIAMTTSQNRGESWEQFKLLPPF 451
                                 ************************************************************

2VW0:A|PDBID|CHAIN|SEQUENCE      LGEKHNGTYLCPGQGLALKSSNRLIFATYTSGELTYLISDDSGQTWKKSSASIPFKNATA 540
NanB:AA30-697(pET28a)            LGEKHNGTYLCPGQGLALKSSNRLIFATYTSGELTYLISDDSGQTWKKSSASIPFKNATA 511
                                 ************************************************************

2VW0:A|PDBID|CHAIN|SEQUENCE      EAQMVELRDGVIRTFFRTTTGKIAYMTSRDSGETWSKVSYIDGIQQTSYGTQVSAIKYSQ 600
NanB:AA30-697(pET28a)            EAQMVELRDGVIPTFFRTTTGKIAYMTSPDSGETWSKVSYIDGIQQTSYGTQVSAIKYSQ 571
                                 ************************************************************

2VW0:A|PDBID|CHAIN|SEQUENCE      LIDGKEAVILSTPNSRSGPKGGQLVVGLVNKEDDSIDWKYHYDIDLPSYGYAYSAITELP 660
NanB:AA30-697(pET28a)            LIDGKEAVILSTPNSRSGRKGGQLVVGLVNKEDDSIDWKYHYDIDLPSYGYAYSAITELP 631
                                 ************************************************************

2VW0:A|PDBID|CHAIN|SEQUENCE      NHHIGVLFEKYDSWSRNELHLSNVVQYIDLEINDLTK            697
NanB:AA30-697(pET28a)            NHHIGVLFEKYDSWSRNELHLSNVVQYIDLEINDLTK            668
                                 ************************************
```

Alignments made using Clustal Omega Multiple Sequence Alignment web tool:
https://www.ebi.ac.uk/Tools/msa/clustalo/

PDB = Research Collaboratory for Structural Bioinformatics Protein Database:
http://www.rcsb.org/pdb/home/home.do

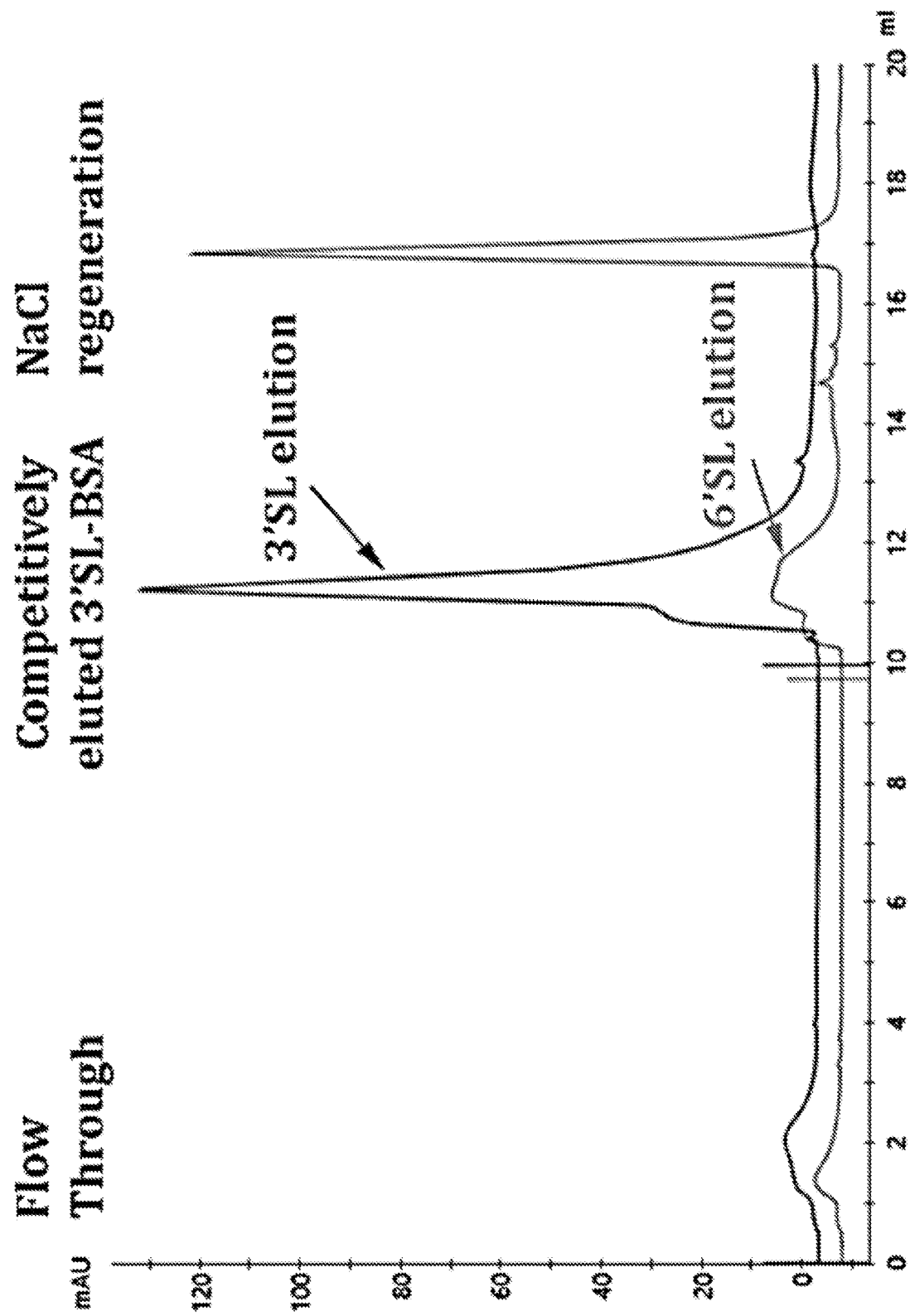

SEQUENCE LISTING

```
<160> NUMBER OF SEQ ID NOS: 4

<210> SEQ ID NO 1
<211> LENGTH: 697
<212> TYPE: PRT
<213> ORGANISM: streptococcus pneumoniae

<400> SEQUENCE: 1

Met Asn Lys Arg Gly Leu Tyr Ser Lys Leu Gly Ile Ser Val Val Gly
1               5                   10                  15

Ile Ser Leu Leu Met Gly Val Pro Thr Leu Ile His Ala Asn Glu Leu
            20                  25                  30

Asn Tyr Gly Gln Leu Ser Ile Ser Pro Ile Phe Gln Gly Gly Ser Tyr
        35                  40                  45

Gln Leu Asn Asn Lys Ser Ile Asp Ile Ser Ser Leu Leu Leu Asp Lys
    50                  55                  60

Leu Ser Gly Glu Ser Gln Thr Val Val Met Lys Phe Lys Ala Asp Lys
65                  70                  75                  80

Pro Asn Ser Leu Gln Ala Leu Phe Gly Leu Ser Asn Ser Lys Ala Gly
                85                  90                  95

Phe Lys Asn Asn Tyr Phe Ser Ile Phe Met Arg Asp Ser Gly Glu Ile
            100                 105                 110

Gly Val Glu Ile Arg Asp Ala Gln Lys Gly Ile Asn Tyr Leu Phe Ser
        115                 120                 125

Arg Pro Ala Ser Leu Trp Gly Lys His Lys Gly Gln Ala Val Glu Asn
    130                 135                 140

Thr Leu Val Phe Val Ser Asp Ser Lys Asp Lys Thr Tyr Thr Met Tyr
145                 150                 155                 160

Val Asn Gly Ile Glu Val Phe Ser Glu Thr Val Asp Thr Phe Leu Pro
                165                 170                 175

Ile Ser Asn Ile Asn Gly Ile Asp Lys Ala Thr Leu Gly Ala Val Asn
            180                 185                 190

Arg Glu Gly Lys Glu His Tyr Leu Ala Lys Gly Ser Ile Asp Glu Ile
        195                 200                 205

Ser Leu Phe Asn Lys Ala Ile Ser Asp Gln Glu Val Ser Thr Ile Pro
    210                 215                 220

Leu Ser Asn Pro Phe Gln Leu Ile Phe Gln Ser Gly Asp Ser Thr Gln
225                 230                 235                 240
```

```
Ala Asn Tyr Phe Arg Ile Pro Thr Leu Tyr Thr Leu Ser Ser Gly Arg
            245                 250                 255

Val Leu Ser Ser Ile Asp Ala Arg Tyr Gly Gly Thr His Asp Ser Lys
            260                 265                 270

Ser Lys Ile Asn Ile Ala Thr Ser Tyr Ser Asp Asp Asn Gly Lys Thr
            275                 280                 285

Trp Ser Glu Pro Ile Phe Ala Met Lys Phe Asn Asp Tyr Glu Glu Gln
            290                 295                 300

Leu Val Tyr Trp Pro Arg Asp Asn Lys Leu Lys Asn Ser Gln Ile Ser
305                 310                 315                 320

Gly Ser Ala Ser Phe Ile Asp Ser Ile Val Glu Asp Lys Lys Ser
            325                 330                 335

Gly Lys Thr Ile Leu Leu Ala Asp Val Met Pro Ala Gly Ile Gly Asn
            340                 345                 350

Asn Asn Ala Asn Lys Ala Asp Ser Gly Phe Lys Glu Ile Asn Gly His
            355                 360                 365

Tyr Tyr Leu Lys Leu Lys Lys Asn Gly Asp Asn Asp Phe Arg Tyr Thr
    370                 375                 380

Val Arg Glu Asn Gly Val Val Tyr Asn Glu Thr Thr Asn Lys Pro Thr
385                 390                 395                 400

Asn Tyr Thr Ile Asn Asp Lys Tyr Glu Val Leu Glu Gly Gly Lys Ser
            405                 410                 415

Leu Thr Val Glu Gln Tyr Ser Val Asp Phe Asp Ser Gly Ser Leu Arg
            420                 425                 430

Glu Arg His Asn Gly Lys Gln Val Pro Met Asn Val Phe Tyr Lys Asp
            435                 440                 445

Ser Leu Phe Lys Val Thr Pro Thr Asn Tyr Ile Ala Met Thr Thr Ser
    450                 455                 460

Gln Asn Arg Gly Glu Ser Trp Glu Gln Phe Lys Leu Leu Pro Pro Phe
465                 470                 475                 480

Leu Gly Glu Lys His Asn Gly Thr Tyr Leu Cys Pro Gly Gln Gly Leu
            485                 490                 495

Ala Leu Lys Ser Ser Asn Arg Leu Ile Phe Ala Thr Tyr Thr Ser Gly
            500                 505                 510

Glu Leu Thr Tyr Leu Ile Ser Asp Asp Ser Gly Gln Thr Trp Lys Lys
            515                 520                 525

Ser Ser Ala Ser Ile Pro Phe Lys Asn Ala Thr Ala Glu Ala Gln Met
    530                 535                 540

Val Glu Leu Arg Asp Gly Val Ile Arg Thr Phe Phe Arg Thr Thr Thr
545                 550                 555                 560

Gly Lys Ile Ala Tyr Met Thr Ser Arg Asp Ser Gly Glu Thr Trp Ser
            565                 570                 575

Lys Val Ser Tyr Ile Asp Gly Ile Gln Gln Thr Ser Tyr Gly Thr Gln
            580                 585                 590

Val Ser Ala Ile Lys Tyr Ser Gln Leu Ile Asp Gly Lys Glu Ala Val
            595                 600                 605

Ile Leu Ser Thr Pro Asn Ser Arg Ser Arg Lys Gly Gly Gln Leu
            610                 615                 620

Val Val Gly Leu Val Asn Lys Glu Asp Asp Ser Ile Asp Trp Lys Tyr
625                 630                 635                 640

His Tyr Asp Ile Asp Leu Pro Ser Tyr Gly Tyr Ala Tyr Ser Ala Ile
            645                 650                 655
```

```
Thr Glu Leu Pro Asn His His Ile Gly Val Leu Phe Glu Lys Tyr Asp
            660                 665                 670

Ser Trp Ser Arg Asn Glu Leu His Leu Ser Asn Val Val Gln Tyr Ile
        675                 680                 685

Asp Leu Glu Ile Asn Asp Leu Thr Lys
    690                 695

<210> SEQ ID NO 2
<211> LENGTH: 504
<212> TYPE: PRT
<213> ORGANISM: streptococcus pneumoniae

<400> SEQUENCE: 2

Glu Gly Ala Ala Leu Thr Glu Lys Thr Asp Ile Phe Glu Ser Gly Arg
1               5                   10                  15

Asn Gly Lys Pro Asn Lys Asp Gly Ile Lys Ser Tyr Arg Ile Pro Ala
            20                  25                  30

Leu Leu Lys Thr Asp Lys Gly Thr Leu Ile Ala Gly Ala Asp Glu Arg
        35                  40                  45

Arg Leu His Ser Ser Asp Trp Gly Asp Ile Gly Met Val Ile Arg Arg
    50                  55                  60

Ser Glu Asp Asn Gly Lys Thr Trp Gly Asp Arg Val Thr Ile Thr Asn
65                  70                  75                  80

Leu Arg Asp Asn Pro Lys Ala Ser Asp Pro Ser Ile Gly Ser Pro Val
                85                  90                  95

Asn Ile Asp Met Val Leu Val Gln Asp Pro Glu Thr Lys Arg Ile Phe
            100                 105                 110

Ser Ile Tyr Asp Met Phe Pro Glu Gly Lys Gly Ile Phe Gly Met Ser
        115                 120                 125

Ser Gln Lys Glu Glu Ala Tyr Lys Lys Ile Asp Gly Lys Thr Tyr Gln
    130                 135                 140

Ile Leu Tyr Arg Glu Gly Glu Lys Gly Ala Tyr Thr Ile Arg Glu Asn
145                 150                 155                 160

Gly Thr Val Tyr Thr Pro Asp Gly Lys Ala Thr Asp Tyr Arg Val Val
                165                 170                 175

Val Asp Pro Val Lys Pro Ala Tyr Ser Asp Lys Gly Asp Leu Tyr Lys
            180                 185                 190

Gly Asn Gln Leu Leu Gly Asn Ile Tyr Phe Thr Thr Asn Lys Thr Ser
        195                 200                 205

Pro Phe Arg Ile Ala Lys Asp Ser Tyr Leu Trp Met Ser Tyr Ser Asp
    210                 215                 220

Asp Asp Gly Lys Thr Trp Ser Ala Pro Gln Asp Ile Thr Pro Met Val
225                 230                 235                 240

Lys Ala Asp Trp Met Lys Phe Leu Gly Val Gly Pro Gly Thr Gly Ile
                245                 250                 255

Val Leu Arg Asn Gly Pro His Lys Gly Arg Ile Leu Ile Pro Val Tyr
            260                 265                 270

Thr Thr Asn Asn Val Ser His Leu Asn Gly Ser Gln Ser Ser Arg Ile
        275                 280                 285

Ile Tyr Ser Asp Asp His Gly Lys Thr Trp His Ala Gly Glu Ala Val
    290                 295                 300

Asn Asp Asn Arg Gln Val Asp Gly Gln Lys Ile His Ser Ser Thr Met
305                 310                 315                 320

Asn Asn Arg Arg Ala Gln Asn Thr Glu Ser Thr Val Val Gln Leu Asn
                325                 330                 335
```

```
Asn Gly Asp Val Lys Leu Phe Met Arg Gly Leu Thr Gly Asp Leu Gln
            340                 345                 350

Val Ala Thr Ser Lys Asp Gly Val Thr Trp Glu Lys Asp Ile Lys
            355                 360                 365

Arg Tyr Pro Gln Val Lys Asp Val Tyr Val Gln Met Ser Ala Ile His
            370                 375                 380

Thr Met His Glu Gly Lys Glu Tyr Ile Ile Leu Ser Asn Ala Gly Gly
385                 390                 395                 400

Pro Lys Arg Glu Asn Gly Met Val His Leu Ala Arg Val Glu Glu Asn
            405                 410                 415

Gly Glu Leu Thr Trp Leu Lys His Asn Pro Ile Gln Lys Gly Glu Phe
            420                 425                 430

Ala Tyr Asn Ser Leu Gln Glu Leu Gly Asn Gly Glu Tyr Gly Ile Leu
            435                 440                 445

Tyr Glu His Thr Glu Lys Gly Gln Asn Ala Tyr Thr Leu Ser Phe Arg
            450                 455                 460

Lys Phe Asn Trp Asp Phe Leu Ser Lys Asp Leu Ile Ser Pro Thr Glu
465                 470                 475                 480

Ala Lys Val Lys Arg Thr Arg Glu Met Gly Lys Gly Val Ile Gly Leu
            485                 490                 495

Glu Phe Asp Ser Glu Val Leu Val
            500

<210> SEQ ID NO 3
<211> LENGTH: 659
<212> TYPE: PRT
<213> ORGANISM: streptococcus pneumoniae

<400> SEQUENCE: 3

Glu Thr Pro Val Leu Glu Lys Asn Asn Val Thr Leu Thr Gly Gly Gly
1               5                   10                  15

Glu Asn Val Thr Lys Glu Leu Lys Asp Lys Phe Thr Ser Gly Asp Phe
            20                  25                  30

Thr Val Val Ile Lys Tyr Asn Gln Ser Ser Glu Lys Gly Leu Gln Ala
            35                  40                  45

Leu Phe Gly Ile Ser Asn Ser Lys Pro Gly Gln Gln Asn Ser Tyr Val
    50                  55                  60

Asp Val Phe Leu Arg Asp Asn Gly Glu Leu Gly Met Glu Ala Arg Asp
65                  70                  75                  80

Thr Ser Ser Asn Lys Asn Asn Leu Val Ser Arg Pro Ala Ser Val Trp
                85                  90                  95

Gly Lys Tyr Lys Gln Glu Ala Val Thr Asn Thr Val Ala Val Ala
            100                 105                 110

Asp Ser Val Lys Lys Thr Tyr Ser Leu Tyr Ala Asn Gly Thr Lys Val
            115                 120                 125

Val Glu Lys Lys Val Asp Asn Phe Leu Asn Ile Lys Asp Ile Lys Gly
            130                 135                 140

Ile Asp Tyr Tyr Met Leu Gly Val Lys Arg Ala Gly Lys Thr Ala
145                 150                 155                 160

Phe Gly Phe Asn Gly Thr Leu Glu Asn Ile Lys Phe Phe Asn Ser Ala
                165                 170                 175

Leu Asp Glu Glu Thr Val Lys Lys Met Thr Thr Asn Ala Val Thr Gly
            180                 185                 190

His Leu Ile Tyr Thr Ala Asn Asp Thr Thr Gly Ser Asn Tyr Phe Arg
```

```
            195                 200                 205
Ile Pro Val Leu Tyr Thr Phe Ser Asn Gly Arg Val Phe Ser Ser Ile
210                 215                 220

Asp Ala Arg Tyr Gly Gly Thr His Asp Phe Leu Asn Lys Ile Asn Ile
225                 230                 235                 240

Ala Thr Ser Tyr Ser Asp Asn Gly Lys Thr Trp Thr Lys Pro Lys
            245                 250                 255

Leu Thr Leu Ala Phe Asp Asp Phe Ala Pro Val Pro Leu Glu Trp Pro
                260                 265                 270

Arg Glu Val Gly Gly Arg Asp Leu Gln Ile Ser Gly Gly Ala Thr Tyr
            275                 280                 285

Ile Asp Ser Val Ile Val Glu Lys Lys Asn Lys Gln Val Leu Met Phe
290                 295                 300

Ala Asp Val Met Pro Ala Gly Val Ser Phe Arg Glu Ala Thr Arg Lys
305                 310                 315                 320

Asp Ser Gly Tyr Lys Gln Ile Asp Gly Asn Tyr Tyr Leu Lys Leu Arg
            325                 330                 335

Lys Gln Gly Asp Thr Asp Tyr Asn Tyr Thr Ile Arg Glu Asn Gly Thr
                340                 345                 350

Val Tyr Asp Asp Arg Thr Asn Arg Pro Thr Glu Phe Ser Val Asp Lys
            355                 360                 365

Asn Phe Gly Ile Lys Gln Asn Gly Asn Tyr Leu Thr Val Glu Gln Tyr
370                 375                 380

Ser Val Ser Phe Glu Asn Asn Lys Lys Thr Glu Tyr Arg Asn Gly Thr
385                 390                 395                 400

Lys Val His Met Asn Ile Phe Tyr Lys Asp Ala Leu Phe Lys Val Val
                405                 410                 415

Pro Thr Asn Tyr Ile Ala Tyr Ile Ser Ser Asn Asp His Gly Glu Ser
            420                 425                 430

Trp Ser Ala Pro Thr Leu Leu Pro Pro Ile Met Gly Leu Asn Arg Asn
            435                 440                 445

Ala Pro Tyr Leu Gly Pro Gly Arg Gly Ile Ile Glu Ser Ser Thr Gly
450                 455                 460

Arg Ile Leu Ile Pro Ser Tyr Thr Gly Lys Glu Ser Ala Phe Ile Tyr
465                 470                 475                 480

Ser Asp Asp Asn Gly Ala Ser Trp Lys Val Lys Val Pro Leu Pro
            485                 490                 495

Ser Ser Trp Ser Ala Glu Ala Gln Phe Val Glu Leu Ser Pro Gly Val
            500                 505                 510

Ile Gln Ala Tyr Met Arg Thr Asn Asn Gly Lys Ile Ala Tyr Leu Thr
            515                 520                 525

Ser Lys Asp Ala Gly Thr Thr Trp Ser Ala Pro Glu Tyr Leu Lys Phe
            530                 535                 540

Val Ser Asn Pro Ser Tyr Gly Thr Gln Leu Ser Ile Ile Asn Tyr Ser
545                 550                 555                 560

Gln Leu Ile Asp Gly Lys Lys Ala Val Ile Leu Ser Thr Pro Asn Ser
                565                 570                 575

Thr Asn Gly Arg Lys His Gly Gln Ile Trp Ile Gly Leu Ile Asn Asp
            580                 585                 590

Asp Asn Thr Ile Asp Trp Arg Tyr His His Asp Val Asp Tyr Ser Asn
            595                 600                 605

Tyr Gly Tyr Ser Tyr Ser Thr Leu Thr Glu Leu Pro Asn His Glu Ile
610                 615                 620
```

Gly Leu Met Phe Glu Lys Phe Asp Ser Trp Ser Arg Asn Glu Leu His
625                 630                 635                 640

Met Lys Asn Val Val Pro Tyr Ile Thr Phe Lys Ile Glu Asp Leu Lys
            645                 650                 655

Lys Asn Leu

<210> SEQ ID NO 4
<211> LENGTH: 663
<212> TYPE: PRT
<213> ORGANISM: streptococcus pneumoniae

<400> SEQUENCE: 4

Asn Glu Leu Asn Tyr Gly Gln Leu Ser Ile Ser Pro Ile Phe Gln Gly
1               5                   10                  15

Gly Ser Tyr Gln Leu Asn Asn Lys Ser Ile Asp Ile Ser Ser Leu Leu
                20                  25                  30

Leu Asp Lys Leu Ser Gly Glu Ser Gln Thr Val Val Met Lys Phe Lys
            35                  40                  45

Ala Asp Lys Pro Asn Ser Leu Gln Ala Leu Phe Gly Leu Ser Asn Ser
        50                  55                  60

Lys Ala Gly Phe Lys Asn Asn Tyr Phe Ser Ile Phe Met Arg Asp Ser
65                  70                  75                  80

Gly Glu Ile Gly Val Glu Ile Arg Asp Ala Gln Lys Gly Ile Asn Tyr
                85                  90                  95

Leu Phe Ser Arg Pro Ala Ser Leu Trp Gly Lys His Lys Gly Gln Ala
            100                 105                 110

Val Glu Asn Thr Leu Val Phe Val Ser Asp Ser Lys Asp Lys Thr Tyr
        115                 120                 125

Thr Met Tyr Val Asn Gly Ile Glu Val Phe Ser Glu Thr Val Asp Thr
130                 135                 140

Phe Leu Pro Ile Ser Asn Ile Asn Gly Ile Asp Lys Ala Thr Leu Gly
145                 150                 155                 160

Ala Val Asn Arg Glu Gly Lys Glu His Tyr Leu Ala Lys Gly Ser Ile
                165                 170                 175

Asp Glu Ile Ser Leu Phe Asn Lys Ala Ile Ser Asp Gln Glu Val Ser
            180                 185                 190

Thr Ile Pro Leu Ser Asn Pro Phe Gln Leu Ile Phe Gln Ser Gly Asp
        195                 200                 205

Ser Thr Gln Ala Asn Tyr Phe Arg Ile Pro Thr Leu Tyr Thr Leu Ser
210                 215                 220

Ser Gly Arg Val Leu Ser Ser Ile Asp Ala Arg Tyr Gly Gly Thr His
225                 230                 235                 240

Asp Ser Lys Ser Lys Ile Asn Ile Ala Thr Ser Tyr Ser Asp Asp Asn
                245                 250                 255

Gly Lys Thr Trp Ser Glu Pro Ile Phe Ala Met Lys Phe Asn Asp Tyr
            260                 265                 270

Glu Glu Gln Leu Val Tyr Trp Pro Arg Asp Asn Lys Leu Lys Asn Ser
        275                 280                 285

Gln Ile Ser Gly Ser Ala Ser Phe Ile Asp Ser Ser Ile Val Glu Asp
    290                 295                 300

Lys Lys Ser Gly Lys Thr Ile Leu Leu Ala Asp Val Met Pro Ala Gly
305                 310                 315                 320

Ile Gly Asn Asn Asn Ala Asn Lys Ala Asp Ser Gly Phe Lys Glu Ile
                325                 330                 335

```
Asn Gly His Tyr Tyr Leu Lys Leu Lys Lys Asn Gly Asp Asn Asp Phe
            340             345             350
Arg Tyr Thr Val Arg Glu Asn Gly Val Val Tyr Asn Glu Thr Thr Asn
            355             360             365
Lys Pro Thr Asn Tyr Thr Ile Asn Asp Lys Tyr Glu Val Leu Glu Gly
            370             375             380
Gly Lys Ser Leu Thr Val Glu Gln Tyr Ser Val Asp Phe Asp Ser Gly
385             390             395             400
Ser Leu Arg Glu Arg His Asn Gly Lys Gln Val Pro Met Asn Val Phe
            405             410             415
Tyr Lys Asp Ser Leu Phe Lys Val Thr Pro Thr Asn Tyr Ile Ala Met
            420             425             430
Thr Thr Ser Gln Asn Arg Gly Glu Ser Trp Glu Gln Phe Lys Leu Leu
            435             440             445
Pro Pro Phe Leu Gly Glu Lys His Asn Gly Thr Tyr Leu Cys Pro Gly
    450             455             460
Gln Gly Leu Ala Leu Lys Ser Ser Asn Arg Leu Ile Phe Ala Thr Tyr
465             470             475             480
Thr Ser Gly Glu Leu Thr Tyr Leu Ile Ser Asp Asp Ser Gly Gln Thr
            485             490             495
Trp Lys Lys Ser Ser Ala Ser Ile Pro Phe Lys Asn Ala Thr Ala Glu
            500             505             510
Ala Gln Met Val Glu Leu Arg Asp Gly Val Ile Arg Thr Phe Phe Arg
            515             520             525
Thr Thr Thr Gly Lys Ile Ala Tyr Met Thr Ser Arg Asp Ser Gly Glu
            530             535             540
Thr Trp Ser Lys Val Ser Tyr Ile Asp Gly Ile Gln Gln Thr Ser Tyr
545             550             555             560
Gly Thr Gln Val Ser Ala Ile Lys Tyr Ser Gln Leu Ile Asp Gly Lys
                565             570             575
Glu Ala Val Ile Leu Ser Thr Pro Asn Ser Arg Ser Gly Arg Lys Gly
            580             585             590
Gly Gln Leu Val Val Gly Leu Val Asn Lys Glu Asp Asp Ser Ile Asp
            595             600             605
Trp Lys Tyr His Tyr Asp Ile Asp Leu Pro Ser Tyr Gly Tyr Ala Tyr
            610             615             620
Ser Ala Ile Thr Glu Leu Pro Asn His His Ile Gly Val Leu Phe Glu
625             630             635             640
Lys Tyr Asp Ser Trp Ser Arg Asn Glu Leu His Leu Ser Asn Val Val
            645             650             655
Gln Tyr Ile Asp Leu Glu Ile
            660
```

SIALIC ACID BINDING POLYPEPTIDE

CROSS-REFERENCE TO RELATED APPLICATIONS

This application is the § 371 U.S. National Stage of International Application No. PCT/US2018/029079, filed Apr. 24, 2018, which claims the benefit of U.S. Provisional Application Ser. No. 62/489,243, filed Apr. 24, 2017, the disclosures of which are incorporated by reference herein in their entireties.

GOVERNMENT FUNDING

This invention was made with government support under Grant No. R41GM113351 awarded by National Institutes of Health. The government has certain rights in the invention.

SEQUENCE LISTING

This application contains a Sequence Listing electronically submitted via EFS-Web to the United States Patent and Trademark Office as an ASCII text file entitled "Seq-List-02740201_ST25.txt" having a size of 22 kilobytes and created on Apr. 16, 2018. The information contained in the Sequence Listing is incorporated by reference herein.

BACKGROUND

Glycans have several distinct properties that make their development as disease biomarkers appealing. Their location on cell surfaces makes them the first point of contact for cellular interactions and thus they are crucial in the control of normal metabolic processes. They also function as pathogen adhesion receptors. Glycan structures that are absent or are present in low amounts in a normal state on glycoprotein can proliferate or alter their sequence in disease states. A distinguishing feature of many glycans is a terminal sialic acid.

SUMMARY OF THE INVENTION

The present invention provides novel sialic acid-recognizing affinity reagents. The affinity reagents recognize, and bind to, sialic acid (also referred to as 5-(acetylamino)-3,5-dideoxy-D-glycero-αD-galacto-non-2-ulopyranosonic acid, Neu5Ac, N-acetyl neuraminic acid, NANA, and Sia) that is present on a glycosylated biomolecule, such as a glycoprotein, glycopeptide, glycolipid, oligosaccharide, or polysaccharide.

The sialic acid-recognizing affinity reagents provided herein are engineered Lectenz®-type proteins that have affinity and specificity for sialylated glycans. Lectenz® is a registered trademark of Glycosensors and Diagnostics (d/b/a Lectenz® Bio). Embodiments of the engineered sialic acid-recognizing affinity reagent of the invention include, without limitation: 1) pan-specific sialic acid-recognizing affinity reagents with broad specificity for sialo-glycans independent of linkage (α2,3-, α2,6-, and α2,8-linkages) (referred to herein as a Sia-PS reagent), with a lead candidate Sia-PS1, described in Example I; and 2) α2,3 sialic acid-recognizing affinity reagents specific for α2,3-linked sialo-glycans over α2,6, and α2,8 linkages (referred to herein as a Sia-3S reagent) with a lead candidate, Sia-3S1, described in Example II. These reagents have low or no affinity for non-sialylated glycans or peptide backbones.

Advantageously, the sialic acid-recognizing affinity reagents of the invention have enhanced substrate specificity compared to antibodies or lectins that bind to sialic acid. The substrate specificity is tunable, as evidenced by comparing the Sia-PS affinity reagents and the Sia-3 S affinity reagents described herein. Substrate specificity need not be context dependent, and the affinity reagents may be evolved to have desirable binding kinetics. Conveniently, the affinity reagents of the invention can be as efficiently produced as monomeric proteins.

In some embodiments, structurally guided genetic manipulations of *S. pneumoniae* NanB carbohydrate processing enzyme were used to identify sites for mutation, and select mutants with enhanced affinity for sialic acid, thereby converting NanB into a high specificity affinity reagent, known as a Lectenz®. Design and synthesis methods are described, in general, in US Pat. Pub. US2012/0040474 ("Glycan-Specific Analytical Tools") and WO2015/161201 (U.S. Ser. No. 15/304,725), each of which is explicitly incorporated by reference, and more specifically in Examples I and II below. However, it should be understood that the invention, as it relates to the various and particular sialic acid-recognizing affinity reagents identified and described herein, is not limited in any way by the method of making such reagents.

The sialic acid-recognizing affinity reagent of the invention is useful in both research and clinical settings. For example, it is useful for the detection of disease related sialic acid modifications of glycopeptides and glycoproteins. The affinity reagent may be employed as a capture reagent or recognition element in a variety of applications for the discovery of glycan-based disease markers, as well as in the quality control analysis of recombinantly produced biopharmaceuticals, many of which are glycoproteins such as antibodies. These reagents can be adapted for such platforms as affinity chromatography enrichment, Western blot, or FACS-based detection.

BRIEF DESCRIPTION OF THE FIGURES

FIG. 1 shows a three-dimensional representation of *S. pneumoniae* NanB. FIG. 1B is rotated 90 degrees from the view of FIG. 1A. In these images, NanB is shown in complex with a substrate, 2,7-anhydro-Neu5Ac, shown as a sphere, bound to the NanB active site. Gut et al., FEBS Lett., 2008, 582(23-24):2248-3352.

FIG. 3C shows an alignment of amino acid sequences of NanA (PDB ID 2VVZ; SEQ ID NO:2), NanB (PDB ID 2VW0; SEQ ID NO:1), and NanC (PDB ID 5F9T; SEQ ID NO:3). NanB and NanC have 50% sequence identity and both share 25% identity with NanA. "*" refers to fully conserved; ":" refers to conservation between groups of amino acids with strongly similar properties; and "." refers to conservation between groups of amino acids with weakly similar properties.

FIG. 3D shows an alignment of wild-type NanB (PDB ID 2VW0; SEQ ID NO:1) with the NanB fragment (30-697; SEQ ID NO:4) that is expressed from a pET28a+ based plasmid ("NanB:AA30-697(pET28a)") in Example I. Residues 1-29 in wild-type NanB represent a signal or leader sequence. "*" refers to fully conserved; ":" refers to conservation between groups of amino acids with strongly similar properties; and "." refers to conservation between groups of amino acids with weakly similar properties.

FIGS. 7A, 6B, and 6C show separation of sialylated and non-sialylated proteins by Sia-PS1 Lectenz® affinity chromatography (LAC). A purified Sia-PS1 sample (2 mg) was coupled chemically to a 1-mL sepharose column, followed by loading of an analyte. After competitive elution, the column was regenerated for the binding and elution of the next analyte. Experiments were performed on an AKTA Pure chromatography system. FIG. 7A shows the flow-through of non-sialylated glycoprotein horseradish peroxidase (HRP) and retention of fetuin in overlaid chromatograms. FIG. 7B shows an elution profile showing the separation of a mixture of BSA (non-glycosylated) and fetuin (sialylated glycoprotein). FIG. 7C shows an elution profile showing the separation of a mixture of asialofetuin (de-sialylated fetuin) and fetuin.

FIGS. 8A and 7B show LAC elution profiles for Sia-PS1 and synthetic neoglycoproteins. FIG. 8A shows a Sia-PS1 LAC elution profile of 3'-sialyllactose-BSA. FIG. 8A shows a Sia-PS1 LAC elution profile of 6'-sialyllactose-BSA. Each analyte (200 µg) was applied onto the LAC column in binding buffer, washed and competitively eluted under gravity flow. The LAC column used was the same as the one described in FIG. 7. Protein concentration of collected fractions was determined by spectrophotometric absorption at 280 nm. For comparison purpose (see FIG. 9), the neoglycoproteins were each loaded at 200 µg in 1 mL buffer volume to match the recommendation for a typical 1-mL lectin affinity columns. In each experiment, the amount of loaded analyte was nearly fully recovered by competitive elution.

FIG. 9A shows an elution profile for 3'-sialyllactose-BSA (200 µg) from a commercially available MAA column.

FIG. 10A shows a LAC profile showing the separation of the unbound proteins (flow-through peak; 319 µg) at the binding step and the bound proteins (elution peak; 30 µg). FIG. 10B shows SDS-PAGE of CFE (~125 µg loaded) and LAC elution fraction (~7 µg loaded). FIG. 10C shows MALDI profiles showing enrichment of small molecules in the LAC elution fraction. Note that the mass spectrometer used for the MALDI experiment is not sensitive enough to resolve molecules larger than 15 kD in size.

FIGS. 14A and 13B show BLI sensograms for the binding of Sia-3S1 (analyte) under different buffer conditions to oligosaccharides (immobilized ligands): 3'SL=α2,3-sialyllactose, 6'SL=α2,6-sialyllactose. FIG. 14A shows a BLI sensogram for the binding of Sia-3S1 (analyte) to oligosaccharides using a buffer composed of 10 mM EPPS, 10 mM NaCl, pH 7.5. FIG. 13B shows a BLI sensogram for the binding of Sia-3S1 (analyte) to oligosaccharides using a buffer composed of 10 mM EPPS, 25 mM NaCl, pH 7.5.

FIGS. 16A and 16B show Sia-3S1 LAC chromatography demonstrating selective binding to 3'SL-BSA over 6'SL-BSA. FIG. 16A shows results for 100 µg 3'SL-BSA loaded onto the Sia-3S1 LAC column. FIG. 16B shows results for 100 µg 6'SL-BSA loaded onto the Sia-3S1 LAC column. Sialylated BSA molecules bound onto the Sia-3S1 column were competitively eluted with 50 mM 3'SL or 6'SL solution before regeneration with 10 mM EPPS (pH 7.5) buffer containing 1 M NaCl ("NaCl regeneration"). Flow through amounts under each condition are approximately 5 µg.

DETAILED DESCRIPTION OF ILLUSTRATIVE EMBODIMENTS

Figure 2:
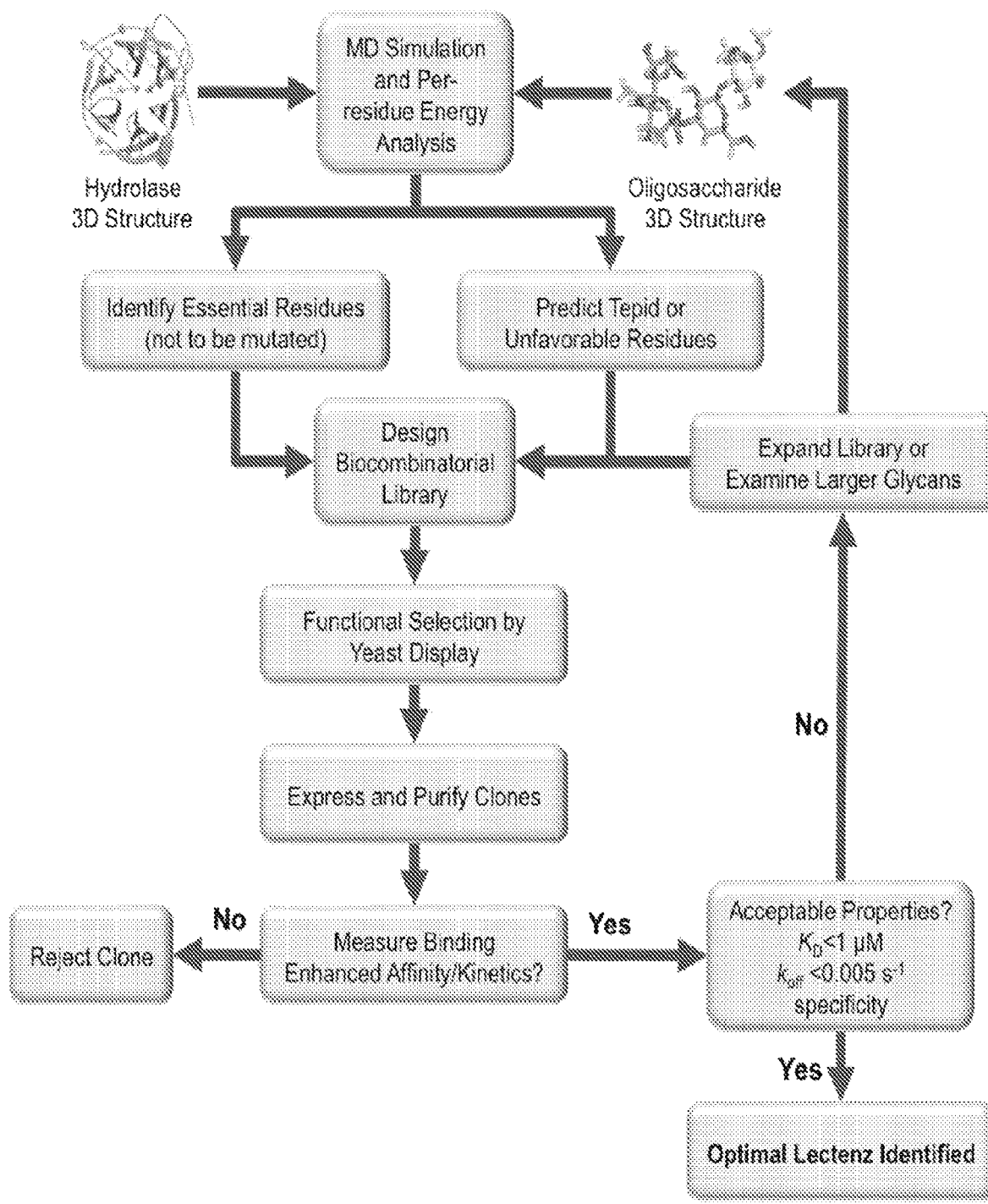
FIG. 2 shows a flowchart outlining the key steps in Lectenz® engineering.

The sialic acid-recognizing affinity reagent of the invention can be referred to as a Lectenz®, which term describes a novel class of engineered, lectin-like enzyme-derived reagents with specificity for glycan structures of biological significance. Lectenz® reagents are engineered from a parent enzyme, but have little or no enzymatic activity, and have lectin-like carbohydrate-binding properties. In some embodiments, Lectenz® reagents retain the specificity of the endogenous parent enzymes from which they are engineered. In other embodiments, the specificity of a Lectenz® reagent is tuned to a similar glycan structure or motif. Lectenz® reagents therefore have several advantages over either lectins or antibodies, including tunable specificity, tunable affinity, and ease of production.

The sialic acid-recognizing affinity reagents described herein offer numerous advantages over sialic acid-recognizing lectins, because they have been engineered to have high affinity, yet possess substrate specificity based on the carbohydrate processing enzyme, NanB. In some embodiments, substrate specificity the sialic acid-recognizing affinity reagent may be the same as NanB. In some embodiments, the substrate specificity the sialic acid-recognizing affinity reagent may be broader than NanB, i.e., it can be expanded or broadened, as in the pan-specific Sia-PS affinity reagents described herein. In some embodiments, the substrate specificity of the sialic acid-recognizing affinity reagent may be narrower than NanB (enhanced or increased specificity). In designing or assessing sialic acid-recognizing affinity-enhanced modified NanB molecules using structurally guided genetic manipulations as described herein and more generally in US Pat. Pub. 2012/0040474 ("Glycan-Specific Analytical Tools") and WO2015/161201 (U.S. Ser. No. 15/304,725), the binding affinity and specificity of the sialic acid are independently tunable depending on the needs of the researcher or clinician.

NanB Sialidase

Sialidases (neuraminidases) remove sialic acid, a 9-carbon carbohydrate, as the terminal sugar of various glycoconjugates. The present invention utilizes *S. pneumoniae* NanB sialidase as the template for development of novel sialic acid-recognizing affinity reagents. A three-dimensional representation of *S. pneumoniae* NanB is shown in FIG. 1. Panel B is rotated 90 degrees from the view of panel A. In these images, NanB is shown in complex with a substrate, 2,7-anhydro-Neu5Ac, shown as a sphere, bound to the NanB active site. Gut et al., FEBS Lett., 2008, 582(23-24):2248-3352.

The L-domain (lectin-like), also known as the CBM domain or CBM40 domain, constitutes the carbohydrate-binding module (CBM), which has been classified within the CBM40 family. The catalytic N-domain, also known as the glycosyl hydrolase (GH) domain, of the GH33 domain, which possesses neuraminidase activity, is also shown. A short linker (residues 225-230) connects the L-domain and the N-domain. An irregular domain, the I-domain, is also shown. With reference to SEQ ID NO:1, the approximate locations of the domains of NanB can be characterized as follows: a signal/leader sequence (residues 1-29), a CBM40 domain (residues 30-228), a catalytic domain (residues 229-345 and 459-697), and an irregular domain (residues 346-458). Active site include the classical sialidase arginine triad, Arg245, Arg557, and Arg619, as well as Tyr653, Glu541, and Asp270 (Gut et al., FEBS Lett., 2008, 582(23-24):2248-3352; Xu et al., J. Mol. Biol., 2008, 384: 436-449).

The NanB template can be SEQ ID NO:1, or a truncated version of SEQ ID NO:1. Typically, the signal sequence is not included in the template; thus, a useful NanB template is exemplified by amino acids 30-697 of SEQ ID NO:1.

The term "sialic acid" is often used to refer to a family of acidic sugars with a nine-carbon backbone. The most common sialic acid found in mammalian cells is N-acetyl-neuraminic acid (Neu5Ac, or NANA), which is acetylated at the C-5 position (Formula I).

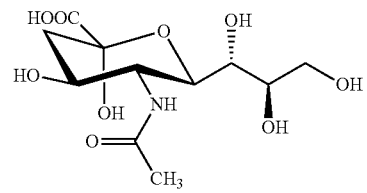

The numbering of the sialic acid structure begins at the carboxylate carbon and continues around the chain. The configuration that places the carboxylate in the axial position is the alpha-anomer (Formula II).

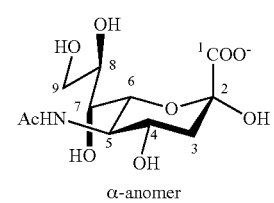

α-anomer

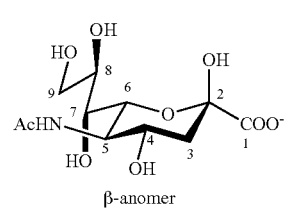

β-anomer

In the present invention, "sialic acid" generally refers to Neu5Ac as described in Examples I and II but can, in the appropriate context, include other derivatives of neuraminic acid as well, such as variants that are hydroxylated at the C-5 position (e.g., ketodeoxynonic acid, Kdn), or that have a hydroxylated 5-N-acetyl group (e.g., N-glycolylneuraminic acid, Neu5Gc) or that are not N-acylated (e.g., neuraminic acid, Neu). Varki et al., "Sialic Acids," Ch. 14 in Essentials of Glycobiology, 2$^{nd}$ Ed. (Cummings et al., Ed.), Cold Spring Harbor Press, Cold Spring Harbor, N.Y. (2009). Sialic acids can be present within a glycan at either a terminal position or an internal position. They can be found as a terminal saccharide component of biologically relevant N-glycans, O-glycans, and glycosphingolipids (gangliosides). They also are known to cap side chains of glycosylphosphatidylinositol (GPI) anchors. They may also be found as oligosialic acids or polysialic acids. Varki et al., "Sialic Acids," Ch. 14 in Essentials of Glycobiology, 2$^{nd}$ Ed. (Cummings et al., Ed.), Cold Spring Harbor Press, Cold Spring Harbor, N.Y. (2009). Sialic acids may be present as a component of oligosaccharide chains of mucins, glycoproteins, glycopeptides, and glycolipids, including glycosphingolipids and glycolipopeptides. Typically, sialic acid is linked to another monosaccharide in an α-linkage.

Sialic Acid Recognition

The sialic acid-recognizing affinity reagent of the invention recognizes (i.e., binds to) a sialic acid component an oligosaccharide. A sialic acid can be covalently bound to an adjacent monomer of the oligosaccharide in any of several linkage topographies. While two linkage conformations (α and β) are possible, typically the linkage to the adjacent saccharide is in the α conformation. Linkage can occur at any of a number of positions on the adjacent monomer, such as the 3 position, 6 position, or 8 position of the adjacent monomer, resulting in an α2,3 linkage, an α2,6 linkage or an α2,8 linkage, respectively. The oligosaccharide containing the sialic acid can be a disaccharide (2 monomers) or a higher oligosaccharide (more than 2 monomers). Advantageously, the oligosaccharide can be a part of (i.e., a component of) a glycan structure that is present in a glycosylated biomolecule, such as a glycoprotein, glycopeptide, or glycolipid.

Figure 3A:
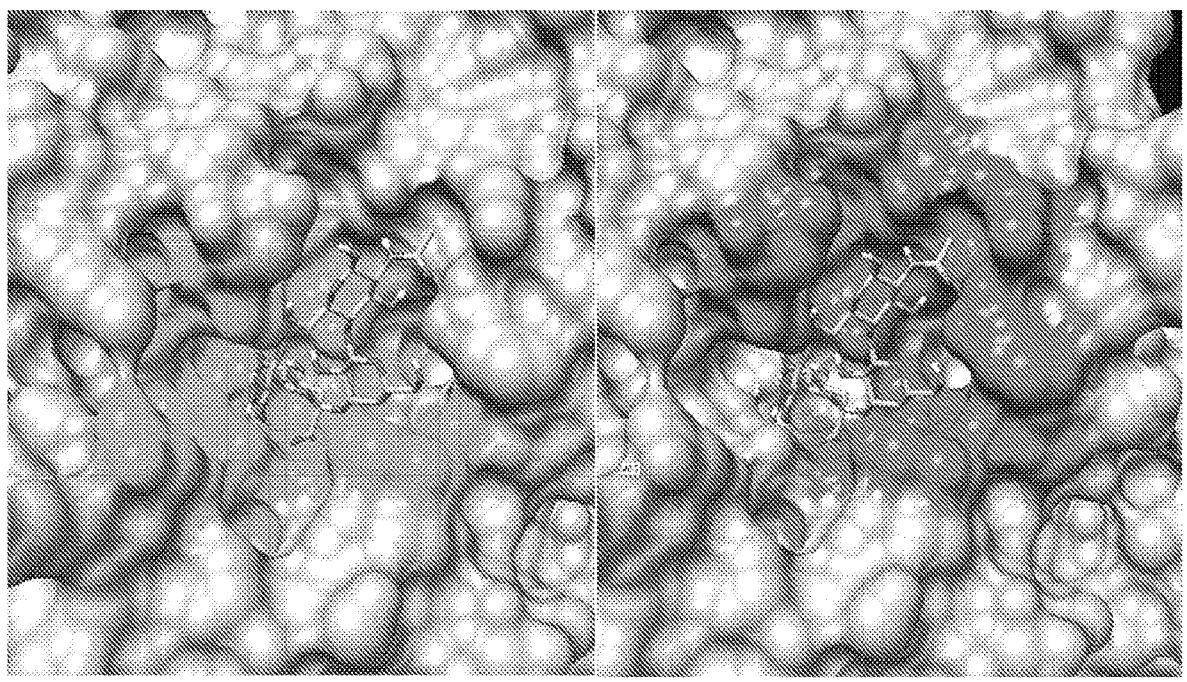
FIG. 3A shows a model of 3'sialyllactosamine (3'SLN, stick) bound to enzyme with residues proximal (≤4.5 Å) to sialic acid shown in left panel as shaded residues and those proximal to the Gal/GlcNAc residues of 3'SLN shown in right panel as shaded residues.

The sialic-acid recognizing affinity reagents of the invention are based on, i.e., engineered from, the amino acid sequence of NanB, as exemplified by NanB from S. pneumoniae and shown in SEQ ID NO:1 (the full wild-type amino acid sequence, including the leader peptide; FIG. 3C) and SEQ ID NO:4 (the amino acid sequence without the leader peptide; FIG. 3D). Exemplary mutation sites are listed in Table 1, and can include one or more sites designated as important for binding (e.g., R619, W674, R245, R676, Y653, S675, R264, H269, I246, I326, R557, and D327) and/or one or more sites designated as "tepid" or as making weak contributions to binding (e.g., E541, E669, S673, T539, L679, T268, P492, D270, Y671, A538, N353, N316, P660 and N683).

It should be understood that affinity reagents engineered from NanB, such as Sia-PS1, Sia-PS2, Sia-PS3, Sia-PS4, Sia-PS5, Sia-3S1, Sia-3S2, Sia-3S3, Sia-3S5, Sia-3S6, Sia-3S7, Sia-3 S7*, Sia-3S8, Sia-3S9, which are engineered SEQ ID NO:4 and described in Examples I and II can, in some embodiments, include further modifications. For example, they can include truncations at or additions to the ends of SEQ ID NO:4, for example truncations or additions of 1, 2, 3, 4, 5, 6, 7, 8, 9, or 10 amino acids, and/or conservative mutations in regions not involved in activity or substrate binding, as long as the overall domain structure of the affinity reagent remains intact, and pan-specific binding to sialic acid (in the case of Sia-PS reagents) or specific binding to Siaα2,3 linkages (in the case of Sia-3S reagents) is preserved. Additionally, some embodiments of the sialic acid-recognizing affinity reagent may contain the carbohydrate binding module (CBM) domain of NanB (e.g., residues from 30 through about 229 of SEQ ID NO:1), but not the glycosyl hydrolase (GH) domain; other embodiments of the sialic acid-recognizing affinity reagent may contain the glycosyl hydrolase (GH) domain (e.g., residues from about 229 through 697 of SEQ ID NO:1), but not the carbohydrate binding module (CBM) domain of NanB.

Pan-Specific Sialic Acid-Recognizing Affinity Reagent

In one embodiment, the sialic acid-recognizing affinity reagent is pan-specific in its recognition of (i.e., binding to) a sialic acid. This pan-specific affinity reagent recognizes a sialic acid (Neu5Ac) independent of the linkage configuration between the Neu5Ac and the adjacent saccharide. The linkage configurations recognized by the pan-specific affinity reagent include Siaα2,3-, α2,6-, and α2,8-linkages. Optionally and advantageously, as in the case of Sia-PS1, the pan-specific sialic acid-recognizing affinity reagent also recognizes common modifications of Neu5Ac, such as 9-O acetylation, and variants of the N-glycolyl form of sialic acid.

The pan-specific sialic acid-recognizing affinity reagent of the invention is exemplified by a NanB fragment (residues 30-697; SEQ ID NO:4) with a single mutation. Exemplary mutation sites include Y653, D270, and E541. Exemplary pan-specific affinity reagents, each having a single mutation in the NanB GH domain as noted, are shown in Table 2 and include Sia-PS1 (Y653F), Sia-PS2 (D270A), Sia-PS3 (D270N), Sia-PS4 (E541A), and Sia-PS5 (E541Q).

Surprisingly, these single site mutations have a dual effect. They reduce (Sia-PS2 and Sia-PS3) or effectively eliminate (Sia-PS1, Sia-PS4, and Sia-PS5) catalytic activity, and they broaden specificity for sialic acid ligand binding. The pan-specific sialic acid-recognizing affinity reagent we chose for further validation study was Sia-PS1 that contains the Y653F at active site residue Tyr653. This one mutation, which involves removal of a single hydroxyl group, not only eliminates enzyme activity, but astonishingly introduces pan-specific binding into the mutated, inactivated enzyme, despite its distance from the carbohydrate binding module (CBM) domain of the NanB.

Linkage-Specific Sialic Acid-Recognizing Affinity Reagent

In another embodiment, the sialic acid-recognizing affinity reagent is specific for a single sialic acid linkage configuration, namely, an α2,3-linked sialic acid. These affinity reagents recognize (i.e., bind to) a sialic acid linked to the adjacent saccharide in an α2,3-linkage, but not a sialic acid linked to the adjacent saccharide in an α2,6-linkage or an α2,8-linkage.

The linkage-specific sialic acid-recognizing affinity reagent of the invention is exemplified by a NanB fragment (residues 30-697; SEQ ID NO:4) with multiple mutations. Together, the mutations reduce or eliminate catalytic activity, and alter the binding specificity of the inactivated enzyme to make it specific for α2,3-linked sialic acid (versus α2,6-linked sialic acid and α2,8-linked sialic acid). Exemplary mutation sites include R193, D270, A538, E541, P660, S673, D327, and N683. Exemplary sialic acid-recognizing affinity reagents with heightened specificity for an α2,3-linked sialic acid are shown in Table 4, include the following, with mutations sites identified:

| | |
|---|---|
| Sia-3S1 | R193A, D270Q, A538V, E541D |
| Sia-3S2 | R193A, D270G, A538W, E541D, P660Q, S673A |
| Sia-3S3 | R193A, D270G, A538V, E541D, S673A |
| Sia-3S5 | R193A, D327E, A538F, E541A |
| Sia-3S6 | R193A, D270G, A538H, E541A, N683S |
| Sia-3S7 | R193A, D270H, D427Y, A538M, E541A, L690F |
| Sia-3S7* | R193A, D270H, A538M, E541A |
| Sia-3S8 | R193A, D270I, D327V, A538F, E541I, S673Q |
| Sia-3S9 | R193A, D270G, A538I, E541S, S673A |

Sia-3S7* is based on Sia-3S7, but without mutations D427Y and L690F. These two missing mutations are not expected to affect binding specificity.

Conjugates

The invention also includes conjugates of the sialic acid-recognizing affinity reagent. A conjugate includes, as a first component, a sialic acid-recognizing affinity reagent, which is covalently linked to at least one second component, which may be a proteinaceous component or a nonproteinaceous component. In some embodiments, a conjugate that includes a proteinaceous component can be synthesized as a fusion protein using well-known recombinant DNA methods. In some embodiments, the conjugate includes a proteinaceous or non-proteinaceous component that is chemically or enzymatically conjugated to the sialic acid-recognizing affinity reagent.

One example of a conjugate of the invention includes a sialic acid-recognizing affinity reagent conjugated to a therapeutic agent, also referred to herein as a drug. This conjugate is analogous to the well-known antibody-drug conjugate (ADC) except that the sialic acid-recognizing affinity reagent is used in place of the antibody. Drugs that can be conjugated to a sialic acid-recognizing affinity reagent include, without limitation, cytotoxins, anti-metabolites, alkylating agents, antibiotics and anti-mitotic agents.

Anti-cancer, anti-inflammatory, pro-inflammatory, and immune-moderating drugs are particularly suitable for conjugation to a sialic acid-recognizing affinity reagent, since cancerous and precancerous conditions, as well as inflammation and immune conditions, are often associated with changes in protein glycosylation patterns. For example, a therapeutic or diagnostic radioactive agent can be coupled to or incorporated into a sialic acid-recognizing affinity reagent to yield a "Lectenz®-drug" conjugate that can be targeted to a cancer glycomarker. In one embodiment, the therapeutic or diagnostic agent can be targeted to mucus linings or membranes, such as in the lungs or gut.

Likewise, anti-viral and anti-bacterial drugs are also particularly suitable for incorporation into a "Lectenz®-drug" conjugate, as targeting viral or bacterial glycosylated biomolecules has great therapeutic potential.

Another example of a conjugate of the invention includes a sialic acid-recognizing affinity reagent conjugated to a diagnostic or detection agent. The diagnostic or detection agent can include a detectable label, including but not limited to a radioactive, fluorescent, phosphorescent, colorimetric, enzymatic, immunological, magnetic, paramagnetic, diamagnetic or electromagnetic label. It should be understood that a sialic acid-recognizing affinity reagent need not be conjugated to function as a diagnostic or detection agent, as the sialic acid-recognizing affinity reagent can be detected directly, e.g., via immunoassay.

Another example of a conjugate of the invention includes a sialic acid-recognizing affinity reagent conjugated to a marker sequence, for example a peptide such as hexahistidine or hemagglutinin, to facilitate purification. Included in the invention are, for example, fusion proteins that include a sialic acid-recognizing affinity reagent covalently linked to glutathione S-transferase (GST), thioredoxin, bovine serum albumin, bovine pancreatic trypsin inhibitor, or fluorescent proteins such as green fluorescent protein (GFP).

Methods of Use

The vast number of potential applications for a sialic acid-recognizing affinity reagent, because of its lectin-like properties, will be immediately apparent to persons skilled in the art. The sialic acid-recognizing affinity reagents of the invention have many uses as diagnostic, therapeutic, bioengineering or research reagents in clinical or research settings. For example, changes in the normal levels of glycan structures such as terminal sialic acid may be markers of disease states. New highly specific reagents are thus desirable in order to overcome current limitations in the discovery and exploitation of disease-related glycans. The sialic acid-recognizing affinity reagent can be used to identify new, or detect previously identified, disease-associated sialic acid modifications of glycopeptides, glycoproteins and glycolipids. For example, the sialic-acid recognizing affinity reagent is useful for the detection of sialic acid and analysis of markers relevant to prostate-specific antigen (PSA) and influenza virus.

As another example, the sialic acid-recognizing affinity reagent can be employed as a research or diagnostic tool in an affinity matrix for sample enrichment and can, in conjunction with existing mass spectrometric based methods, provide linkage information, as further described below.

The sialic acid-recognizing affinity reagent can be utilized in any method can otherwise be performed with an anti-glycan antibody or a lectin. Thus, sialic acid-recognizing affinity reagents of the invention can be advantageously substituted for anti-glycan antibodies in numerous medical and laboratory methods, including diagnostic, analytical and therapeutic methods. Likewise, the sialic acid-recognizing affinity reagents of the invention can be advantageously substituted for lectins in numerous diagnostic and analytical laboratory methods. For example, a sialic acid-recognizing affinity reagent can be employed as a capture reagent, as in affinity chromatography enrichment, or in histological studies, Western blots, FACS-based detection, and the like. As a capture reagent or recognition element, it is useful in a variety of applications for the discovery of glycan-based disease markers, as in glycoprofiling analysis (see, e.g., U.S. Pat Publ. 2014/0005069, published Jan. 2, 2014). For example, sialic acid-recognizing reagent of the invention can be a component of a multicomponent microarray that contains other Lectenz® reagents and/or lectins, antibodies, or other carbohydrate-binding molecules, with varying specificities.

Therapeutic uses are also envisioned and are described in more detail below. For example, the sialic acid-recognizing affinity reagents can be used for detection of sialic acid relevant for quality control in the manufacturing of biologics. More specifically, they can be used to detect the presence, absence, or linkage position of sialic acid on synthetic or recombinantly produced glycoprotein-based or glycolipid-based biologics, such as therapeutic antibodies, as step in quality control during synthesis or storage.

Diagnostic and Analytical Methods

A sialic acid-recognizing affinity reagent or conjugate thereof can be used to detect sialic acid-containing glycans in a biological or synthetic sample. For example, a biological sample, such as a tissue or fluid, can be contacted with the sialic acid-recognizing affinity reagent or conjugate thereof, alone or in conjunction with other analytical reagents, to detect and/or characterize the level or type of glycosylation and/or glycation in the biological sample. Characterization can include of the glycan can include identifying a constituent saccharide of the glycan, determining saccharide composition of the glycan, determining linkage positions within the glycan, or determining stereochemistry of the glycan. As another example, a sialic acid-recognizing affinity reagent or conjugate thereof can be used for quality control in the synthesis of therapeutic biologics, for example in the synthesis of therapeutic antibodies, to monitor the level or type of glycosylation. See PCT patent publication WO2012/118928, published Sep. 7, 2012, and US Pat. Publ. 2014/0005069, published Jan. 2, 2014. A sialic acid-recognizing affinity reagent or conjugate thereof can be utilized as an affinity reagent or as part of an affinity matrix; for example, it can be tethered to a solid support, such as a surface, column, resin, bead, particle or nanoparticle, and used in methods to detect or enrich for sialic acid-containing compounds in or from biological or synthetic samples. Tethered sialic acid-recognizing affinity reagents can also be used to isolate and/or purify synthetic glycosylated compounds.

Diagnostics can be performed on a biological sample obtained from a subject, but can also be performed in vivo. In in vivo applications, a sialic acid-recognizing affinity reagent or conjugate thereof is administered to a subject, and binding of the sialic acid-recognizing affinity reagent within the subject is detected. Preferably, a conjugate is administered to the subject, wherein the conjugate includes a detectable label so as to facilitate biomedical imaging. Examples of a suitable conjugate include a sialic acid-recognizing affinity reagent conjugated to a radiolabel, a paramagnetic label, or a diamagnetic label.

The sialic acid-recognizing affinity reagent can be used to interrogate biological samples in the search for abnormal glycosylation. Examples of biological samples include, but are not limited to, any biological fluid, tissue, or organ. Examples of the biological fluids include, but are not limited to blood, urine, serum, saliva, cerebra-spinal fluid, and semen. In other embodiments, a sialic acid-recognizing affinity reagent can be used for a detection of the presence or amount of a target analyte in biological fluids and tissues. Examples of targets are exogenously consumed species, such as plant polysaccharides, carbohydrate-based drugs, and pathogens, whose surfaces are often coated in complex distinct glycans. The sialic acid-recognizing affinity reagent also has application in drug discovery and evaluation of biological activity of new glycan-based compounds.

The sialic acid-recognizing affinity reagent can be used for diagnosing, and/or treating diseases manifested by abnormal glycosylation. It can be used to detect certain tumor antigens comprising glycoproteins, glycolipids, and/or a variety of carbohydrate epitopes. A number of these tumor antigens have been found to be up-regulated in the neoplastic disease state. Examples of tumor antigens that can signal a development and progression of a neoplastic disorder include, but are not limited to, carcinoembryonic antigen (CEA), which is a glycoprotein associated with colorectal, gastric, pancreatic, lung, and breast carcinomas, and the developing fetus; carbohydrate antigen 19-9 (CA 19-9), or sialylated Lewis A antigen, which is present in a glycolipid found in patients with pancreatic cancer; and carbohydrate antigen 15-3 (CA15-3), associated with breast cancer.

The presence of the antigen does not necessarily indicate transformation to a cancerous cell; however, its localization in the cell is indicative, as in the case of CEA. For this reason, there is a need for highly selective and high affinity analytical tools. The diagnostic tests currently rely on antibodies that were often generated against the peptide portions of the glycoprotein or sugar portions of glycolipid, however, the exact epitopes are only now being defined. In the examples in which the glycans have been characterized, multiple glycoforms are often present (CEA, for example). Lacking reagents that are able to discriminate between glycoforms, it is currently impossible to determine the extent to which subtle variations in glycosylation correlate with disease state, cancer type, or tissue localization. At present, these questions can be addressed primarily by MS analyses of isolated glycoproteins, which are examined as mixtures of glycoforms. Typically, the only level of glycoform-focusing that is performed is the enrichment in high-mannose containing glycans using lectin (concanavalin A, (Con A)) affinity chromatography. More efficient laboratory analyses and routine clinical diagnostic techniques remain severely limited by the lack of glycoform-specific reagents.

The sialic acid-recognizing affinity reagent may have utility for quantifying the relative abundances of various glycoforms present for any given glycoprotein in a biological sample. As used herein, the term "glycoform" refers to a protein with a specific glycan attached. A glycoprotein can have multiple glycoforms. More specifically, a glycoform is an isoform of a protein that differs only with respect to the number or type of attached glycan; the amino acid sequence is the same for the various glycoforms. Glycoproteins often comprise a number of different glycoforms, with alterations in the attached saccharide or oligosaccharide. Advantageously, a sialic acid-recognizing affinity reagent can be used to enrich the biological sample for sialic acid-containing glycans. It can likewise be used to identify specific glycosylation sites on the protein surface to which the glycans are attached. It can also be used to separate intact glycopeptides from a proteolytic digest of a glycoprotein. Enriching the sample in the analyte of interest is of great assistance in the further characterization of the glycopeptides fractions. In particular, enrichment facilitates the identification of the peptide sequence and the glycan structure, which can enable the identification within the intact protein of the glycosylation sites and the characterization of the particular glycans present at each glycosylation site.

The sialic acid-recognizing affinity reagent can be used in monitoring specific glycan modifications of proteins in biological fluids, tissues, organs, or living cells. Recognition is not expected to depend on the identity of the protein, and the sialic acid-recognizing affinity reagent is expected to be able to recognize any protein sequence that includes a sialic acid (consistent with the particular specificity of the sialic acid-recognizing affinity reagent, i.e., whether it is pan-specific or specific for a particular linkage), and therefore will be very useful for detection of particular glycan modifications.

In yet other embodiments, the sialic acid-recognizing affinity reagent can be used for in vitro or in vivo staining cells or tissues.

The sialic acid-recognizing affinity reagent can be employed to monitor sialylation of glycans in a mixture, as might arise during the production of recombinant glycoproteins for use in the pharmaceutical or research industries.

In the foregoing embodiments, the sialic acid-recognizing affinity reagent can be tagged with a stain or a dye and applied to a biological sample comprising cells or tissues or glycoproteins or glycopeptides or oligosaccharides or polysaccharides of interest.

Another aspect of the present invention provides methods of using sialic acid-recognizing affinity reagent for analytical applications. The sialic acid-recognizing affinity reagent of the present invention can be used as sialic acid-specific analytical tool. Glycan-specific analytical tools have potential use as a method of detection in many areas, including environmental, fermentation, food and medical areas and could be used for in vivo or in vitro sensing in humans or animals. For example, the sialic acid-recognizing affinity reagent of the present invention can be used as an affinity reagent or as vehicle for tissue staining. As another example, the sialic acid-recognizing affinity reagent can be used for enriching a biological sample for sialic acid-containing glycans. In yet other examples, the sialic acid-recognizing affinity reagent can be used to determine specific glycosylation sites on glycoproteins.

In certain embodiments, the sialic acid-recognizing affinity reagent can be used as a reagent for affinity separation, including, for example, affinity chromatography. Affinity chromatography is a method of separating biochemical mixtures, based on a highly specific biological interaction such as that between the binding protein and the glycan. The present invention is not limited to any specific design or chromatographic system. In general, the sialic acid-recognizing affinity reagent will be either covalently attached or otherwise immobilized to the solid support, and will constitute a stationary phase. In certain embodiments, the stationary phase that is derivatized with the sialic acid-recognizing affinity reagent can be used in column chromatography. In these embodiments, the particles of the solid stationary phase will be used to fill the whole inside volume of the tube (packed column). Alternatively, the solid phase particles will be concentrated on or along the inside tube wall leaving an open, unrestricted path for a biological sample (i.e., the mobile phase) in the middle part of the tube (open tubular column). In other embodiments, the derivatized stationary phase can be used for batch chromatography. In these embodiments, the stationary phase can be added to a vessel and mixed with the biological sample. Although the foregoing example generally focused on affinity chromatography, it is understood that these principals are readily applied to other affinity purification protocols.

Therapeutic Methods

In certain embodiments, the sialic acid-recognizing affinity reagent of the invention can be used as a therapeutic agent or modified for delivery of an active therapeutic agent. Since the sialic acid-recognizing affinity reagent of the present invention has a defined glycan specificity, a delivery of the therapeutic agents can be targeted only to those cells, tissues, or organs that display a biomolecule, such as a glycoprotein or glycolipid with the glycan structure recognized by the sialic-acid recognizing affinity reagent.

The potential therefore exists for the sialic acid-recognizing affinity reagent to be used as a therapeutic in many applications such as targeted drug delivery. Changes in the levels and locations of sialic acid-containing glycans have been shown to be associated with many diseases, including cancer. The sialic acid-recognizing affinity reagent is thus expected to have direct applications in the field of cancer research, potentially leading to the development of a product for the detection of certain forms of cancer. It is also expected to have utility as a reagent for use in glycomics, wherein it may be used to enrich samples containing sialic acid-containing glycans, thereby enabling detection and analysis of these important carbohydrates. A sialic acid-recognizing affinity reagent can be used as a vehicle for targeted delivery of therapeutic agents.

A sialic acid-recognizing affinity reagent, or conjugate thereof, can be administered to a subject to treat or prevent an infection, disease, or disorder. The infection can be, for example, viral, bacterial, parasitic, or fungal. The disease or disorder can result from an exogenous agent, or it can be autologous or autoimmune.

In one embodiment, a sialic acid-recognizing affinity reagent is administered to a subject so as to bind to a sialic acid-containing glycan present within the subject, so as to achieve a therapeutic or prophylactic effect. The sialic acid-containing glycan can be an endogenous biomolecule produced by the subject, or it can be an exogenous biomolecule produced by a pathogen. In one embodiment, the sialic acid-recognizing affinity reagent binds to an endogenous biomolecule, for example a biomolecule associated with cancer, a precancerous condition, or an immune disorder of the subject. In another embodiment, the sialic acid-recognizing affinity reagent prevents binding of a pathogen to a host cell; in another embodiment, the sialic acid-recognizing affinity reagent prevents internalization of a pathogen into a host cell.

In another embodiment, a conjugate of a sialic acid-recognizing affinity reagent is administered to a subject, wherein the conjugate includes a therapeutic agent as exemplified above. The therapeutic agent can be an antibiotic agent, for example an agent that targets a microbial pathogen. The therapeutic agent can be an agent that targets an autologous or autoimmune disease, for example an anti-cancer agent, such as a cytotoxin, or an immunoactive agent. Examples of therapeutic agents that can be used for site-specific delivery include, but are not limited to, various chemotherapeutic, antibiotic, and antiviral agents, toxins, radioisotopes, cytokines, etc.

A sialic acid-recognizing affinity reagent or conjugate thereof for therapeutic use can be tested for toxicity in suitable animal model systems, for example in rats, mice, monkeys, or rabbits. The usefulness of a sialic acid-recognizing affinity reagent or conjugate thereof to treat or prevent a viral infection can be assessed by evaluating its ability to inhibit viral replication, inhibit viral transmission or to treat or prevent symptoms associated with viral infection. Likewise the usefulness of a sialic acid-recognizing affinity reagent or conjugate thereof to treat or prevent a bacterial infection can be assessed by evaluating its ability to inhibit the bacterial replication, or to treat or prevent symptoms associated with bacterial infection. Usefulness in treating cancer can be evaluated by assessing the ability of a sialic acid-recognizing affinity reagent or conjugate thereof to inhibit the growth or metastasis of cancerous cells, to inhibit angiogenesis, or to cause cell death.

Method of Making

The sialic acid-recognizing affinity reagent of the invention may be expressed in a host cell using genetic engineering techniques. The term "cell" is meant to include any type of biological cell. The host cell can be a eukaryotic cell or a prokaryotic cell. Preferably, the host cell is a prokaryotic cell such as a bacterial cell; however single cell eukaryotes such as protists or yeasts are also useful as host cells. Preferred host cells are microbial cells, preferably the cells of single-celled microbes such as bacterial cells or yeast cells. Notwithstanding the above preferences for bacterial and/or microbial cells, it should be understood that the sialic acid-recognizing affinity reagent can be expressed without limitation in the cell of an animal, plant, insect, yeast, protozoan, bacterium, or archaebacterium. Examples of microbial cells that can be engineered to express the sialic acid-recognizing affinity reagent of the invention, in addition to *E. coli*, include a wide variety of bacteria and yeast including members of the genera *Escherichia, Salmonella, Clostridium, Zymomonas, Pseudomonas, Bacillus, Rhodococcus, Alcaligenes, Klebsiella, Paenibacillus, Lactobacillus, Enterococcus, Arthrobacter, Brevibacterium, Corynebacterium Candida, Hansenula, Pichia* and *Saccharomyces*. Preferred microbial cells include, without limitation, *Escherichia coli, Bacillus subtilis, Bacillus licheniformis, Alcaligenes eutrophus, Rhodococcus erythropolis, Paenibacillus macerans, Pseudomonas putida, Enterococcus faecium, Saccharomyces cerevisiae, Lactobacillus plantarum, Enterococcus gallinarium* and *Enterococcus faecalis*.

A cell that has been genetically engineered to express the sialic acid-recognizing affinity reagent of the invention may be referred to as a "host" cell, a "recombinant" cell, a "genetically engineered" cell or simply an "engineered" cell. These and similar terms are used interchangeably. A genetically engineered cell contains one or more artificial sequences of nucleotides which have been created through standard molecular cloning techniques to bring together genetic material that is not natively found together. DNA sequences used in the construction of recombinant DNA molecules can originate from any species. For example, plant DNA may be joined to bacterial DNA, or human DNA may be joined with fungal DNA. Alternatively, DNA sequences that do not occur anywhere in nature may be created by chemical synthesis of DNA or by directed mutation of DNA, and incorporated into recombinant molecules. Proteins that result from the expression of recombinant DNA are often termed recombinant proteins. Examples of recombination are described in more detail below and may include inserting foreign polynucleotides (obtained from another species of cell) into a cell, inserting synthetic polynucleotides into a cell, or relocating or rearranging polynucleotides within a cell. Any form of recombination may be considered to be genetic engineering and therefore any recombinant cell may also be considered to be a genetically engineered cell.

As will be appreciated by a person of skill in the art, expression of a protein, such as the sialic acid-recognizing affinity reagent of the invention, can be achieved through a number of molecular biology techniques. For example, expression can be achieved by introducing into the host cell one or more copies of a polynucleotide encoding the desired protein. The polynucleotide encoding the desired protein may be endogenous or heterologous to the host cell. Preferably, the polynucleotide is introduced into the cell using a vector; however, naked DNA may also be used. The polynucleotide may be circular or linear, single-stranded or double stranded, and can be DNA, RNA, or any modification or combination thereof. The vector can be any molecule that may be used as a vehicle to transfer genetic material into a cell. Examples of vectors include plasmids, viral vectors, cosmids, and artificial chromosomes, without limitation. Examples of molecular biology techniques used to transfer nucleotide sequences into a microorganism include, without limitation, transfection, electroporation, transduction, and transformation. These methods are well known in the art. Insertion of a vector into a target cell is usually called transformation for bacterial cells and transfection for eukaryotic cells, however insertion of a viral vector is often called transduction. The terms transformation, transfection, and transduction, for the purpose of the instant invention, are used interchangeably herein. A polynucleotide which has been transferred into a cell via the use of a vector is often referred to as a transgene.

Preferably, the vector is an expression vector. An "expression vector" or "expression construct" is any vector that is used to introduce a specific polynucleotide into a target cell such that once the expression vector is inside the cell, the protein that is encoded by the polynucleotide is produced by the cellular transcription and translation machinery. Typically an expression vector includes regulatory sequences operably linked to the polynucleotide encoding the desired protein. Regulatory sequences are common knowledge to the person of the skill in the art and may include for example, an origin of replication, a promoter sequence, and/or an enhancer sequence. The polynucleotide encoding the desired protein can exist extrachromosomally or can be integrated into the host cell chromosomal DNA.

Extrachromosomal DNA may be contained in cytoplasmic organelles, such as mitochondria (in most eukaryotes), and in chloroplasts and plastids (in plants). More typically, extrachromosomal DNA is maintained within the vector on which it was introduced into the host cell. In many instances, it may be beneficial to select a high copy number vector in order to maximize the expression of the protein. Optionally, the vector may further contain a selectable marker. Certain selectable markers may be used to confirm that the vector is present within the target cell. Other selectable markers may be used to further confirm that the vector and/or transgene has integrated into the host cell chromosomal DNA. The use of selectable markers is common in the art and the skilled person would understand and appreciate the many uses of selectable markers. Optionally, the vector may further contain a reporter gene. Reporter genes may be used to confirm that the vector is expressing within the target cell, and may be further used to monitor the expression from the vector. The use of reporter genes is common in the art and the skilled person would understand and appreciate the many uses of reporter genes.

A sialic acid-recognizing affinity reagent of the invention can be isolated and optionally purified from any genetically engineered cell described herein. It can be isolated directly from the cells, or from the culture medium, for example, during an aerobic or anaerobic fermentation process. Isolation and/or purification can be accomplished using known methods.

Also provided by the invention is a kit that includes a sialic acid-recognizing affinity reagent, conjugate, fusion protein or affinity matrix of any of the preceding claims, and instructions for use.

EXEMPLARY EMBODIMENTS

Embodiment 1. A sialic acid-recognizing affinity reagent comprising a catalytically inactive NanB neuraminidase protein, or fragment thereof, having at least one amino acid mutation compared to a corresponding wild-type NanB neuraminidase protein, wherein the mutation
  (a) reduces or eliminates the neuraminidase activity of the NanB protein; and
  (b) affects sialic acid binding affinity or binding specificity;
and wherein said affinity reagent binds to a sialic acid component of a glycan.

Embodiment 2. The sialic acid-recognizing affinity reagent of embodiment 1, wherein the NanB fragment comprises at least one of the carbohydrate binding module (CBM) domain of the NanB protein and the glycosyl hydrolase (GH) domain of the NanB protein.

Embodiment 3. The sialic acid-recognizing affinity reagent of embodiment 1 or 2, wherein the affinity reagent is pan-specific for sialic acid.

Embodiment 4. The sialic acid-recognizing affinity reagent of embodiment 3, wherein the affinity reagent binds to Neu5Ac linked to an adjacent saccharide monomer in an $\alpha 2,3$ linkage, Neu5Ac linked to an adjacent saccharide monomer in an $\alpha 2,6$ linkage, and Neu5Ac linked to an adjacent saccharide monomer in an $\alpha 2,8$ linkage.

Embodiment 5. The sialic acid-recognizing affinity reagent of embodiment 3 or 4 which binds to at least one variant of Neu5Ac.

Embodiment 6. The sialic acid-recognizing affinity reagent of any of embodiments 3-5, wherein the mutation is at a site selected from the group consisting of Y653, D270, and E541, as represented in SEQ ID NO:1 or SEQ ID NO:4.

Embodiment 7. The sialic acid-recognizing affinity reagent of embodiment 6, wherein the mutation is in S. pneumoniae NanB (SEQ ID NO:1 or SEQ ID NO:4) or fragment thereof, or a corresponding position in a homologous NanB sequence.

Embodiment 8. The sialic acid-recognizing affinity reagent of embodiment 6 or 7, wherein the mutation is selected from the group consisting of Y653F, D270A, D270N, E541A, and E541Q.

Embodiment 9. The sialic acid-recognizing affinity reagent of embodiment 8, wherein the mutation is Y653F.

Embodiment 10. The sialic acid-recognizing affinity reagent of embodiment 8 selected from the group consisting of Sia-PS1, Sia-PS2, Sia-PS3, Sia-PS4, and Sia-PS5.

Embodiment 11. The sialic acid-recognizing affinity reagent of embodiment 10 which is Sia-PS1.

Embodiment 12. The sialic acid-recognizing affinity reagent of embodiment 1 or 2, wherein the affinity reagent has a plurality of amino acid mutations compared to a corresponding wild-type NanB neuraminidase protein.

Embodiment 13. The sialic acid-recognizing affinity reagent of embodiment 12, wherein said plurality of mutations comprises:
    (a) at least one first mutation that reduces or eliminates the catalytic activity of the NanB protein; and
    (b) at least one second mutation that affects binding affinity or binding specificity.

Embodiment 14. The sialic acid-recognizing affinity reagent of embodiment 12 or 13, wherein the affinity reagent is specific for Neu5Ac that is linked to an adjacent saccharide monomer in an α2,3 linkage.

Embodiment 15. The sialic acid-recognizing affinity reagent of any of embodiments 12-14, wherein the plurality of mutations are at sites selected from the group consisting of R193, D270, A538, E541, P660, 5673, D327, and N683, as represented in SEQ ID NO:1 or SEQ ID NO:4.

Embodiment 16. The sialic acid-recognizing affinity reagent of embodiment 15, wherein the plurality of mutations are in S. pneumoniae NanB (SEQ ID NO:1 or SEQ ID NO:4) or fragment thereof, or a corresponding position in a homologous NanB sequence.

Embodiment 17. The sialic acid-recognizing affinity reagent of embodiment 15 or 16, wherein the plurality of mutations are selected from the group consisting of R193A, D270Q, D270G, D270H, D270I, A538V, A538W, A538F, A538H, A538M, A538I, E541D, E541A, E541I, E541S, P660Q, S673A, S673Q, D327E, D327V, and N683S.

Embodiment 18. The sialic acid-recognizing affinity reagent of embodiment 17, wherein the plurality of mutations comprise R193A, D270Q, A538V, and E541D.

Embodiment 19. The sialic acid-recognizing affinity reagent of embodiment 17 selected from the group consisting of Sia-3S1, Sia-3S2, Sia-3S3, Sia-3S5, Sia-3S6, Sia-3S7, Sia-3 S7*, Sia-3S8, and Sia-3 S9.

Embodiment 20. The sialic acid-recognizing affinity reagent of embodiment 19 which is Sia-PS1.

Embodiment 21. The sialic acid-recognizing affinity reagent of any of the preceding embodiments, wherein the glycan is a constituent of a glycosylated biomolecule.

Embodiment 22. The sialic acid-recognizing affinity reagent of embodiment 21, wherein the glycosylated biomolecule comprises a glycoprotein, a glycopeptide, a glycolipid, a glycolipoprotein, or a glycolipopeptide.

Embodiment 23. A conjugate comprising a first component comprising a sialic acid-recognizing affinity reagent of any of the preceding embodiments, covalently linked to a second component.

Embodiment 24. The conjugate of embodiment 23, wherein the second component is a proteinaceous component.

Embodiment 25. The conjugate of embodiment 23, wherein the second component is a nonproteinaceous component.

Embodiment 26. The conjugate of any of embodiments 23-25 wherein the second component is a therapeutic or diagnostic agent.

Embodiment 27. A fusion protein comprising a sialic acid-recognizing affinity reagent of any of embodiments 1 to 22.

Embodiment 28. An affinity matrix comprising a sialic acid-recognizing affinity reagent, conjugate or fusion protein of any of the preceding embodiments.

Embodiment 29. The affinity matrix of embodiment 28 selected from the group consisting of a solid support, surface, column, resin, bead, microarray, particle and nanoparticle.

Embodiment 30. A kit comprising a sialic acid-recognizing affinity reagent, conjugate, fusion protein or affinity matrix of any of the preceding embodiments, and instructions for use.

Embodiment 31. An isolated polynucleotide encoding a sialic acid-recognizing affinity reagent or conjugate of any of embodiments 1 to 24, or the fusion protein of embodiment 27.

Embodiment 32. A vector comprising a polynucleotide of embodiment 31.

Embodiment 33. The vector of embodiment 32, wherein the vector is an expression vector.

Embodiment 34. A host cell comprising a vector of embodiment 32 or 33.

Embodiment 35. The host cell of embodiment 34, wherein the host cell is a bacterial cell.

Embodiment 36. A method for making the sialic acid-recognizing affinity reagent or conjugate of any of embodiments 1-24, or the fusion protein of embodiment 27, the method comprising expressing the affinity reagent, conjugate or fusion protein in host cell.

Embodiment 37. A method for detecting a sialic acid component of a glycan, the method comprising:
    contacting a biological or laboratory sample with a sialic acid-recognizing affinity reagent, conjugate or fusion protein of any of embodiments 1-27 under conditions to allow binding of the affinity reagent, conjugate or fusion protein to the sialic acid; and detecting the sialic acid.

Embodiment 38. The method of embodiment 37, wherein the biological or laboratory sample comprises a recombinant antibody.

Embodiment 39. The method of embodiment 37, wherein the glycan is a biomarker.

Embodiment 40. The method of embodiment 39, wherein the biomarker is a cancer biomarker.

Embodiment 41. A method for enriching, isolating or purifying a sialic acid-containing glycan, the method comprising:
    contacting a sialic acid-recognizing affinity reagent, conjugate or fusion protein of any of embodiments 1-27 under conditions to allow binding of the affinity reagent, conjugate or fusion protein to the sialic acid so as to yield an enriched, isolated or purified sialic acid-containing glycan.

Embodiment 42. A diagnostic or therapeutic composition comprising a sialic acid-recognizing affinity reagent, conjugate or fusion protein of any of embodiments 1-27.

Embodiment 43. The diagnostic or therapeutic composition of embodiment 42 wherein the sialic acid-recognizing affinity reagent, conjugate or fusion protein is detectably labeled.

Embodiment 44. The diagnostic or therapeutic composition of embodiment 43 wherein the detectable label comprises a radioactive label, a fluorescent label, a phosphorescent label, a colorimetric label, an enzymatic label, an immunological label, a magnetic label, a paramagnetic label, a diamagnetic label or an electromagnetic label.

Embodiment 45. Use of a sialic acid-recognizing affinity reagent, conjugate or fusion protein of any of embodiments 1-27 as a therapeutic agent.

Embodiment 46. Use of a sialic acid-recognizing affinity reagent, conjugate or fusion protein of any of embodiments 1-27 as a diagnostic agent.

Embodiment 47. Use of a sialic acid-recognizing affinity reagent, conjugate or fusion protein of any of embodiments 1-27 for targeted drug delivery.

Embodiment 48. Use of a sialic acid-recognizing affinity reagent, conjugate or fusion protein of any of embodiments 1-27 for detection of the presence or amount of sialic acid in a biological or laboratory sample.

Embodiment 49. A compound, composition, or method including one or more of the features described herein.

The present invention is illustrated by the following examples. It is to be understood that the particular examples, materials, amounts, and procedures are to be interpreted broadly in accordance with the scope and spirit of the invention as set forth herein.

EXAMPLES

Example I. Pan-Specific Sialic Acid Reagents

Introduction

At present multiple lectins (typically from *S. Nigra*, *M. amurensis*, and wheat germ) have to be employed in serial lectin affinity chromatography to enrich sialylated glycans [2]. Because these lectins (especially WGA and MAL) show cross-reactivity with non-sialylated glycans [3, 4] their use risks capturing irrelevant components. The Sia-PS1 Lectenz® (PS=pan-specific) is under development for the detection and enrichment of general sialo-glycoconjugates regardless of terminal Neu5Ac (Siaα2,3-, α2,6-, and α2,8-) linkages to the adjacent saccharide. To our knowledge, this is the first reagent that is pan-specific for sialic acid (Sia, neuraminic acid, Neu5Ac), and as such, it has the potential to significantly enhance sialo-glycan biomarker detection and glycomics enrichment.

Methods

The flowchart presented in FIG. 2 outlines schematically the methods employed in Example I and II to screen, optimize and select the Lectenz® candidates. The specificity and affinity of potential Lectenz® candidates is evaluated through structurally-guided site-specific and/or site-saturation mutagenesis assays designed to enable the selection of optimal clones. Bio-layer Interferometry (BLI) is used to determine the binding kinetics and affinities for binding to glycans and glycoproteins. Affinity chromatography is performed by immobilizing the Lectenz® candidates in a column format to evaluate their ability to fractionate sialylated- and asialo-glycans and glycoconjugates. All promising Lectenz® candidates are screened against the glycan array at the CFG, which currently contains over 600 O- and N-linked glycans.

Results and Conclusions

Computational Simulation of Enzyme-Ligand Complexes Predicted Sia-PS1 Specificity NanB is a well-characterized enzyme that recognizes sialylated glycan substrates. Its sequence and additional characteristics have been previously described in the literature [9]. Computational simulations [10] were employed to identify residues in NanB that are most likely to be suitable to mutagenesis for substrate affinity optimization. The 3D models shown in FIG. 3A were built using the online tools at GLYCAM-Web (www.glycam.org).

After ligand alignment, the enzyme-ligand complexes were subjected to fully solvated molecular dynamics (MD) simulation [11-13], followed by calculation of average interaction energies using molecular mechanics-generalized Born surface approximation (MM-GBSA) method [12, 14]. See Table 1 for a list of NanB free energies for selected amino acids bound to 3'-sialyllactosamine (Neu5Acα2, 3Galβ1, 4GlcβNAc, or 3'SLN). The simulation analysis indicates that Sia-PS Lectenz® should display significant affinity for sialylated glycans with no measurable affinity for non-sialylated glycans. The generated Sia-PS Lectenz® are listed in Table 2, which also identifies mutagenesis site sequence identities. Table 3 lists the differing physical and chemical properties of these Sia-PS Lectenz® reagents.

TABLE 1

Per-residue binding free energies (kcal/mol) for WT NanB bound to 3'SLN.
Residues listed contributed at least 0.5 kcal/mol to either the total molecular
mechanical energies via van der Waals forces ($\Delta E_{VDW}$) or electrostatic ($\Delta E_{ELE}$)
interactions, or to the total binding free energy ($\Delta G_{Binding}$). Library columns apply
to Example II, and indicate residues selected for optimization for knowledge-
based library design (X-C-P = any amino acids for mutagenesis, but Cys or Pro;
X-C-E-P = any amino acids, except Cys, Glu, or Pro).

| Residues Important for Binding | $\Delta E_{VDW}$ | $\Delta E_{ELE}$ | $\Delta G_{GB-SA}$ | $\Delta G_{Binding}$ | Library 1 | Library 2 | Library 3 |
|---|---|---|---|---|---|---|---|
| R619 | 0.5 | −47.3 | 40.0 | −6.8 | | | |
| W674 | −4.7 | 0.7 | −0.4 | −4.3 | | | |
| R245 | −0.1 | −41.7 | 37.7 | −4.2 | | | |
| R676 | −2.4 | −23.6 | 22.7 | −3.2 | | | |
| Y653 | −1.9 | 0.4 | −0.6 | −2.2 | | | |
| S675 | −0.1 | −2.3 | 1.0 | −1.5 | | | |
| R264 | −0.2 | −27.7 | 26.6 | −1.3 | | | |
| H269 | −0.9 | −1.3 | 0.9 | −1.2 | | | |
| I246 | −1.0 | −0.8 | 0.8 | −1.0 | | | |
| I326 | −0.9 | −0.6 | 0.6 | −0.9 | | | |
| R557 | −0.4 | −28.3 | 27.9 | −0.7 | | | |
| D327 | −0.5 | 6.1 | −6.3 | −0.7 | X-C-P | X-C-P | X-C-P |

TABLE 1-continued

Per-residue binding free energies (kcal/mol) for WT NanB bound to 3'SLN. Residues listed contributed at least 0.5 kcal/mol to either the total molecular mechanical energies via van der Waals forces ($\Delta E_{VDW}$) or electrostatic ($\Delta E_{ELE}$) interactions, or to the total binding free energy ($\Delta G_{Binding}$). Library columns apply to Example II, and indicate residues selected for optimization for knowledge-based library design (X-C-P = any amino acids for mutagenesis, but Cys or Pro; X-C-E-P = any amino acids, except Cys, Glu, or Pro).

| | $\Delta E_{VDW}$ | $\Delta E_{ELE}$ | $\Delta G_{GB-SA}$ | $\Delta G_{Binding}$ | Library 1 | Library 2 | Library 3 |
|---|---|---|---|---|---|---|---|
| Tepid residues making only weak contributions | | | | | | | |
| E541 | −0.9 | 21.8 | −21.6 | −0.6 | X-C-E-P | X-C-E-P | X-C-E-P |
| E669 | −0.1 | 23.5 | −23.9 | −0.6 | | | |
| S673 | −1.1 | 2.4 | −2.0 | −0.6 | X-C-P | X-C-P | X-C-P |
| T539 | −0.7 | −1.4 | 1.7 | −0.5 | | | |
| L679 | −0.5 | −0.6 | 0.6 | −0.5 | | | |
| T268 | −0.4 | 1.4 | −1.4 | −0.4 | | | |
| P492 | −0.4 | 0 | 0.1 | −0.4 | | | |
| D270 | −2.3 | 18.5 | −16.5 | −0.4 | X-C-P | X-C-P | X-C-P |
| Y671 | −0.2 | 0.9 | −1.0 | −0.2 | | | |
| A538 | −0.2 | −1.1 | 1.3 | 0 | X-C-P | X-C-P | X-C-P |
| N353 | −0.1 | −0.7 | 0.7 | 0 | | | |
| N316 | −0.3 | 0.4 | −0.1 | 0 | | | |
| P660 | 0.0 | −0.1 | 0.1 | 0 | | | |
| N683 | −4.7 | −0.3 | 0.3 | 0 | | | |

TABLE 2

Figures 7A, 7B, 7C:
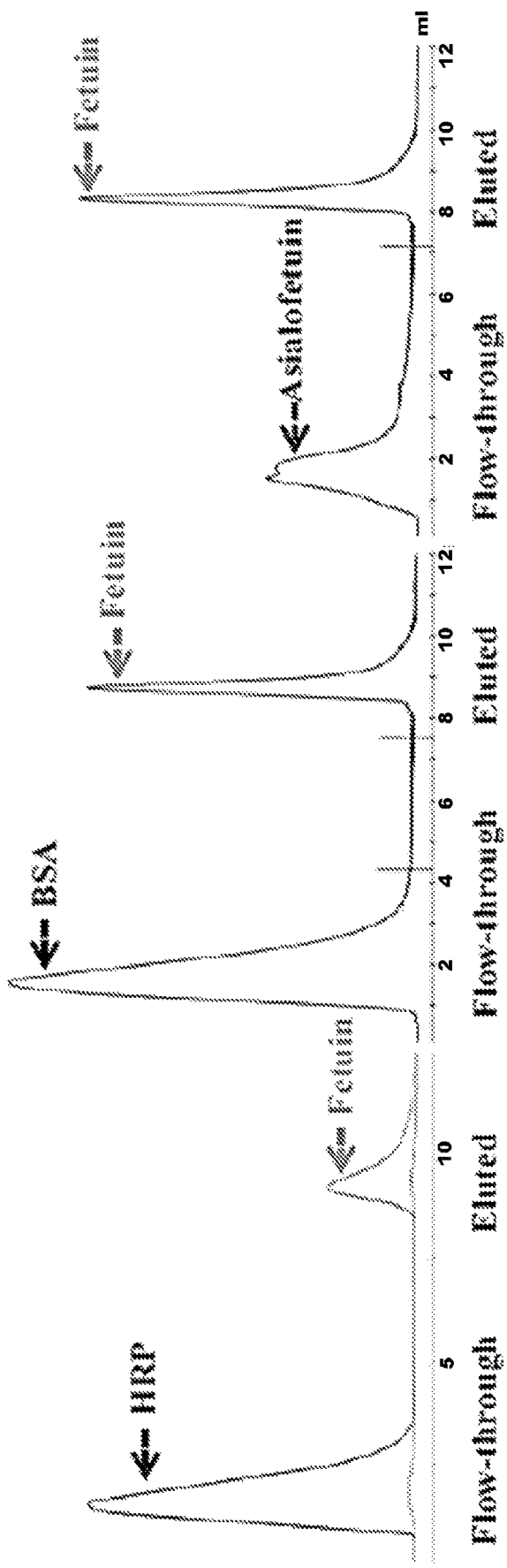

Site mutations of selected pan-specific sialic acid-recognizing Lectenz® reagents based on NanB. The shaded boxes indicate retention of the wild type amino acid at that site.

| wtNanB | D270 | E541 | Y653 |
|---|---|---|---|
| Sia-PS1 | D | E | F |
| Sia-PS2 | A | E | Y |
| Sia-PS3 | N | E | Y |
| Sia-PS4 | D | A | Y |
| Sia-PS5 | D | Q | Y |

TABLE 3

Physical and chemical properties of NanB and pan-specific sialic acid recognizing Lectenz ® reagents. ExPASy ProtParam calculated properties based on amino acid sequence are reported. [15] Molecular weight, isoelectric point, and extinction coefficients (ε) values are listed.

| Proteins (690 Amino Acids) | Molecular Weight | Isoelectric Point | ε (M-1 cm-1) | ε (L g-1 cm-1) | ε 1% |
|---|---|---|---|---|---|
| wtNanB | 76965.9 | 6.53 | 97640 | 1.269 | 12.69 |
| Sia-PS1 | 76949.9 | 6.53 | 96150 | 1.250 | 12.50 |
| Sia-PS2 | 76921.9 | 6.67 | 97640 | 1.269 | 12.69 |
| Sia-PS3 | 76964.9 | 6.67 | 97640 | 1.269 | 12.69 |
| Sia-PS4 | 76907.9 | 6.67 | 97640 | 1.270 | 12.70 |
| Sia-PS5 | 76964.9 | 6.67 | 97640 | 1.269 | 12.69 |

Sia-PS Lectenz® have No or Attenuated Enzymatic Activity

The neuraminidase activity of the wt NanB enzyme and its mutants was measured using, pNP-Neu5Ac as a colorimetric substrate. As shown in FIG. 4, in comparison to the wild type enzyme, Sia-PS3 was 19% active, Sia-PS2 was 9% active and others were inactive. Thus, Sia-PS1, Sia-PS4 and Sia-PS5 are suitable Lectenz® candidates.

Sia-PS Lectenz® Reagents have Unique Target Affinity

Steady-state binding constants between Lectenz® candidates and sialic acid ligands were measured by BLI. FIG. 5 showed that Sia-PS4 has the highest binding response with a sub-micromolar KD value to 3'SL while Sia-PS2, a candidate that has residual neuraminidase activity, has the lowest binding response with a higher KD value. The five candidates' binding to 6'-sialyllactose (Neu5Acα2,6Galβ1, 4Glcβ, or 6'SL) yielded similar KD values, albeit at a reduced binding response (FIG. 6). Notably, the affinity of Sia-PS1, Sia-PS4, and Sia-PS5 to 3'SL or 6'SL is comparable or superior to reported values for the lectins MAL (KD ~1-3 μM [16, 17]) and SNA (0.6-0.9 μM [16]).

Sia-PS1 Detects Neu5Ac Independent of Linkage

Additional BLI measurements confirmed that Sia-PS1, Sia-PS2, Sia-PS3, Sia-PS4, and Sia-PS5 recognizes Neu5Acα2,3-, α2,6-, and α2,8-linkages present in 3'SL, 6'SL and the oligosaccharide of ganglioside GD3 (Neu5Acα2,8Neu5Acα2,3Galβ1, 4Glcβ), respectively. The binding affinity is micromolar or sub-micromolar for each of the oligosaccharides (FIG. 6).

Lectenz® Affinity Chromatography

A typical application of the Lectenz® we are developing is using affinity chromatography of complex samples for biomarker enrichment. The low KD value and off rate for Sia-PS1 ($k_{off}$=0.008 s−1) make it ideal as a matrix for affinity chromatography. Indeed, in Lectenz® Affinity Chromatography (LAC), Sia-PS1 coupled to a Sepharose column did not retain any non-sialylated glycoprotein horseradish peroxidase (HRP); all of it was in the flow-through. In contrast, sialylated fetuin was retained on the column and eluted (FIG. 7A). In 1:1 mixtures, the column captured sialylated fetuin, while non-sialylated BSA or de-sialylated asialofetuin flows through the column at the analyte's loading step (FIGS. 7B and 7C).

Figure 6:
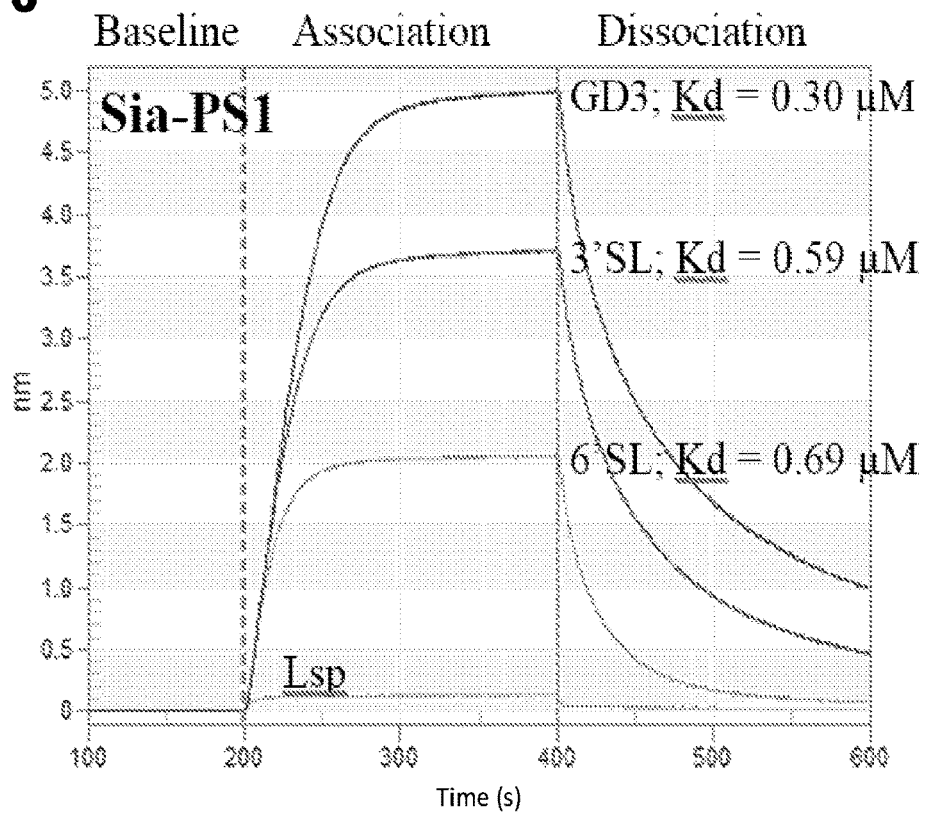
FIG. 6 shows BLI sensograms for the binding of Sia-PS Lectenz® candidates (analytes) to immobilized oligosaccharides. Lsp=lactose (no sialic acid), 3'SL=α2,3-sialyllactose, 6'SL=α2,6-sialyllactose, GD3=GD3 oligosaccharide that contains a terminal α2,8-linked Neu5Ac residue and an internal α2,3-linked Neu5Ac residue. For example, Sia-PS1 analyte exhibits a steady-state $K_D$ (3'SL)=0.59 µM, $K_D$ (6'SL)=0.69 µM, $K_D$ (GD3)=0.30 µM.
Figure 6:
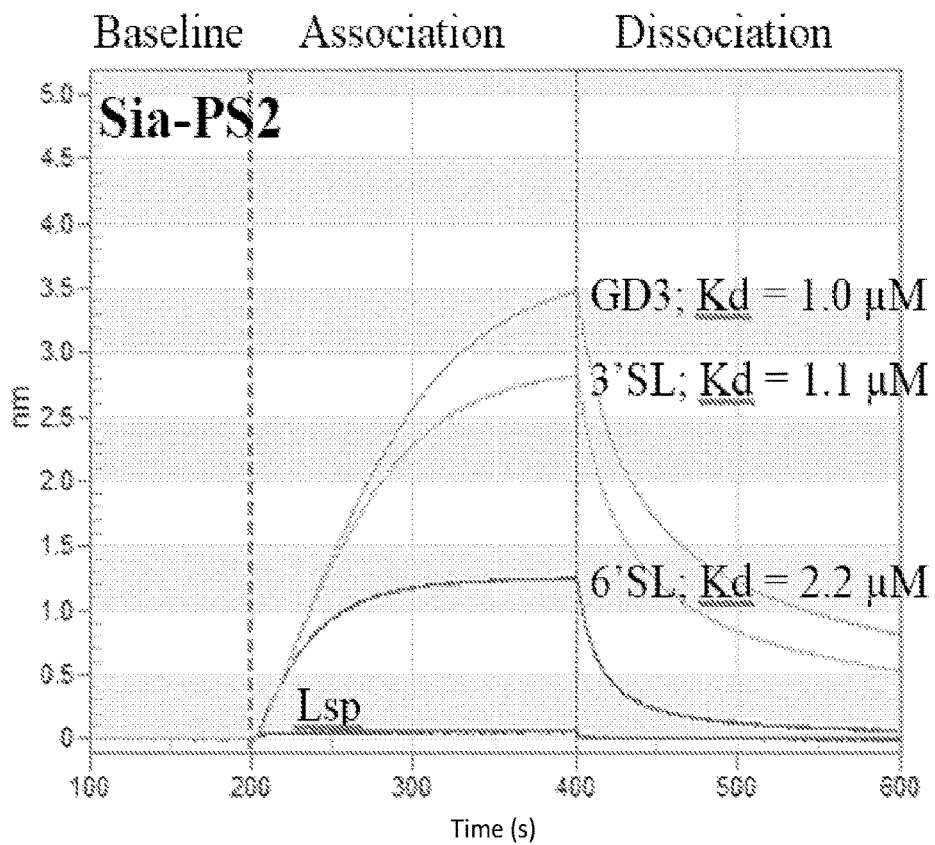
Figure 6:
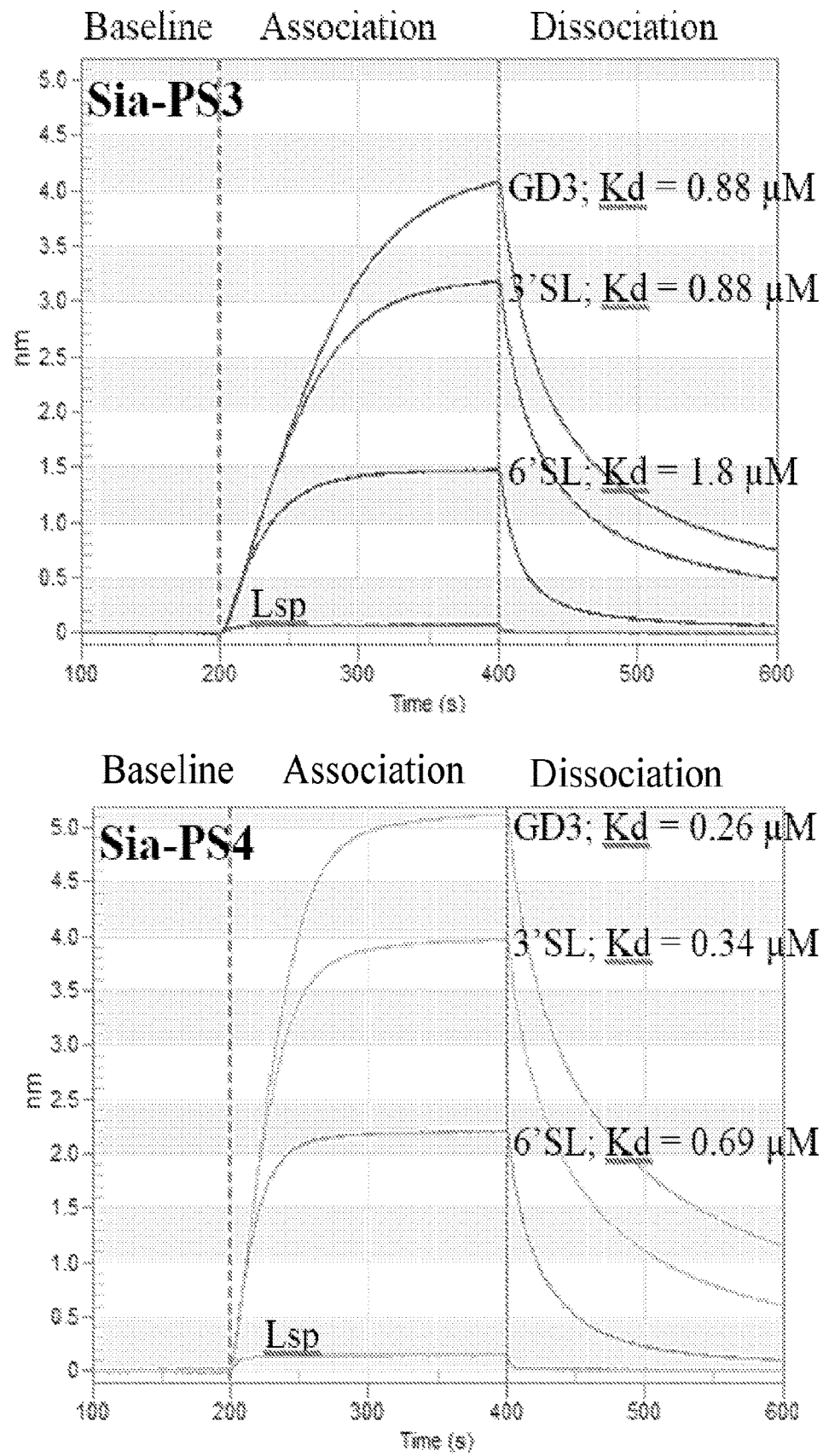
Figure 6:
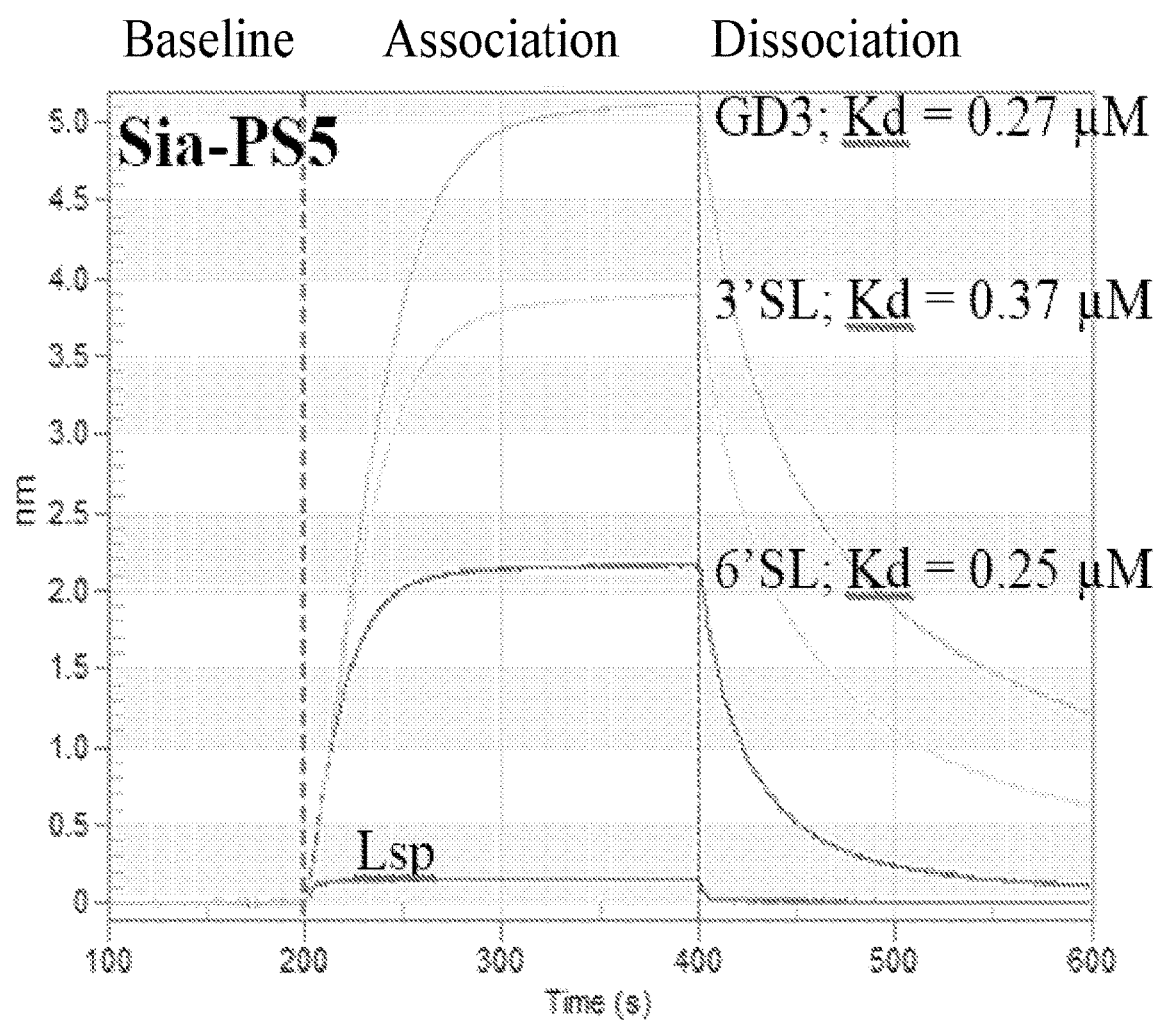
Figure 8A:
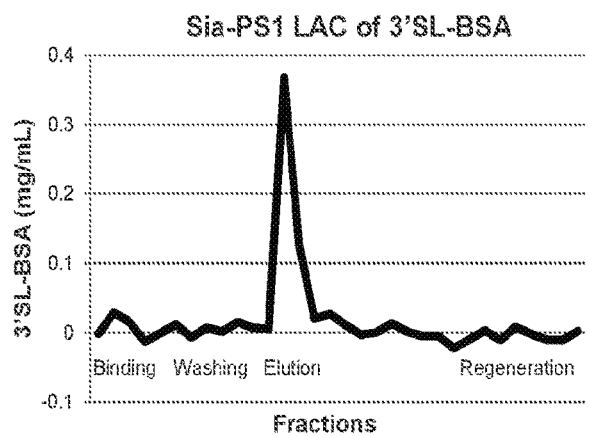
Figure 8B:
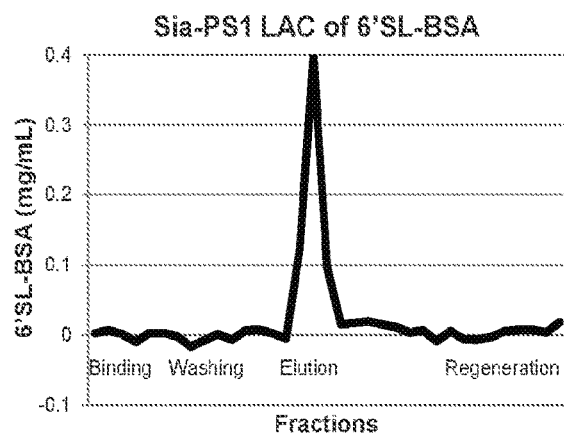
FIGS. 9A and 8B show elution profiles for standard lectin affinity columns and synthetic neoglycoproteins.

Sia-PS1 Specifically Binds to Both 3'-Sialylated and 6'-Sialylated Glycoproteins In addition to the BLI data (FIG. 6), we conducted LAC using synthetic sialylated glycoproteins (neoglycoproteins), 3'-sialyllactose-BSA (3'SL-BSA) and 6'-sialyllactose-BSA (6'SL-BSA), as the analytes. The Sia-PS1 Lectenz® column was able to capture each of the neoglycoproteins that were subsequently eluted by 3'SL and 6'SL, respectively (FIG. 8).

Figure 9A:
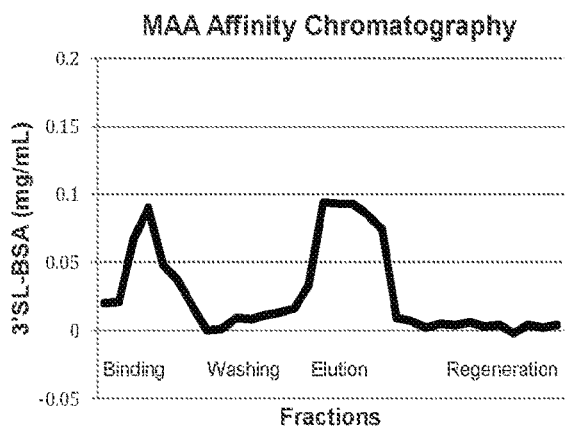
Figure 9B:
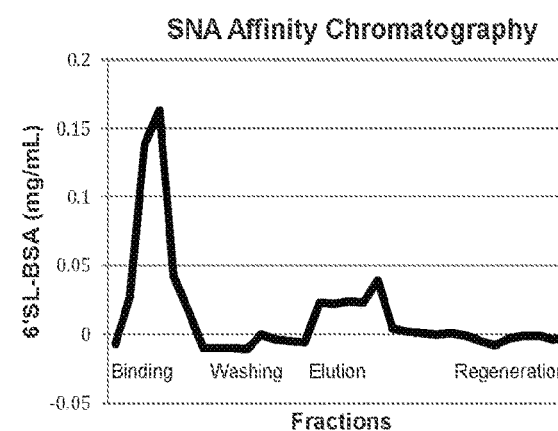
FIG. 9B shows an elution profile for 6'-sialyllactose-BSA (200 µg) from a commercially available SNA column.

Sia-PS1 is Superior to Lectins as an Enrichment Reagent for Sialo-Glycoconjugates For comparison, commercially available affinity columns (1 mL) of MAA (known as 3'Sia-specific) and SNA (known as 6'Sia-specific) were loaded with 3'SL-BSA and 6'SL-BSA, respectively, at the recommended loading levels of 200 µg analyte in 1 mL loading buffer. As evident in FIG. 9, while each column retained some of the neoglycoconjugates, significant amounts were observed in the flow-through fractions. According to the manufacturer's technical data, the binding capacity of the lectin columns far exceeds the 200 µg glycoproteins loaded. In addition, the elution peaks are far broader than those eluted from Sia-PS1 LAC (FIG. 8). Although a number of factors, such as the quality of the lectin columns, or the incompatibility between the immobilized lectins and the neoglycoconjugate analytes, or the manufacturer's recommended eluant might have affected the results, these experiments do indicate the superiority of Sia-PS1 as an enrichment reagent for sialo-glycoconjugates.

Sia-PS1 Enriches Sialo-Glycoconjugates from MCF7 Cell-Free Extract

Figure 10C:
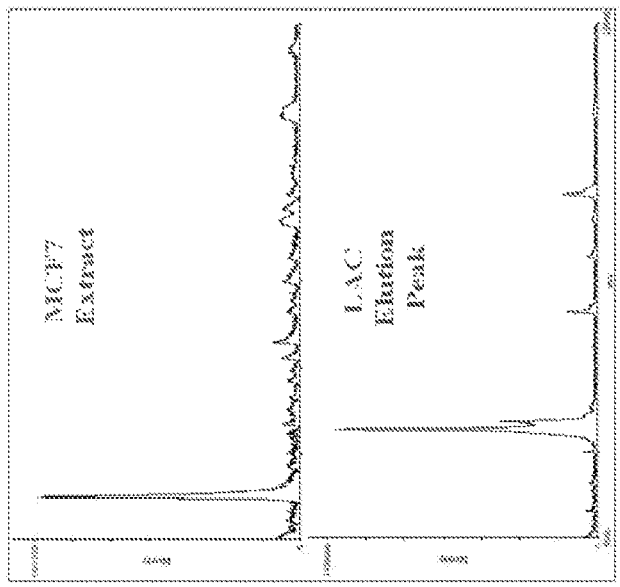
FIGS. 10A, 10B and 10C show Sia-PS1 LAC enrichment of sialo-glycoconjugates from MCF7 cell-free extract (CFE). A sample (approximately 500 µg) of the CFE, which was prepared according to Lee et al. [36], was loaded on to the Sia-PS1 LAC column (see FIG. 7), washed and competitive eluted by a 1:1 mixture of 3'SL and 6'SL at 50 mM each in loading buffer.
Figure 10B:
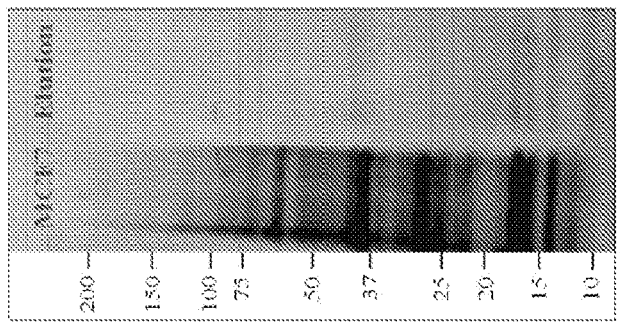
Figure 10A:
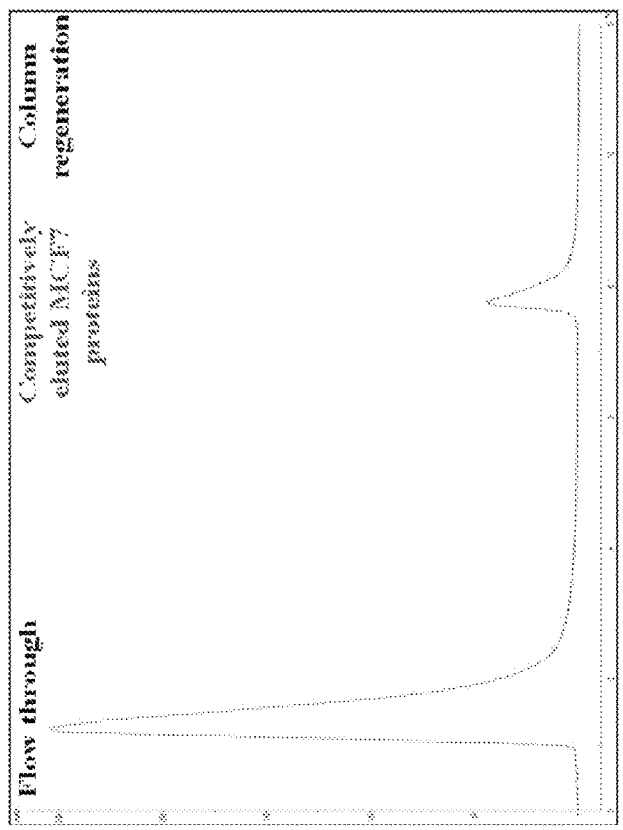

Application of Sia-PS1 LAC has been applied to enrichment of sialo-glycoconjugates from MCF7 cell-free extracts [18]. As shown in FIG. 10, about 10% of the total proteins in the MCF7 extract were affinitive to the Sia-PS1 LAC column and could be eluted by competitive reagent 3'SL & 6'SL. We were able to enhance binding efficiency by circulation of about 1.5 mg of MCF7 proteins through the column at 4° C. overnight, which resulted in an eluted peak of 207 µg proteins, or 13.8%. It is expected that comparison of the identity and relative abundance of the Sia-PS1 LAC-enriched proteins to known glycosylation databases will further demonstrate the specificity and effectiveness of Sia-PS1 as a biomarker discovery reagent.

Figure 11:
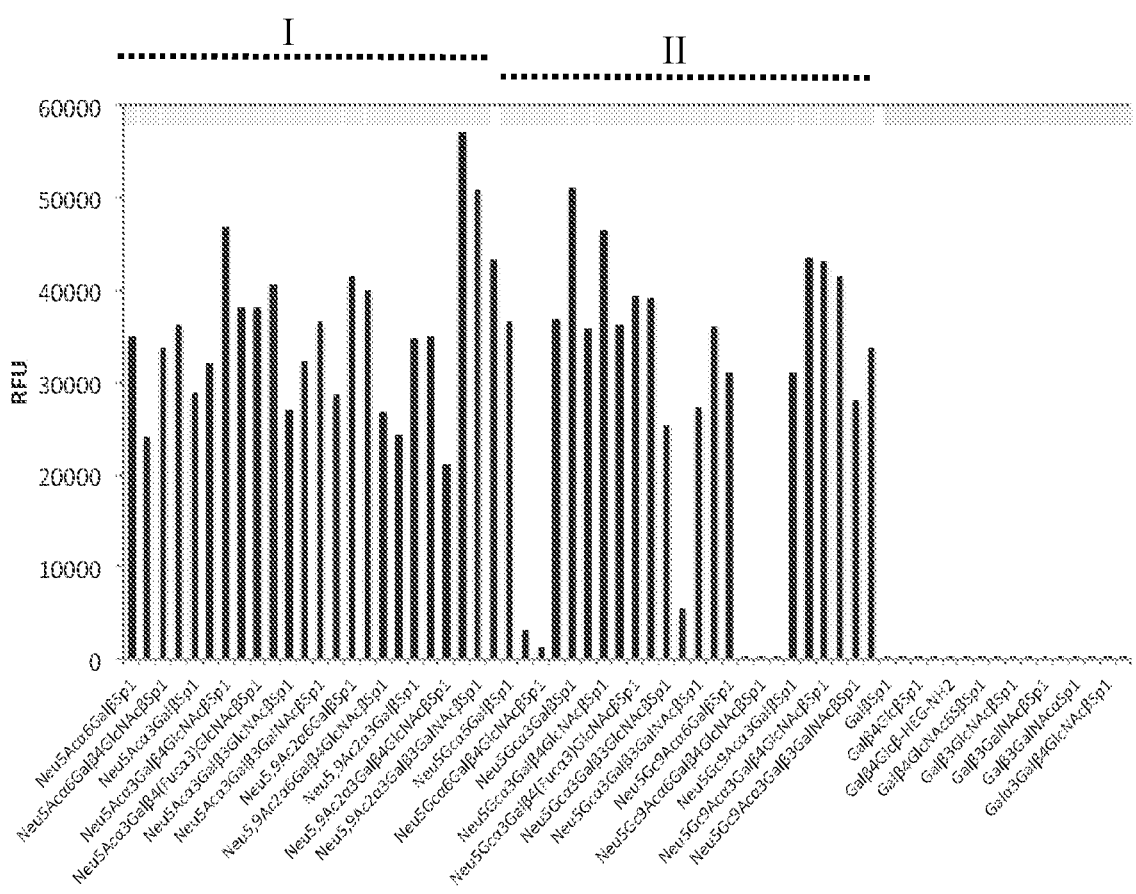
FIG. 11 shows glycan array screening results for Sia-PS1 indicating the ability to specifically recognize all sialylated glycans (Neu5Ac-glycans) on the array (I) and many non-human Neu5Gc-Sia glycans (II).

Glycan Array Screening Confirms Sia-PS1 Lectenz® Specificity for Sialo-Glycans Glycan array screening was performed using a biotinylated Sia-PS1 Lectenz® sample at a 200 µg/mL concentration on a sialoglycan microarray with approximately 64 glycan structures [19]. Secondary detection was achieved with streptavidin-Cy3 and the experiment was carried out as previously described. The specificity data (FIG. 11) confirm binding to all linkage variants of Neu5Ac on the array, including α2,3, α2,6 as well as to common modifications of Neu5Ac, such as 9-0 acetylation. Further, all variants of the N-glycolyl form of sialic acid (Neu5Gc, Gc-Sia) were detected, with the exception of some 9-O-acetylated structures. No signal was observed for non-sialylated terminal galactose structures, reaffirming the specificity of Sia-PS1 for sialic acid.

Western Blot Using Sia-PS1, Sia-PS4, and Sia-PS5 as Probes

Figure 18:
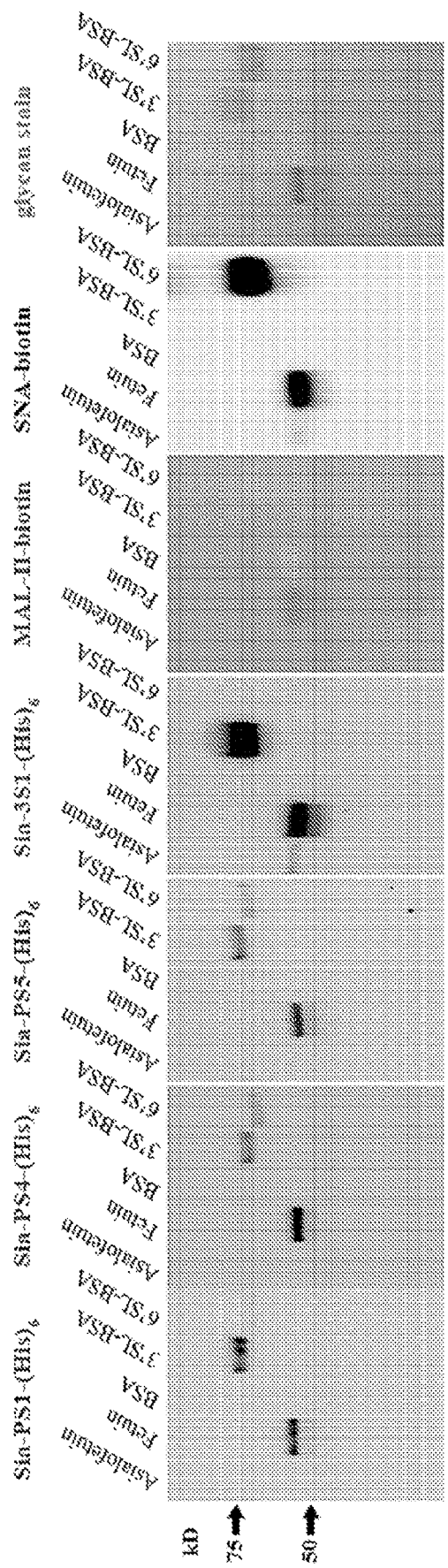
FIG. 18 shows that Sia-PS1, Sia-PS4, Sia-PS5, and Sia-3S1 bind to their corresponding glycoconjugates.

A sample (1 µg each) of asialofetuin, fetuin, BSA, 3'SL-BSA or 6'SL-BSA was run on an SDS-PAGE gel. The gel was transferred to a nitrocellulose membrane and blocked. Sia-Lectenz® at 1 µM each was incubated with the blot to probe for terminal sialic acid. After washing, anti-Poly His-HRP conjugate was incubated with the blot to detect the N-terminal hexa-histidine tag of Sia-PS1. The blot was washed and developed with a chemiluminescent substrate. The image (FIG. 18) shows that Sia-PS1, Sia-PS4, and Sia-PS5 bind sialylated proteins fetuin, 3'SL-BSA, and 6'SL-BSA, but not non-sialylated proteins asialofetuin and BSA. For comparison, commercial biotinylated lectins MAL II and SNA, known to be specific for SiaαSiaα2,3- and Siaα2,6 linkages, respectively, were used as probes. HRP streptavidin was used as the secondary detection reagent. The lectins did not bind their non-cognate BSA neoglycoprotein. This demonstrates that the Sia-PS Lectenz® are pan-specific, unlike the commercial lectins.

Summary

1) Computational modeling provides structural insights relevant for converting the wt NanB parent enzyme to catalytically inactive pan-specific sialic acid Lectenz® reagents.
2) All pan-specific Lectenz® candidates have significantly diminished or un-detected catalytic activity relative to the wt parent enzyme. Notably, the lead candidate Sia-PS1 is catalytically inactive.
3) The Sia-PS Lectenz® reagents have unique affinity, with Sia-PS1 having the highest affinity.
4) The Sia-PS1 Lectenz® is pan-specific for Siaα2,3-, α2,6-, and α2,8-linkages present in 3'SL, 6'SL, and GD3 glycan (Neu5Acα2,8Neu5Acα2,3Galβ1, 4Glc) with sub-micromolar affinity for all three target glycan structures.
5) The Sia-PS1 Lectenz® is a functional capture reagent for the enrichment of fetuin from 50:50 mixtures of fetuin:asialofetuin and fetuin:BSA.
6) The Sia-PS1 Lectenz® is a functional capture reagent for the enrichment of both 3'-sialyllactose-BSA and 6'-sialyllactose-BSA glycoconjugates.
7) The Sia-PS1 Lectenz® is a superior capture reagent for the enrichment of sialo-glycoconjugates compared to the lectins MAA and SNA.
8) The Sia-PS1 Lectenz® is a functional capture reagent for the enrichment of sialo-glycoconjugates from a complex MCF7 breast cancer cell extract.
9) The Sia-PS1 Lectenz® exhibits binding to sialylated glycans and no binding is observed to non-sialylated terminal galactose bearing glycans via glycan array screen.

Example II. Reagents Specific for α2,3-Linked Sialic Acid

Introduction

The lectins *Maackia amurensis* leukoagglutinin (MAL) and hemagglutinin (MAH) are widely believed to be specific for the terminal glycan sequence Neu5Acα2,3Galβ. Yet remarkably, commercial Maackia lectins are often sold as mixtures, have multiple names (MAA, MAL I, MAL II, etc.), and have a range of reported specificities [5]. To fully define their specificity, these lectins have recently been screened against glycan arrays at the Consortium for Functional Glycomics, which confirmed that although they do bind to the Neu5Acα2,3Galβ sequence, they are equally able to bind to glycans terminating in other carbohydrates, including: 3S-Galβ, 3S-GalNAcβ, Neu5Gcα2,3Galβb, Neu5Acα2,8Neu5Gca, and Neu5Gcα2,8Neu5Gcα(MAL), and 3S-Galβ, KDNα2,3Galβ, but not Neu5Gcα (MAH). Given that terminal 3S-Galβ [6] and Neu5Gcα [7] modifications are both potential markers for cancers, the ability to distinguish normal Neu5Acα2,3Galβ sequences from others is critical. Furthermore, the presence of the normal "α2,3" sequence in certain glycoproteins can correlate with disease, as in the case of prostate specific antigen (PSA) [8]. In this report, we illustrate the development of an α2,3-sialic acid specific Lectenz® reagent, Sia-3S1. Furthermore, we demonstrate its potential as a capture reagent for Lectenz® affinity chromatography applications.

Methods

The methods are as described in in Example I.

RESULTS AND CONCLUSIONS

Library Construction

Figure 12:
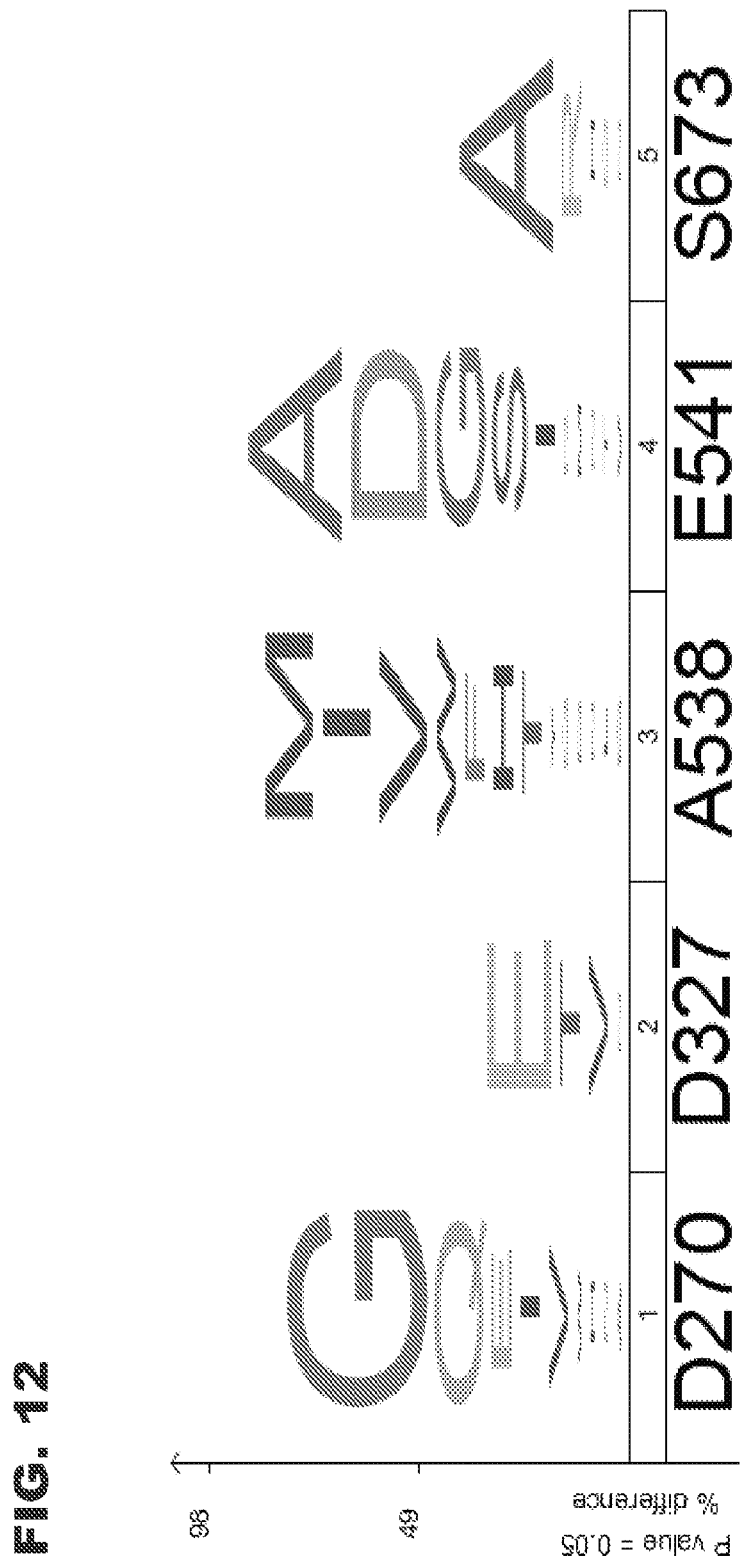
FIG. 12 shows amino acid iceLogo of enriched clone sequences. The wildtype sequence is shown across the bottom. Preferred amino acids at the five randomized positions are shown as a graphical representation. Y-axis indicates percentage of detection (% difference) for each amino acid. The prevalence of wild-type sequence at D237 and S673 is ignored by the iceLogo, hence a blank space at the top of the iceLogo for these positions.
Figure 13:
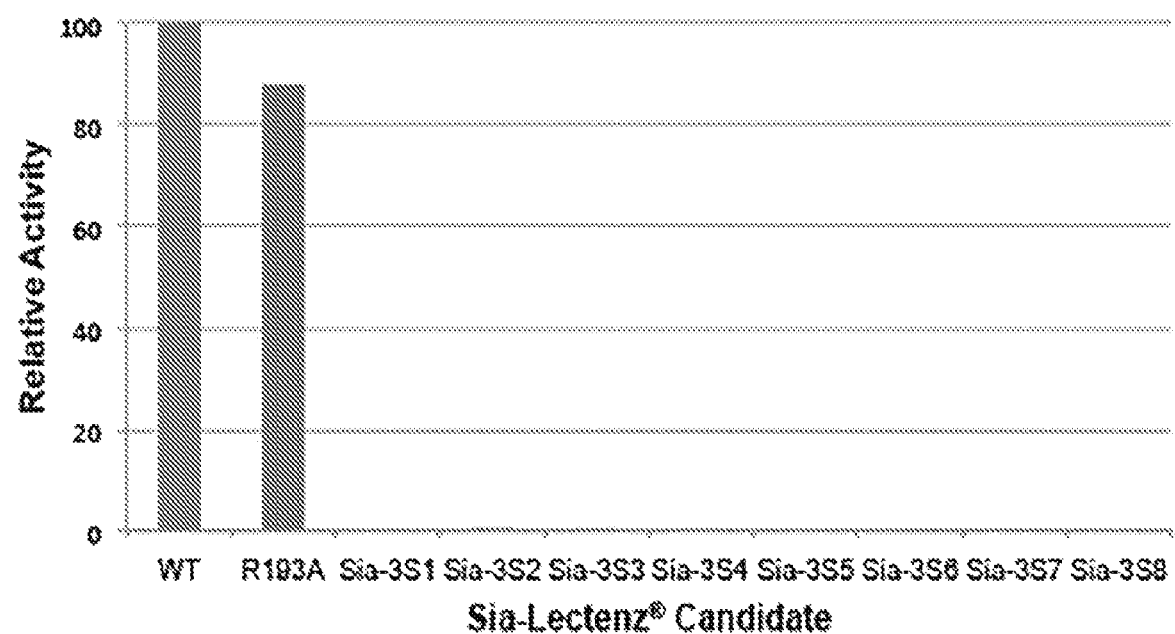
FIG. 13 shows enzymatic activity of wild-type (wt) NanB, the R193A point mutant, and Sia-3 S Lectenz® candidates.

Using computationally-guided directed evolution (FIG. 2, Example I), multiple Lectenz® candidates with varying specificity for 3'SL over 6'SL have been identified. Three distinct yeast surface display libraries were constructed [1] using the WT NanB enzyme as the scaffold (Table 1). Specifically, the NanB enzyme was expressed as a fusion protein of Aga-2p on the yeast cell surface. These yeast libraries were constructed with site saturation mutagenesis at positions of interest as indicated in Table 1. Library 1 includes the NanB GH33 domain (residues 230-697). Library 2 includes the NanB CBM and GH33 domains (residues 30-697). Library 3 includes the same coverage as Library 2 with a R193A mutation. Library 2 and 3 were both biopanned against a 3'SL glycan target. Colonies from rounds 3, 6, and 9 were sequenced to identify enriched clones. Enriched yeast clones from library 3 were cloned into E. coli expression vectors for protein expression, purification, and characterization. Library 2 clones have also been sequenced and will be analyzed in a similar manner. An amino acid iceLogo representation of the candidates selected from library 3 is illustrated in FIG. 12, indicating prevalence of different amino acids at each library mutagenesis residue. These candidates all contain an Arginine 193 residue to Alanine mutation (R193A) in addition to library mutations that are identified in Table 4. This R193A mutation is located in the carbohydrate binding module of NanB and has 88% enzymatic activity of wt NanB (FIG. 13). We have previously observed attenuated binding of sialo-glycoconjugates when the R193A mutation is introduced into the Sia-PS1 Lectenz®. Taken together, introduction of the R193A mutation to the Sia-3S Lectenz® library prior to selection should attenuate pan-specific sialic acid binding, with little effect on candidate enzymatic activity. This will enhance enrichment of candidates that preferentially bind to 3'SL via directed evolution.

These Sia-3 S Lectenz® candidates are being characterized by BLI and their utility as capture reagents for enrichment of 2,3-linked sialic acid glycans is currently being assessed. A partial list of these Sia-3S Lectenz® is included in Table 4, along with their mutations. The amino sequences of these mutants are represented by wild-type sequence SEQ ID NO:4 in FIG. 3D modified at the amino acid sites as shown in Table 4. Physical and chemical properties of these candidate reagents are shown in Table 5.

TABLE 4

Site mutations of selected 3'-linkage specific sialic acid-recognizing Lectenz ® reagents from Library 3, based on NanB (R193A). The shaded boxes indicate retention of the wild type amino acid at that site.

| wtNanB | R193 | D270 | D327 | A538 | E541 | P660 | S673 | N683 |
|---|---|---|---|---|---|---|---|---|
| Sia-3S1 | A | Q | D | V | D | P | S | N |
| Sia-3S2 | A | G | D | W | D | Q | A | N |
| Sia-3S3 | A | G | D | V | D | P | A | N |
| Sia-3S5 | A | D | E | F | A | P | S | N |
| Sia-3S6 | A | G | D | H | A | P | S | S |
| Sia-3S7 | A | H | D | M | A | P | S | N |
| Sia-3S8 | A | I | V | F | I | P | Q | N |
| Sia-3S9 | A | G | D | I | S | P | A | N |

Sia-3 S7 additionally has mutations D427Y and L690F; however, these were not among the sites selected for mutation (based on Table 1) and, rather, are artifacts of cloning.

TABLE 5

Physical and chemical properties of NanB and 3'-linkage specific sialic acid recognizing Lectenz ® reagents. ExPASy ProtParam calculated properties based on amino acid sequence are reported. [15] Molecular weight, isoelectric point, and extinction coefficients (ε) values are listed.

| Proteins (690 Amino Acids) | Molecular Weight | Isoelectric Point | $\varepsilon$ (M$^{-1}$ cm$^{-1}$) | $\varepsilon$ (L g$^{-1}$ cm$^{-1}$) | $\varepsilon$ $^{1\%}$ |
|---|---|---|---|---|---|
| wtNanB | 76965.9 | 6.53 | 97640 | 1.269 | 12.69 |
| Sia-3S1 | 76907.9 | 6.53 | 97640 | 1.270 | 12.70 |
| Sia-3S2 | 76938.9 | 6.53 | 103140 | 1.341 | 13.41 |
| Sia-3S3 | 76820.8 | 6.53 | 97640 | 1.271 | 12.71 |
| Sia-3S5 | 76912.9 | 6.53 | 97640 | 1.269 | 12.69 |
| Sia-3S6 | 76803.8 | 6.70 | 97640 | 1.271 | 12.71 |
| Sia-3S7 | 76904.9 | 6.70 | 97640 | 1.270 | 12.70 |
| Sia-3S8 | 76964.1 | 6.84 | 97640 | 1.269 | 12.69 |
| Sia-3S9 | 76806.8 | 6.67 | 97640 | 1.271 | 12.71 |

Presented below is data for a promising lead Lectenz® candidate designated Sia-3S1.

Sia-3S Lectenz® have No Detectable Enzymatic Activity

We screened these candidates against wt NanB and the R193A point mutant to assess whether the identified Sia-3 S Lectenz® candidates exhibit neuraminidase activity. The colorimetric substrate pNP-Neu5Ac was used to measure activity. As shown in FIG. 13, in comparison to the wild type enzyme, no activity could be measured above background for the Sia-3 S Lectenz® candidates. Therefore, all Sia-3 S Lectenz® reagents are suitable candidates.

Sia-3S1 is Specific for 3'SL Over 6'SL

Figure 14A:
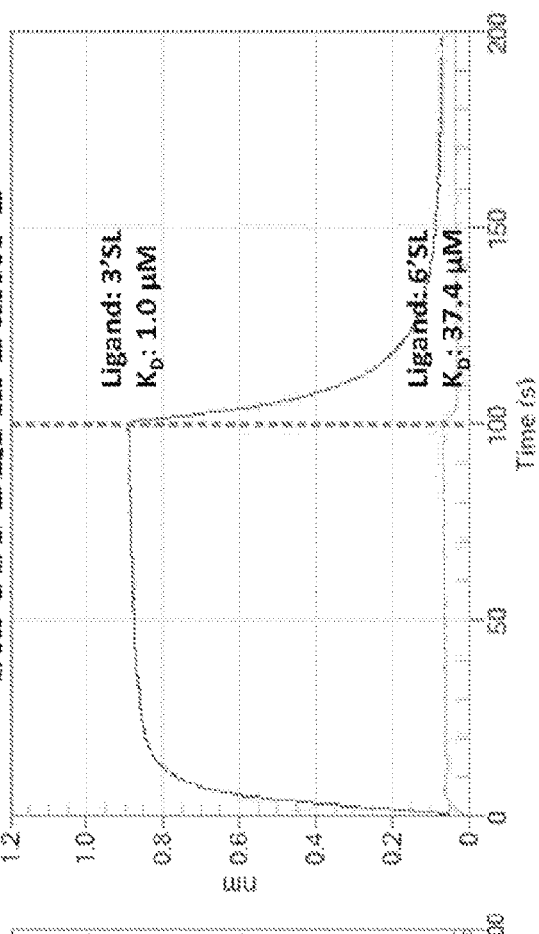
Figure 14B:
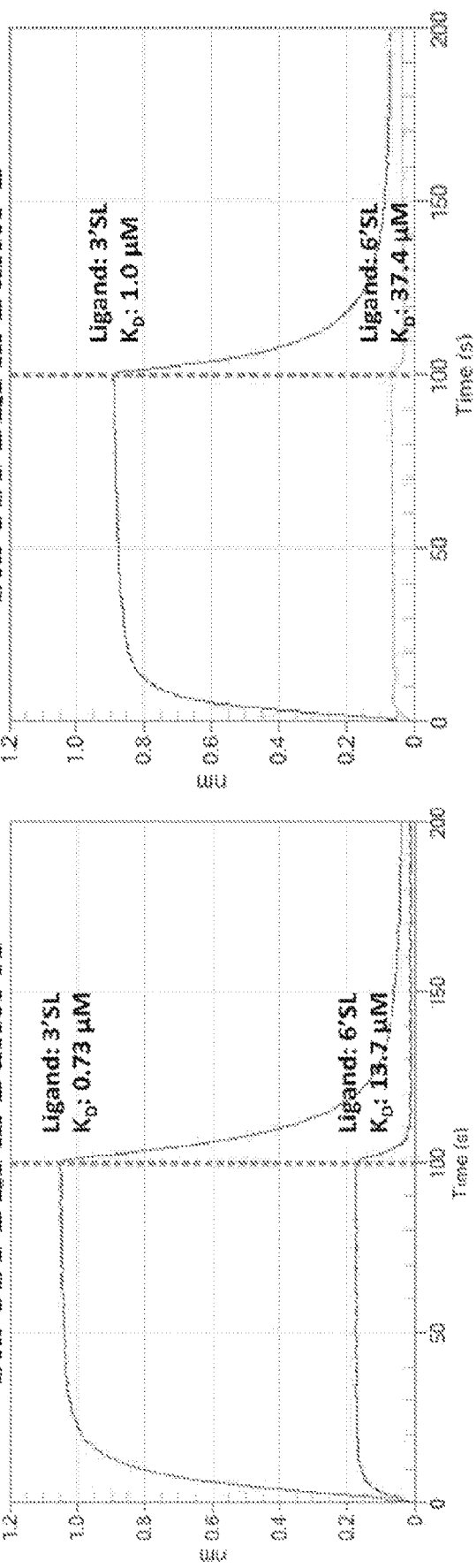

Sia-3S1, which is enzymatically inactive, exhibits high 3'SL affinity under well-defined conditions. FIG. 14 shows its BLI binding kinetics to 3'SL and 6'SL, respectively, in two different binding buffers.

Sia-3S1 Retains Fetuin and is Competitively Eluted Using 3'SL

Figure 15:
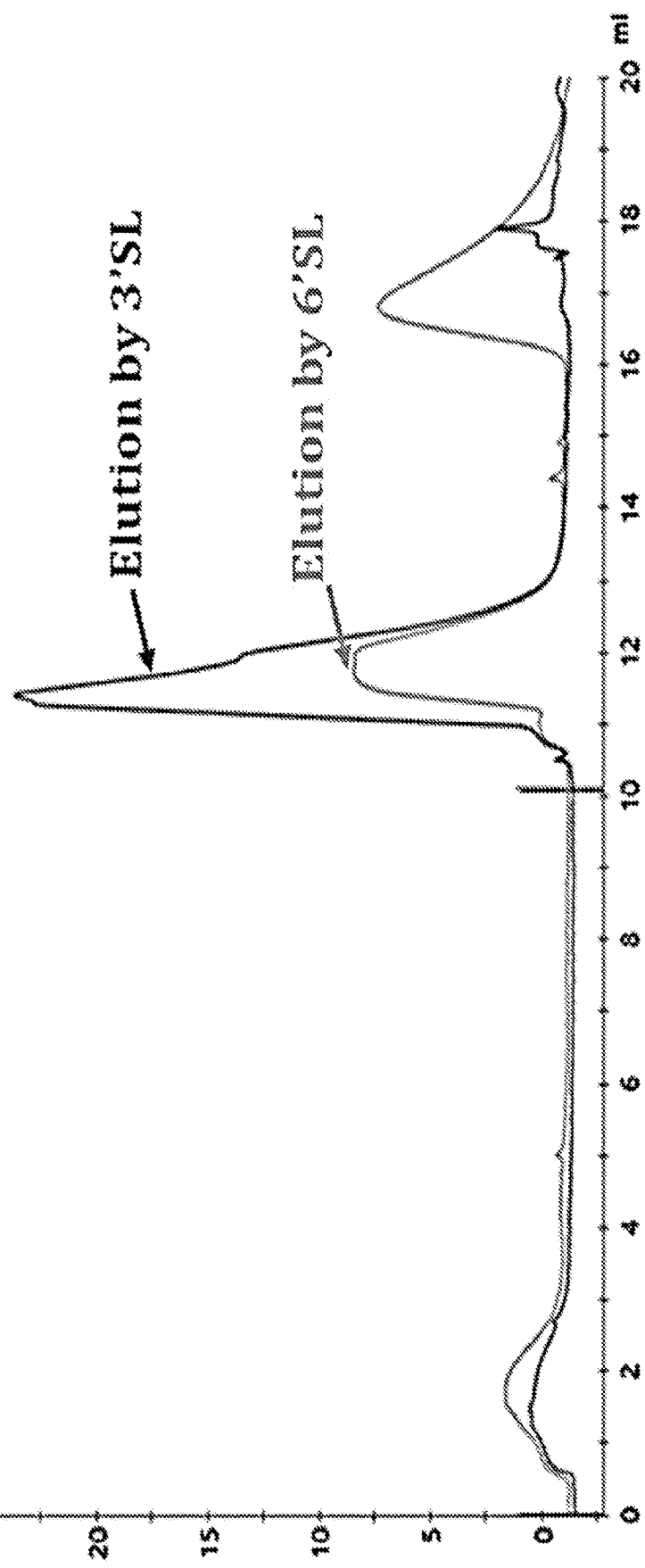
FIG. 15 shows differential elution of fetuin bound to a Sia-3S1 LAC column. Purified Sia-3S1 (2 mg) was covalently coupled to a 1-mL sepharose column, followed by loading of 100 µg fetuin. Fetuin molecules bound onto the Sia-3S1 column were competitively eluted with a 50 mM 3'SL or 6'SL solution in loading buffer. (The A280 UV spike at 18 mL retention volume is an instrument pump artifact.)

Preliminary Sia-3S1 LAC was performed on fetuin, a highly sialylated glycoprotein with both 3'-linked and 6'-linked sialic acid residues, followed by competitive elution with either 3'SL or 6'SL. As shown in FIG. 15, of the ~85 μg fetuin bound to the Sia-3S1 column, 100% was competitively eluted by 3'SL, while only 50% eluted by 6'SL. These results strongly indicate the 3'-linkage preference of Sia-3S1.

Figure 3B:
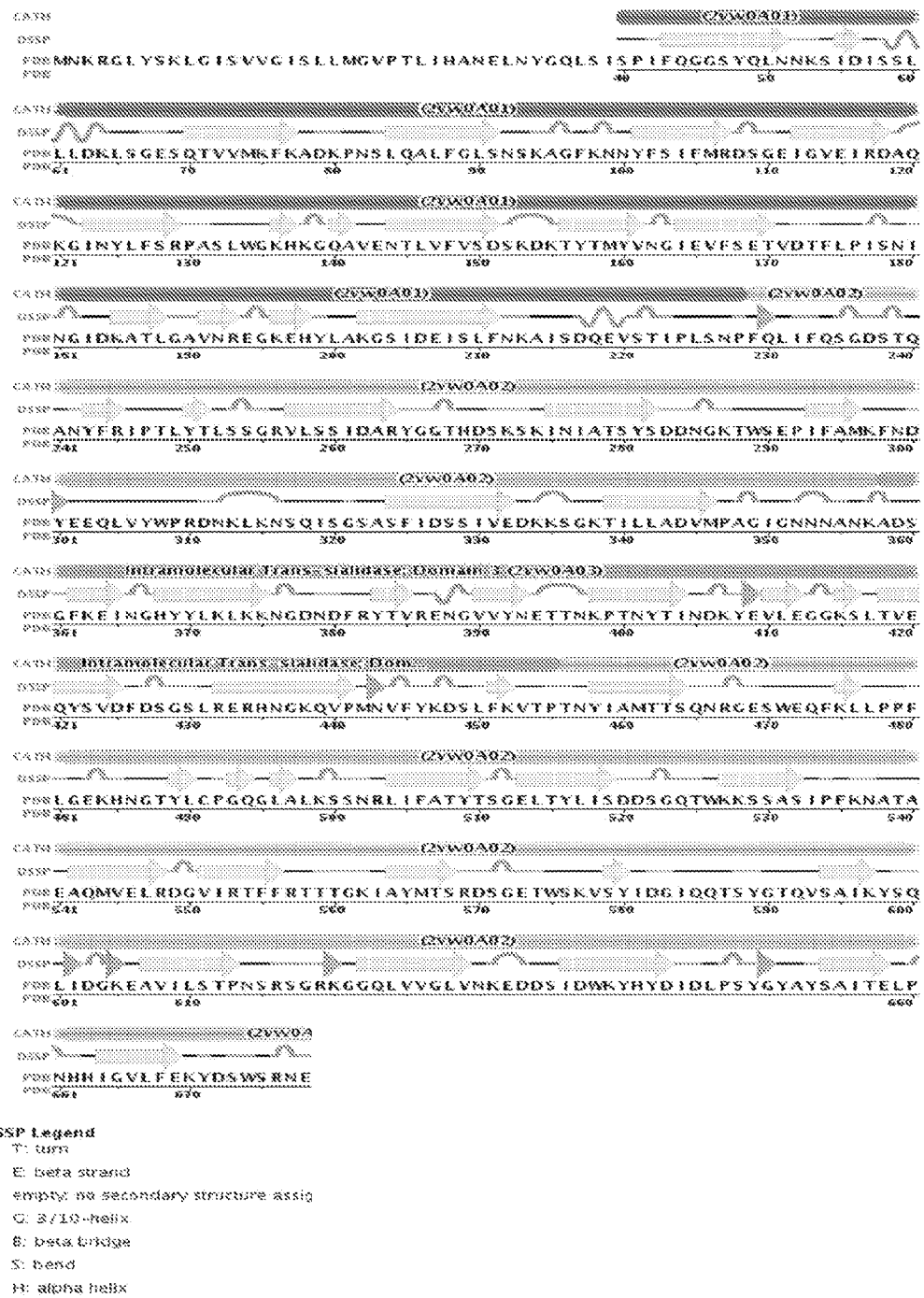
FIG. 3B shows a sequence display of wild-type *Streptococcus pneumoniae* NanB (PDB ID: 2vw0). The 697 amino acid sequence (SEQ ID NO:1) is depicted and annotated. The three domains are labeled 2vw0A01, 2vw0A02, 2vw0A03. The image is from the RCSB PDB (www.rcsb.org) of PDB ID 2vw0 (Xu et al., J. Mol. Biol., 2008, 384: 436-449).
Figure 4:
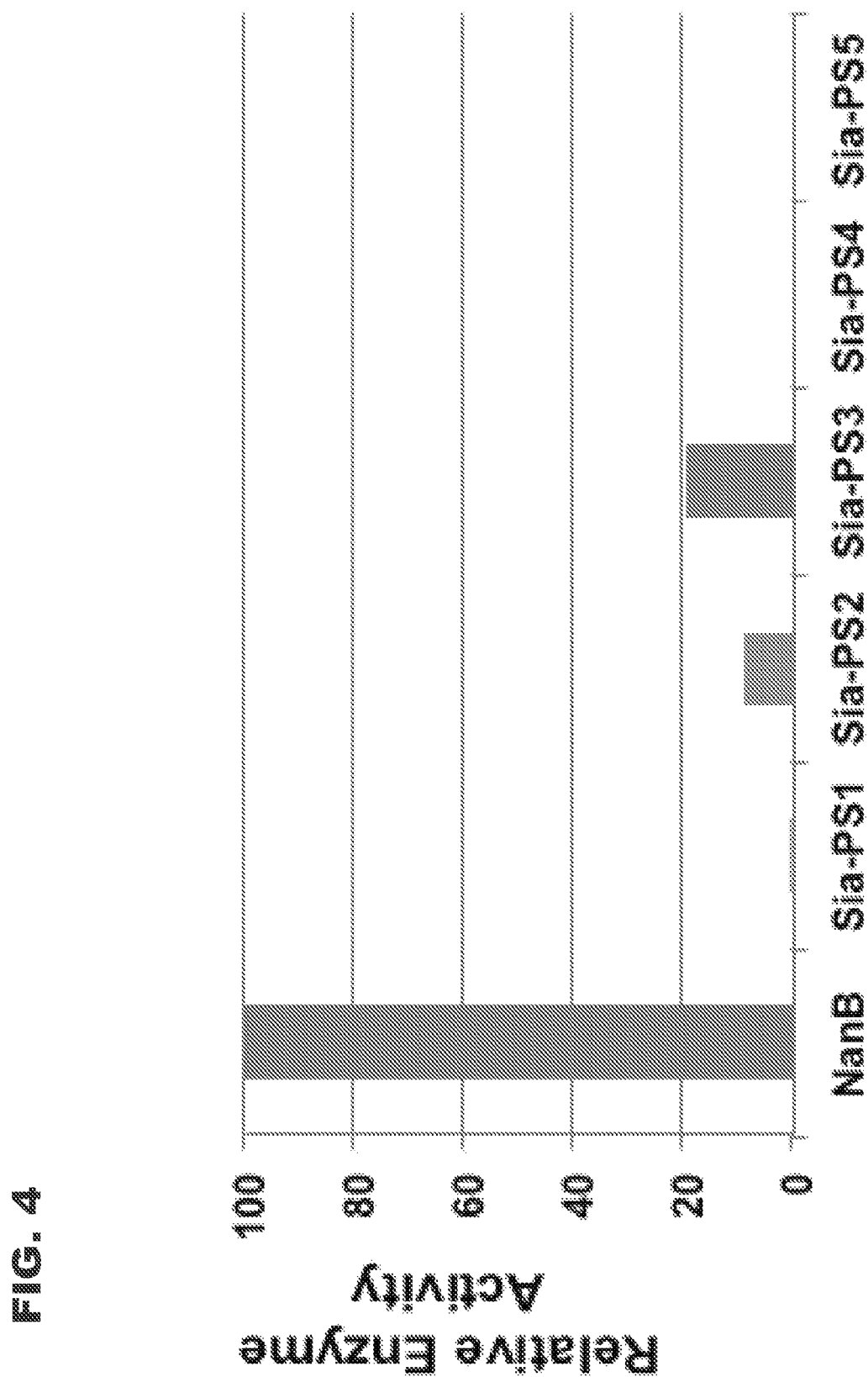
FIG. 4 shows relative enzymatic activity of NanB and Lectenz® clones.
Figure 5:
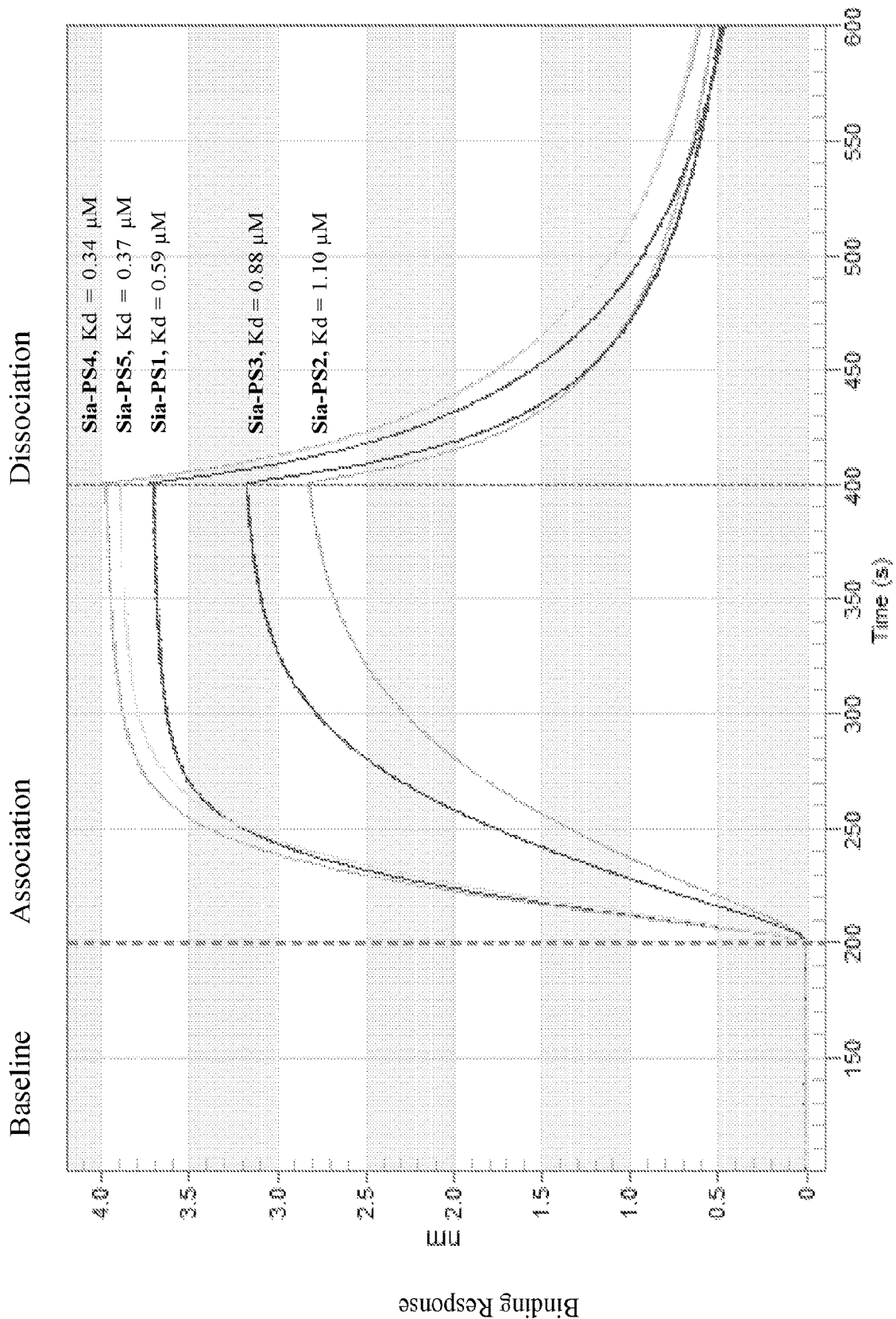
FIG. 5 shows BLI sensograms for the binding of Lectenz® candidates to 3'SL immobilized on biosensors.
Figure 16B:
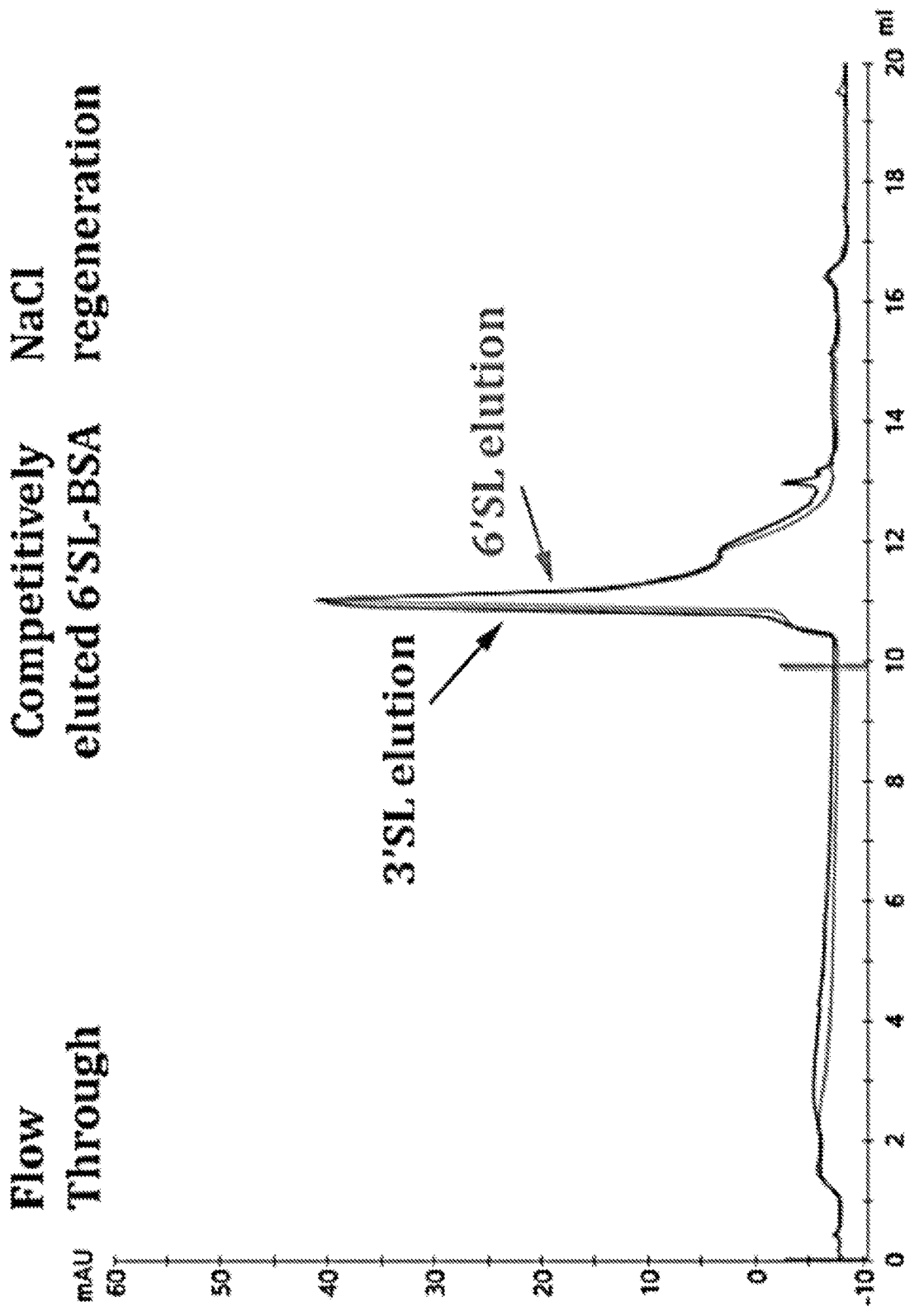

3'SL-BSA Bound to a Sia-3S1 LAC Column is Competitively Eluted by 3'SL but not 6'SL A Sia-31 LAC column was injected with 100 μg 3'SL-BSA (FIG. 16A) or 6'SL-BSA (FIG. 16B) before eluting with 50 mM 3'SL or 6'SL. In FIG. 16A, 3'SL is able to elute 90 of previously bound 3'SL-BSA. Attempting to elute bound 3'SL-BSA using 50 mM 6'SL only results in a small elution peak and the vast majority of 3'SL-BSA is eluted during the NaCl regeneration step. When 100 μg 6'SL-BSA is bound to the Sia-3S1 column (FIG. 16B), both 50 mM 3'SL and 6'SL elute 45 μg 6'SL-BSA. Taken together, these results demonstrate Sia-3S1 is binding selectively to 3'SL-BSA over 6'SL-BSA. The remaining quantity of 6'SL-BSA is in the flow through as indicated by the shallow and broad peak from 1.5 mL through 10 mL retention volume.

Separation of 3'SL-BSA Over 6'SL-BSA Using Sia-3S1 LAC

Figure 17:
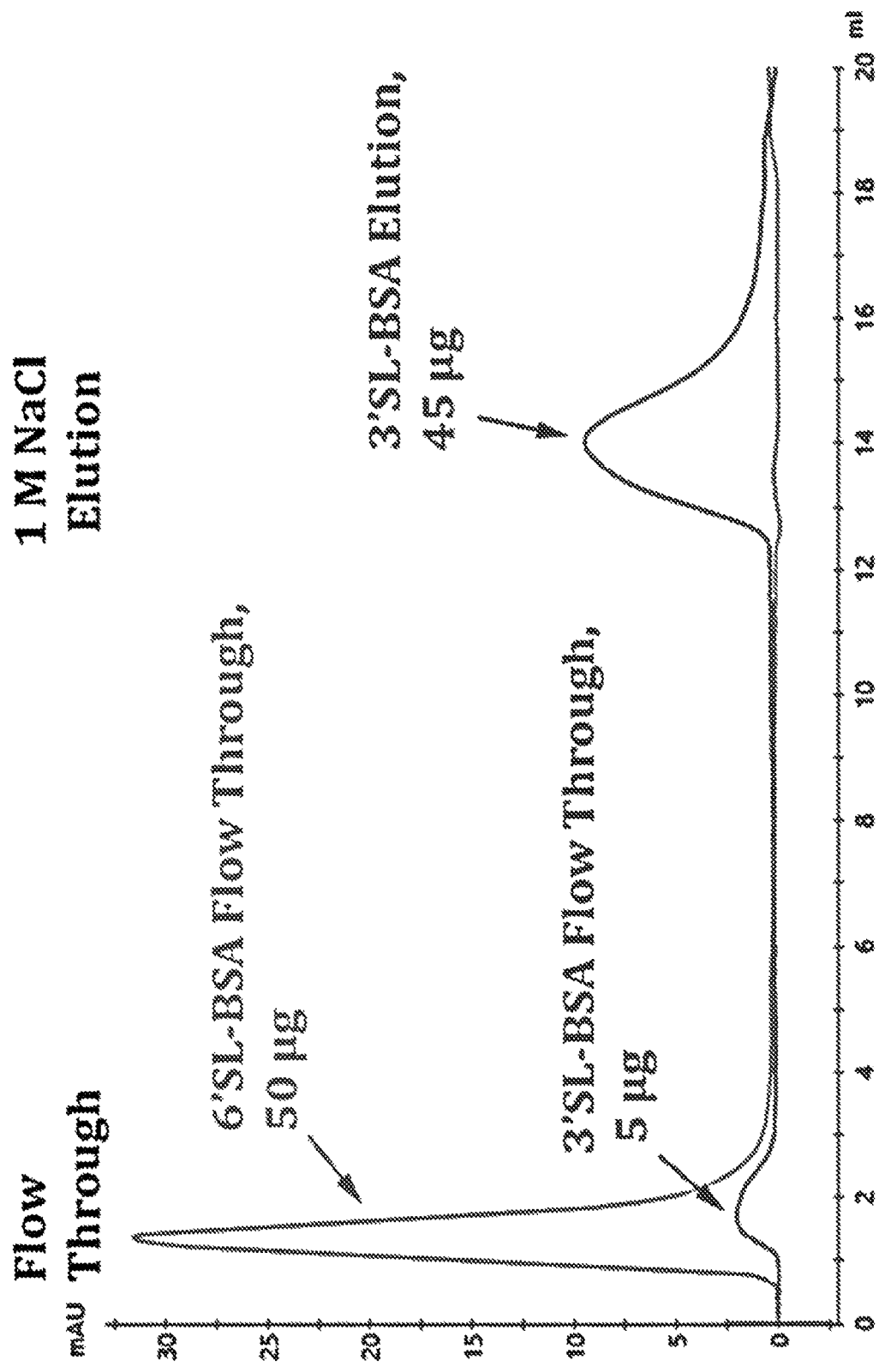
FIG. 17 shows that Sia-3S1 LAC column binds only to 3'SL-BSA using binding buffer with 110 mM NaCl. 50 µg 3'SL-BSA, or 6'SL-BSA was loaded onto the Sia-3S1 LAC column. Sialylated BSA molecules bound onto the Sia-3S1 column were eluted using 10 mM EPPS buffer (pH 7.5) with 1 M NaCl.

As illustrated in FIG. 17, Sia-3S1 LAC column was injected with 50 μg 3'SL-BSA or 6'SL-BSA in 10 mM EPPS (pH 7.5) binding buffer containing 110 mM NaCl. Under these conditions, all 50 μg of 6'SL-BSA was detected in the flow through, whereas only 5 μg 3'SL-BSA did not bind to the column. Subsequently, bound 3'SL-BSA was eluted using 10 mM EPPS (pH 7.5) buffer with 1 M NaCl. No 6'SL-BSA elution could be detected using the same EPPS buffer with 1 M NaCl. These results suggest that adjusting the NaCl concentration in binding buffer can result in 3'SL-BSA binding to the Sia-3S1 LAC column, whereas 6'SL-BSA does not.

Western Blot Using Sia-3S1

A sample (1 μg each) of asialofetuin, fetuin, BSA, 3'SL-BSA or 6'SL-BSA was run on an SDS-PAGE gel. The gel was transferred to a nitrocellulose membrane and blocked. 1 μM Sia-3S1 was incubated with the blot to probe for Neu5Acα2,3Gal. After washing, anti-Poly His-HRP conjugate was incubated with the blot to detect the N-terminal hexa-histidine tag of Sia-3S1. The blot was washed and developed with a chemiluminescent substrate. The image (FIG. 18) shows that Sia-3S1 binds only proteins with α2,3-linked sialylation: fetuin and 3'SL-BSA. (A faint band for asialofetuin may be due to trace amounts of fetuin in the commercial asialofetuin.) It does not bind BSA and, significantly, does not bind 6'SL-BSA. This is in contrast to the "Siaα2,3 specific" MAL II lectin, which shows no binding, except for a very faint band for fetuin. A band would be predicted for 3'SL-BSA, but none was observed.

Summary

1) Sia-3S1 Lectenz® has preferential affinity for 3'SL over 6'SL.
2) The Sia-3S1 Lectenz® is a functional capture reagent for the enrichment of 2,3-linked sialo-glycoproteins: more fetuin was eluted when using 3'SL for competitive elution than 6'SL as a competitive elution reagent.
3) Any 6'SL binding to Sia-3S1 Lectenz® on LAC is eliminated using a buffer with well-defined NaCl concentration.
4) Western blotting demonstrates that Sia-3S1 is a molecular probe specific to α2,3-linked sialic acid glycoconjugates that is far superior to commercial MAL II.

REFERENCES CITED

1. Chao, G., et al., *Isolating and engineering human antibodies using yeast surface display*. Nat. Protocols, 2006. 1(2): p. 755-768.
2. Zhao, J., et al., *Comparative serum glycoproteomics using lectin selected sialic acid glycoproteins with mass spectrometric analysis: application to pancreatic cancer serum*. J Proteome Res, 2006. 5(7): p. 1792-802.
3. Bai, X., et al., *Enhanced 3-O-sulfation of galactose in Asn-linked glycans and Maackia amurensis lectin binding in a new Chinese hamster ovary cell line*. Glycobiology, 2001. 11(8): p. 621-32.
4. Nicholls, J. M., et al., *Sialic acid receptor detection in the human respiratory tract: evidence for widespread distribution of potential binding sites for human and avian influenza viruses*. Respir Res, 2007. 8: p. 73.
5. Geisler, C. and D. L. Jarvis, *Effective glycoanalysis with Maackia amurensis lectins requires a clear understanding of their binding specificities*. Glycobiology, 2011. 21(8): p. 988-93.
6. Zheng, J., et al., *Serum 3'-sulfo-Lea indication of gastric cancer metastasis*. Clin Chim Acta, 2009. 405(1-2): p. 119-26.
7. Samraj, A. N., et al., *Involvement of a Non-Human Sialic Acid in Human Cancer*. Front Oncol, 2014. 4: p. 33.
8. Tajiri, M., C. Ohyama, and Y. Wada, *Oligosaccharide profiles of the prostate specific antigen in free and complexed forms from the prostate cancer patient serum and in seminal plasma: a glycopeptide approach*. Glycobiology, 2008. 18(1): p. 2-8.
9. Gut, H., S. J. King, and M. A. Walsh, *Structural and functional studies of Streptococcus pneumoniae neuraminidase B: An intramolecular trans-sialidase*. FEBS Lett, 2008. 582(23-24): p. 3348-52.
10. Ford, M. G., et al., *MD Simulations of Galectin-1 Oligosaccharide Complexes Reveal the Molecular Basis for Ligand Diversity*. Proteins: Struct. Funct. Genet., 2003. 53: p. 229-240.
11. Martin, J. C., et al., *Defining the Structural Origin of the Substrate Sequence Independence of O-GlcNAcase Using a Combination of Molecular Docking and Dynamics Simulation*. Glycobiology, 2013.
12. Kadirvelraj, R., et al., *Structure and Binding Analysis of Polyporus squamosus Lectin in Complex with the Neu5Acα2-6Gal/β1-4GlcNAc Human-type Influenza Receptor*. Glycobiology, 2011. 21(7): p. 973-984.
13. Woods, R. J. and M. B. Tessier, *Computational Glycoscience: Characterizing the Spatial and Temporal Properties of Glycans and Glycan Protein Complexes*. Curr. Opin. Struct. Biol., 2010. 20: p. 575-583.
14. Hadden, J. A., et al., *Calculating binding free energies for protein-carbohydrate complexes*. Method. Mol. Biol., 2015. 1273: p. 431-65.
15. Gasteiger E., H. C., Gattiker A., Duvaud S., Wilkins M. R., Appel R. D., Bairoch A., *Protein Identification and*

Analysis Tools on the ExPASy Server, in The Proteomics Protocols Handbook J. M. Walker, Editor. 2005, Copyright Humana Press. p. 571-607.
16. Haseley, S. R., et al., *Characterization of the carbohydrate binding specificity and kinetic parameters of lectins by using surface plasmon resonance*. Anal Biochem, 1999. 274(2): p. 203-10.
17. Yamamoto, K., Y. Konami, and T. Irimura, *Sialic acid-binding motif of Maackia amurensis lectins*. J. Biol. Chem., 1997. 121(4): p. 756-61.
18. Lee, L. Y., et al., *An optimized approach for enrichment of glycoproteins from cell culture lysates using native multi-lectin affinity chromatography*. J Sep Sci, 2012. 35(18): p. 2445-52.
19. Padler-Karavani, V., et al., *Cross-comparison of Protein Recognition of Sialic Acid Diversity on Two Novel Sialoglycan Microarrays*. Journal of Biological Chemistry, 2012. 287(27): p. 22593-22608.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A sialic acid-recognizing affinity reagent comprising a catalytically inactive NanB neuraminidase protein, or fragment thereof, comprising at least one amino acid mutation compared to a corresponding wild-type NanB neuraminidase protein, wherein the at least one amino acid mutation is (i) E541Q of SEQ ID NO:1 or E512Q of SEQ ID NO:4, (ii) R193A, D270Q, A538V, and E541D of SEQ ID NO:1 or R164A, D241Q, A509V, and E512D of SEQ ID NO:4, or (iii) E541A of SEQ ID NO:1 or E512A of SEQ ID NO:4.

2. The sialic acid-recognizing affinity reagent of claim 1, wherein the affinity reagent is pan-specific for sialic acid.

3. The sialic acid-recognizing affinity reagent of claim 2, wherein the affinity reagent binds to (i) Neu5Ac linked to an adjacent saccharide monomer in an α2,3 linkage, Neu5Ac linked to an adjacent saccharide monomer in an α2,6 linkage, and Neu5Ac linked to an adjacent saccharide monomer in an α2,8 linkage, (ii) binds to at least one variant of Neu5Ac, or (iii) binds to (i) and (ii).

4. The sialic acid-recognizing affinity reagent of claim 1, wherein the sialic acid-recognizing affinity reagent binds a sialylated glycan that is a constituent of a glycosylated biomolecule.

5. The sialic acid-recognizing affinity reagent of claim 4, wherein the glycosylated biomolecule comprises a glycoprotein, a glycopeptide, a glycolipid, a glycolipoprotein, or a glycolipopeptide.

6. A conjugate comprising a first component comprising the sialic acid-recognizing affinity reagent of claim 1, covalently linked to a second component.

7. The conjugate of claim 6, wherein the second component is a therapeutic or diagnostic agent.

8. A fusion protein comprising the sialic acid-recognizing affinity reagent of claim 1.

9. An affinity matrix comprising the sialic acid-recognizing affinity reagent of claim 1.

10. A kit comprising the sialic acid-recognizing affinity reagent of claim 1, and instructions for use.

11. A method for making the sialic acid-recognizing affinity reagent of claim 1, the method comprising expressing the affinity reagent in host cell.

12. A method for detecting a sialic acid component of a glycan, the method comprising:

contacting a biological or laboratory sample with the sialic acid-recognizing affinity reagent of claim 1 under conditions to allow binding of the affinity reagent to the sialic acid; and detecting the sialic acid.

13. A method for enriching, isolating or purifying a sialic acid-containing glycan, the method comprising:

contacting the sialic acid-recognizing affinity reagent of claim 1 under conditions to allow binding of the affinity reagent to the sialic acid so as to yield an enriched, isolated or purified sialic acid-containing glycan.

14. A diagnostic or therapeutic composition comprising the sialic acid-recognizing affinity reagent of claim 1.

15. A method comprising administering the sialic acid-recognizing affinity reagent of claim 1 to a subject, and detecting binding of the sialic acid-recognizing affinity reagent to a sialic acid-containing glycan.

16. The sialic acid-recognizing affinity reagent of claim 1, wherein the affinity reagent is specific for an α2,3-linked sialic acid.

* * * * *